(12) United States Patent
Fernandes et al.

(10) Patent No.: US 11,066,406 B2
(45) Date of Patent: Jul. 20, 2021

(54) SMALL MOLECULE INHIBITORS OF THE JAK FAMILY OF KINASES

(71) Applicant: Janssen Pharmaceutica NV, Beerse (BE)

(72) Inventors: Philippe Fernandes, Turnhout (BE); Paul J. Krawczuk, Newtown, PA (US); Mark S. Tichenor, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/776,243

(22) Filed: Jan. 29, 2020

(65) Prior Publication Data

US 2020/0165250 A1   May 28, 2020

Related U.S. Application Data

(63) Continuation of application No. 16/581,018, filed on Sep. 24, 2019, now abandoned, which is a continuation of application No. 16/441,656, filed on Jun. 14, 2019, now abandoned.

(60) Provisional application No. 62/846,290, filed on May 10, 2019, provisional application No. 62/685,737, filed on Jun. 15, 2018.

(51) Int. Cl.
*C07D 471/14* (2006.01)

(52) U.S. Cl.
CPC ........ *C07D 471/14* (2013.01); *C07B 2200/13* (2013.01)

(58) Field of Classification Search
CPC .......................... C07D 471/14; C07B 2200/13
See application file for complete search history.

(56) References Cited

U.S. PATENT DOCUMENTS

| | | | |
|---|---|---|---|
| 6,080,747 A | 6/2000 | Uckun et al. | |
| 8,426,411 B2* | 4/2013 | Wishart | A61K 31/4985 514/250 |
| 8,461,328 B2* | 6/2013 | Babu | A61P 19/02 540/597 |
| 8,785,639 B2* | 7/2014 | Wishart | C07F 9/06 546/82 |
| 8,841,078 B2 | 9/2014 | Silvennoinen et al. | |
| 8,962,629 B2* | 2/2015 | Wishart | C07D 487/14 514/250 |
| 10,294,226 B2* | 5/2019 | Koudriakova | A61P 19/02 |
| 10,364,246 B2* | 7/2019 | Koudriakova | A61P 13/12 |
| 10,487,083 B2* | 11/2019 | Kreutter | A61P 19/02 |
| 2009/0312338 A1 | 12/2009 | Wishart et al. | |
| 2011/0311474 A1 | 12/2011 | Wishart et al. | |
| 2013/0216497 A1 | 8/2013 | Wishart et al. | |
| 2015/0210708 A1 | 7/2015 | Wishart et al. | |
| 2019/0177321 A1 | 6/2019 | Koudriakova et al. | |
| 2019/0177322 A1 | 6/2019 | Kreutter et al. | |
| 2019/0322665 A1* | 10/2019 | Bacani | A61P 35/00 |
| 2020/0017498 A1 | 1/2020 | Fernandes et al. | |
| 2020/0338051 A1 | 10/2020 | Rizzolio | |

FOREIGN PATENT DOCUMENTS

| | | |
|---|---|---|
| CL | 201201396 | 9/2012 |
| CL | 201901077 | 4/2019 |
| CL | 201901416 | 5/2019 |
| CL | 201901551 | 6/2019 |
| CL | 201901651 | 6/2019 |
| CL | 201901652 | 6/2019 |
| CL | 201901991 | 7/2019 |
| CL | 201903015 | 10/2019 |
| WO | 2011068881 * | 6/2011 |
| WO | WO2011/068881 A1 | 6/2011 |
| WO | WO2011068899 A1 | 6/2011 |
| WO | WO2011/086053 A1 | 7/2011 |
| WO | WO2013/007765 A1 | 1/2013 |
| WO | WO2015/144773 A1 | 10/2015 |
| WO | WO2016/191524 A1 | 12/2016 |
| WO | WO2017/079639 A1 | 5/2017 |
| WO | WO2018077630 A1 | 5/2018 |
| WO | WO2018/112379 A1 | 6/2018 |
| WO | WO2018/112382 A1 | 6/2018 |
| WO | WO2018108671 A1 | 6/2018 |
| WO | WO2018109074 A1 | 6/2018 |
| WO | WO2018109607 A1 | 6/2018 |
| WO | WO2018111707 A1 | 6/2018 |
| WO | WO2018138303 A1 | 8/2018 |
| WO | WO2018195397 A2 | 10/2018 |
| WO | WO2019/239387 | 12/2019 |

OTHER PUBLICATIONS

U.S. Appl. No. 16/469,939, filed Jun. 14, 2019, Bacani, Genesis M., et al.

Alves De Medeiros, et al., JAK3 as an Emerging Target for Topical Treatment of Inflammatory Skin Diseases, PLoS ONE, 2016, pp. 1-16, 11(10): e0164080. doi:10.1371/journal.pone.0164080.

Amano, et al., JAK inhibitor JTE-052 regulates contact hypersensitivity by downmodulating T cell activation and differentiation, Journal of Dermatological Science, 2016, pp. 258-265, vol. 84.

Ambeu N'Ta C., et al., A practical multi-step synthesis of ethyl N-functionalized β-amino benzimidazole acrylate derivatives as promising cytotoxic agents, Molecular Diversity (2018) vol. 22, pp. 685-708.

Baumgart, et al., Inflammatory bowel disease: cause and immunobiology, Lancet, 2007, pp. 1627-1640, vol. 369.

Baumgart, et al., Inflammatory bowel disease: clinical aspects and established and evolving therapies, Lancet, 2007, pp. 1641-1657, vol. 369.

Baxter, et al., Acquired mutation of the tyrosine kinase JAK2 in human myeloproliferative disorders, Lancet, 2005, pp. 1054-1061, vol. 365.

Behbod, et al., Concomitant Inhibition of Janus Kinase 3 and Calcineurin-Dependent Signaling Pathways Synergistically Prolongs the Survival of Rat Heart Allografts, The Journal of Immunology, 2001, pp. 3724-3732, vol. 166.

(Continued)

*Primary Examiner* — D Margaret M Seaman

(57) ABSTRACT

2-((1r,4r)-4-(imidazo[4,5-d]pyrrolo[2,3-b]pyridin-1(6H)-yl)cyclohexyl)acetonitrile compounds, pharmaceutical compositions containing them, methods of making them, and methods of using them including methods for treating disease states, disorders, and conditions mediated by JAK.

1 Claim, 34 Drawing Sheets

(56) References Cited

OTHER PUBLICATIONS

Benveniste, et al., Involvement of the Janus Kinase/Signal Transducer and Activator of Transcription Signaling Pathway in Multiple Sclerosis and the Animal Model of Experimental Autoimmune Encephalomyelitis, Journal of Interferon & Cytokine Research, 2014, pp. 577-588, vol. 34, Issue 8.
Berge, et al., Pharmaceutical Salts, Journal of Pharmaceutical Sciences, 1977, pp. 1-19, vol. 66, No. 1.
Berthier, et al., Enhanced Expression of Janus Kinase-Signal Transducer and Activator of Transcription Pathway Members in Human Diabetic Nephropathy, Diabetes, 2009, pp. 469-477, vol. 58.
Bissonnette, et al., Topical tofacitinib for atopic dermatitis: a phase IIa randomized trial, British Journal of Dermatology, 2016, pp. 902-911, vol. 175.
Brosius, et al., JAK inhibition in the treatment of diabetic kidney disease, Diabetologia, 2016, pp. 1624-1627, vol. 59.
Bunnage, Mark E., Getting pharmaceutical R&D back on target, Nature Chemical Biology, 2011, pp. 335-339, vol. 7.
Busque, et al., Calcineurin-Inhibitor-Free Immunosuppression Based on the JAK Inhibitor CP-690,550: A Pilot Study in De Novo Kidney Allograft Recipients, American Journal of Transplantation, 2009, pp. 1936-1945, vol. 9.
Cargill, et al., A Large-Scale Genetic Association Study Confirms IL12B and Leads to the Identification of IL23R as Psoriasis-Risk Genes, The American Journal of Human Genetics, 2007, pp. 273-290, vol. 80.
Casanova, et al., Revisiting Crohn's disease as a primary immunodeficiency of macrophages, J. Exp. Med., 2009, pp. 1839-1843, vol. 206, No. 9.
Chan et al., Dose-dependent reduction in psoriasis severity as evidence of immunosuppressive activity of an oral Jak3 inhibitor in humans, Am. J. Transplant., 2006, S87, vol. 6.
Changelian, et al., Prevention of Organ Allograft Rejection by a Specific Janus Kinase 3 Inhibitor, Science, 2003, pp. 875-878, vol. 302.
Charmot, Dominique, Non-Systemic Drugs: A Critical Review, Current Pharmaceutical Design, 2012, pp. 1434-1445, vol. 18.
Clark, et al., Discovery and Development of Janus Kinase (JAK) Inhibitors for Inflammatory Diseases, Journal of Medicinal Chemistry, 2014, pp. 5023-5038, vol. 57.
Colligris, et al., Recent developments on dry eye disease treatment compounds, Saudi Journal of Ophthalmology, 2014, pp. 19-30, vol. 28.
Coskun, et al., Involvement of JAK/STAT signaling in the pathogenesis of inflammatory bowel disease, Pharmacological Research, 2013, pp. 1-8, vol. 76.
Danese, et al., JAK inhibition using tofacitinib for inflammatory bowel disease treatment: a hub for multiple inflammatory cytokines, Am J Physiol Gastrointest Liver Physiol, 2016, pp. G155-G162, vol. 310.
Duerr, et al., A Genome-Wide Association Study Identifies IL23R as an Inflammatory Bowel Disease Gene, Science, 2006, pp. 1461-1463, vol. 314.
Filipski, et al., Intestinal Targeting of Drugs: Rational Design Approaches and Challenges, Current Topics in Medicinal Chemistry, 2013, pp. 776-802, vol. 13.
Folster-Holst, et al., Topical hydrocortisone 17-butyrate 21-propionate in the treatment of inflammatory skin diseases: pharmacological data, clinical efficacy, safety and calculation of the therapeutic index, Pharmazie, 2016, pp. 115-121, vol. 71.
Fujimura, et al., Significance of Interleukin-6/STAT Pathway for the Gene Expression of REG Iα, A New Autoantigen in Sjögren's Syndrome Patients, in Salivary Duct Epithelial Cells, Clinic Rev Allerg Immunol, 2016, pp. 1-13, DOI 10.1007/s12016-016-8570-7.
Fukuyama, et al., Topically Administered Janus-Kinase Inhibitors Tofacitinib and Oclacitinib Display Impressive Antipruritic and Anti-Inflammatory Responses in a Model of Allergic Dermatitis, J Pharmacol Exp Ther, 2015, pp. 394-405, vol. 354.

Furumoto, et al., Tofacitinib Ameliorates Murine Lupus and Its Associated Vascular Dysfunction, Arthritis & Rheumatology, 2017, pp. 148-160, vol. 69 Issue 1.
Fyfe, Matthew C.T., Non-systemic Intestine-Targeted Drugs, Progress in Medicinal Chemistry, 2016, pp. 1-44, vol. 55.
Gaudana, et al., Ocular Drug Delivery, The AAPS Journal, 2010, pp. 348-360, vol. 12 Issue 3.
Ginzinger, Werner, et al., A SAR Study of Novel Antiproliferative Ruthenium and Osmium Complexes with Quinoxalinone Ligands in Human Cancer Cell Lines, J. Med. Chem. (2012) vol. 55, pp. 3398-3413.
Goropevsek, et al., The Role of STAT Signaling Pathways in the Pathogenesis of Systemic Lupus Erythematosus, Clinic Rev Allerg Immunol, May 23, 2016, pp. 1-18, DOI 10.1007/512016-016-8550-y.
Gurzov, et al., The JAK/STAT pathway in obesity and diabetes, The FEBS Journal, 2016, pp. 3002-3015, vol. 283.
Hay, et al., Clinical development success rates for investigational drugs, Nature Biotechnology, 2014, pp. 40-51, vol. 32 Issue 1.
Helandr, et al., Surface area of the digestive tract—revisited, Scandinavian Journal of Gastroenterology, 2014, pp. 681-689, vol. 49.
Hirschmann, Ralph, et al., Nonpeptidal Peptidomimetics with a β-D-Glucose Scaffolding. A Partial Somatostatin Agonist Bearing a Close Structural Relationship to a Potent, Selective Substance P Antagonist, J. Am. Chem. Soc. (1992) vol. 114, pp. 9217-9218.
Honda, Masanori, et al., A Synthesis of (±)-Brefeldin A, Tetrahedron Letters (1981) vol. 22, No. 28, pp. 2679-2682.
International Search Report and Written Opinion dated Apr. 4, 2018, for International Application PCT/US2017/066754.
International Search Report and Written Opinion dated May 11, 2018, for International Application PCT/US2017/066744.
James, et al., A unique clonal JAK2 mutation leading to constitutive signalling causes polycythaemia vera, Nature, 2005, pp. 1144-1148, vol. 434.
Jursic, Branko S., et al., A Simple Preparation of Amides from Acids and Amines by Heating of their Mixture, Synthetic Communications, (1993), vol. 23, No. 19, pp. 2761-2770.
Kawasaki, et al., Possible role of the JAK/STAT pathways in the regulation of T cell-interferon related genes in systemic lupus erythematosus, Lupus, 2011, pp. 1231-1239, vol. 20.
Kocienski, Philip J., Chapter 6.3.1: N-Sulfonyl Derivatives of Indoles, Pyrroles, and Imidazoles, Protecting Groups; Georg Thieme Verlag Stuttgart: NY, (1994), pp. 209-211.
Kola, et al., Can the pharmaceutical industry reduce attrition rates?, Nature Reviews/Drug Discovery, 2004, pp. 711-715, vol. 3.
Kontzias et al., Jakinibs: A new class of kinase inhibitors in cancer and autoimmune disease, Current Opinion in Pharmacology, 2012, pp. 464-470, vol. 12.
Kopf et al., Averting inflammation by targeting the cytokine environment, Nature Reviews/Drug Discovery, 2010, pp. 703-718, vol. 9.
Kornbluth, et al., Ulcerative Colitis Practice Guidelines in Adults: American College of Gastroenterology, Practice Parameters Committee, the American Journal of Gastroenterology, 2010, pp. 501-523, vol. 105.
Kralovics, et al., A Gain-of-Function Mutation of JAK2 in Myeloproliferative Disorders, The New England Journal of Medicine, 2005, pp-1779-1790, vol. 352 Issue 17.
Kremer, et al., a Randomized, Double-Blind, Placebo-Controlled Trial of 3 Dose Levels of CP690,550 Versus Placebo in the Treatment of Active Rheumatoid Arthritis, Arthritis Rheum. 54 (annual meeting abstract), 2006, L40.
Kremer, et al., The Safety and Efficacy of a JAK Inhibitor in Patients with Active Rheumatoid Arthritis, Arthritis & Rheumatism, 2009, pp. 1895-1905, vol. 60 Issue 7.
Kumar, Vasantha et al., Synthesis of Some Novel 1,2-Disubstituted Benzimidazole-5-Carboxylates Via One-Pot Method Using Sodium Dithionite and its Effect on N-Debenzylation, Synthetic Communications (2014) vol. 44, pp. 3414-3425.
Lalande, et al., Mycobacteria in Crohn's disease: how innate immune deficiency may result in chronic inflammation, Expert Review of Clinical Immunology, 2010, pp. 633-641, vol. 6 Issue 4.

(56) References Cited

OTHER PUBLICATIONS

Langholz, et al., Course of Ulcerative Colitis: Analysis of Changes in Disease Activity Over Years, Gastroenterology, 1994, pp. 3-11, vol. 107 Issue 01.

Leonard!, et al., Efficacy and safety of ustekinumab, a human interleukin-12/23 monoclonal antibody, in patients with psoriasis: 76-week results from a randomised, double-blind, placebo-controlled trial (Phoenix 1), Lancet, 2008, pp. 1665-1674, vol. 371.

Levine, et al., Activating Mutation in the Tyrosine Kinase JAK2 in Polycythemia Vera, Essential Thrombocythemia, and Myeloid Metaplasia with Myelofibrosis, Cancer Cell, 2005, pp. 387-397, vol. 7.

Li, et al., Effect of miR-19a and miR-21 on the JAK/STAT signaling pathway in the peripheral blood mononuclear cells of patients with systemic juvenile idiopathic arthritis, Experimental and Therapeutic Medicine, 2016, pp. 2531-2536, vol. 11.

Liu, et al., Therapeutic Efficacy of Suppressing the Jak/Stat Pathway in Multiple Models of Experimental Autoimmune Encephalomyelitis, The Journal of Immunology, 2014, pp. 59-72, vol. 192.

Liu, Zhenming et al., Identification of Small-Molecule Inhibitors against Human Leukocyte Antigen-Death Receptor 4 (HLA-DR4) Through a Comprehensive Strategy, J. Chem. Inf. Model. (2011) vol. 51, pp. 326-334.

Marks, et al., Crohn's Disease: an Immune Deficiency State, Clinic Rev Allerg Immunol, 2010, pp. 20-31, vol. 38.

Menet, et al., Triazolopyridines as Selective JAK1 Inhibitors: From Hit Identification to GLPG0634, Journal of Medicinal Chemistry, 2014, pp. 9323-9342, vol. 57.

Nangia, Ashwini, Pseudopolymorph: Retain This Widely Accepted Term, Crystal Growth & Design, 2006, pp. 2-4, vol. 6 Issue 1.

Neurath, Markus F., Cytokines in inflammatory bowel disease, Nature Reviews/Immunology, 2014, pp. 329-342, vol. 14.

NIDDK (National Institute of Diabetes, and Digestive and Kidney Diseases, National Institutes of Health, US Department of Health and Human Services, <http://spotidoc.com/doc/71780/crohns-disease---national-digestive-diseases-information>, accessed Nov. 29, 2016.

Nielsen, et al., Will novel oral formulations change the management of inflammatory bowel disease?, Expert Opinion on Investigational Drugs, 2016, pp. 709-718, vol. 25 Issue 6.

Nishimoto, et al., Study of active controlled monotherapy used for rheumatoid arthritis, an IL-6 inhibitor (SAMURAI): evidence of clinical and radiographic benefit from an x ray reader-blinded randomised controlled trial of tocilizumab, Ann Rheum Dis, 2007, pp. 1162-1167, vol. 66.

Norman, Peter, Selective JAK inhibitors in development for rheumatoid arthritis, Expert Opinion on Investigational Drugs, 2014, pp. 1067-1077, vol. 23 Issue 8.

Oda, Shinichi et al., Development of Safe One-Pot Synthesis of N-1- and C-2-Substituted Benzimidazole via Reductive Cyclization of o-Nitroarylamine Using Na2S2O4, Org. Process Res. Dev. (2012) vol. 16, pp. 96-101.

O'Shea, et al., JAKs and STATs in Immunity, Immunodeficiency, and Cancer, The New England Journal of Medicine, 2013, pp. 161-170, vol. 368.

O'Shea, et al., A New Modality for Immunosuppression: Targeting the JAK/STAT Pathway, Nature Reviews/Drug Discovery, 2004, pp. 555-564, vol. 3.

O'Shea, et al., Janus kinase inhibitors in autoimmune diseases, Ann Rheum Dis, 2013, pp. ii111-ii115, vol. 72.

Özil, Musa et al., A simple and efficient synthesis of benzimidazoles containing piperazine or morpholine skeleton at C-6 position as glucosidase inhibitors with antioxidant activity, Bioorganic Chemistry (2018) vol. 76, pp. 468-477.

Panes, et al., Efficacy and safety of oral tofacitinib for induction therapy in patients with moderate-to-severe Crohn's disease: results of a Phase 2b randomised placebo-controlled trial, J. Crohn's Colitis, 2016, S18-S19, vol. 10.

Papp, et al., Efficacy and safety of tofacitinib, an oral Janus kinase inhibitor, in the treatment of psoriasis: a Phase 2b randomized placebo-controlled dose-ranging study, British Journal of Dermatology, 2012, pp. 668-677, vol. 167.

Patil, et al., Pulmonary drug delivery strategies: A concise, systematic review, Lung India, 2012, pp. 44-49, vol. 29 Issue 1.

Pesu et al., Therapeutic targeting of Janus kinases, Immunological Reviews, 2008, pp. 132-142, vol. 223.

Qiao, et al., Pharmaceutical cocrystals: An overview, International Journal of Pharmaceutics, 2011, pp. 1-11, vol. 419.

Reinisch, et al., Adalimumab for induction of clinical remission in moderately to severely active ulcerative colitis: results of a randomised controlled trial, Gut, 2011, pp. 780-787, vol. 60.

Rylander, P.N., Chapter 8: Hydrogenation of Nitro Compounds, Hydrogenation Methods; Academic Press: NY, (1985) pp. 104-116.

Rylander, P.N., Choosing and Using Noble Metal Hydrogenation Catalysts, Aldrichimica Acta (1979), vol. 12, No. 3, pp. 53-57.

Sandborn, et al., A Phase 2 Study of Tofacitinib, an Oral Janus Kinase Inhibitor, in Patients With Crohn's Disease, Clinical Gastroenterology and Hepatology, 2014, pp. 1485-1493, vol. 12 Issue 9.

Sandborn, et al., Efficacy and safety of oral tofacitinib as induction therapy in patients with moderate-to-severe ulcerative colitis: results from 2 phase 3 randomised controlled trials, J. Crohn's Colitis, 2016, S15-S, vol. 10.

Sandborn, et al., Tofacitinib, an Oral Janus Kinase Inhibitor, in Active Ulcerative Colitis, N Engl J Med, 2012, pp. 616-624, vol. 367 Issue 7.

Segal, et al., Repeated subcutaneous injections of IL12/23 p40 neutralising antibody, ustekinumab, in patients with relapsing-remitting multiple sclerosis: a phase II, double-blind, placebo-controlled, randomised, dose-ranging study, Lancet Neurol, 2008, pp. 796-804, vol. 7.

Shan, et al., the role of cocrystals in pharmaceutical science, Drug Discovery Today, 2008, pp. 440-446, vol. 13 Nos. 9/10.

Stephenson et al., Physical Stability of Salts of Weak Bases in the Solid-State, Journal of Pharmaceutical Sciences, 2011, pp. 1607-1617, vol. 100 Issue 5.

Strober, et al., Proinflammatory Cytokines in the Pathogenesis of Inflammatory Bowel Diseases, Gastroenterology, 2011, pp. 1756-1767, vol. 140 Issue 6.

Thakuria, et al., Pharmaceutical cocrystals and poorly soluble drugs, International Journal of Pharmaceutics, 2013, pp. 101-125, vol. 453.

Thomas et al., The role of JAK/STAT signaling in the pathogenesis, prognosis and treatment of solid tumours, British Journal of Cancer, 2015, pp. 365-371, vol. 113.

Thompson, et al., Anti cytokine therapy in chronic inflammatory arthritis, Cytokine, 2016, pp. 92-99, vol. 86.

Torchilin, Vladimir P., Drug targeting, European Journal of Pharmaceutical Sciences, 2000, pp. S81-S91, vol. 11 Suppl. 2.

Travis et al., European evidence-based Consensus on the management of ulcerative colitis: Current management, Journal of Crohn's and Colitis, 2008, pp. 24-62, vol. 2.

Vale, Kara, Targeting the JAK-STAT pathway in the treatment of 'Th2-high' severe asthma, Future Med. Chem., 2016, pp. 405-419, vol. 8 Issue 4.

Vermeire, et al., Filgotinib (GLPG0634), an Oral JAK1 Selective Inhibitor, Induces Clinical Remission in Patients With Moderate-to-Severe Crohn's Disease: Results From the Phase 2 FITZROY Study Interim Analysis, Gastroenterology, 2016, S-1267, vol. 150.

Waldner et al., Master regulator of intestinal disease: IL-6 in chronic inflammation and cancer development, Seminars in Immunology, 2014, pp. 75-79, vol. 26.

Waring, et al., an analysis of the attrition of drug candidates from four major pharmaceutical companies, Nature Reviews/Drug Discovery, 2015, pp. 475-486, vol. 14.

Wernig, et al., Efficacy of TG101348, a Selective JAK2 Inhibitor, in Treatment of a Murine Model of JAK2V617F-Induced Polycythemia Vera, Cancer Cell, 2008, pp. 311-320, vol. 13.

Wilding, et al., Targeting of Drugs and Vaccines to the Gut, Pharmac. Ther., 1994, pp. 97-124, vol. 62.

Williams et al., A randomized placebo-controlled study of INCB018424, a selective Janus kinase1&2 (JAK1&2) inhibitor in rheumatoid arthritis (RA), Arthritis Rheum., 2008, 5431, vol. 58.

(56) References Cited

OTHER PUBLICATIONS

Wolk, et al., New targeting strategies in drug therapy of inflammatory bowel disease: mechanistic approaches and opportunities, Expert Opin. Drug Deliv., 2013, pp. 1275-1286, vol. 10 Issue 9.

Xing, et al., Alopecia areata is driven by cytotoxic T lymphocytes and is reversed by JAK inhibition, Nature Medicine, 2014, pp. 1043-1051, vol. 20 Issue 9.

Yamamoto-Furusho, et al., Crohn's disease: Innate immunodeficiency, World J Gastroenterol, 2006, pp. 6751-6755, vol. 12 Issue 42.

Yan, et al., Role of the JAK/STAT signaling pathway in regulation of innate immunity in neuroinflammatory diseases, Clin. Immunol., 2016, http://dx.doi.org/10.1016/j.clim.2016.09.014.

Zak, et al., Discovery and Optimization of C-2 Methyl Imidazopyrrolopyridines as Potent and Orally Bioavailable JAK1 Inhibitors with Selectivity over JAK2, J. Med. Chem, 2012, pp. 6176-6193, vol. 55.

Zak, Mark et al., Identification of C-2 Hydroxyethyl Imidazopyrrolopyridines as Potent JAK1 Inhibitors with Favorable Physicochemical Properties and High Selectivity over JAK2, J. Med. Chem. 2013, 56, 4764-4785.

Zakhs, E.R., et al., Synthesis and Photochromic Properties of 2-(3-Nitro-2-pyridylmethyl)benzazoles, Russian Journal of General Chemistry, (2001) vol. 71, No. 7, pp. 1076-1087. Translated from Zhurnal Obshchei Khimii, (2001) vol. 71, No. 7, pp. 1142-1153.

International Search Report and Written Opinion dated Dec. 2, 2019, for International Application PCT/IB2019/055005.

U.S. Appl. No. 16/441,656, filed Jun. 14, 2019, Philippe Fernandes et al.

Notification of Decision Concerning Request for Rectification dated Jun. 15, 2020 for International Application No. PCT/IB2019/055005, 2 pages.

Ma, Christopher et al., "Systematic review with meta-analysis: efficacy and safety of oral Janus kinase inhibitors for inflammatory bowel disease", Aliment Pharmacol Ther., (2019) vol. 50, pp. 5-23.

Leonard, K., et al., "Discovery of a Gut-Restricted JAK Inhibitor for the Treatment of Inflammatory Bowel Disease", J. Med. Chem. 2020, vol. 63, pp. 2915-2929.

\* cited by examiner

SMALL MOLECULE INHIBITORS OF THE JAK FAMILY OF KINASES This application is a continuation of U.S. application Ser. No. 16/581,081 filed on Sep. 24, 2019, which is a continuation of U.S. application Ser. No. 16/441,656 filed on Jun. 14, 2019, now abandoned, which claims the benefit of U.S. Provisional Application 62/846,290 filed on May 10, 2019, and U.S. Provisional Application 62/685,737, filed on Jun. 15, 2018.

FIELD OF THE INVENTION

The present invention relates to certain imidazopyrrolopyridine compounds, pharmaceutical compositions containing them, methods of making them, and methods of using them as JAK inhibitors and for the treatment of disease states, disorders, and conditions mediated by JAK.

BACKGROUND

Internal factors, external factors or a combination of both factors can trigger or be associated with the development of abnormal immune responses in the body. Consequently, pathological states develop in which constituents, such as substances and tissues, that are normally present in the body are subject to such immune response. These states are generically referred to as immune system diseases. Because the body's immune system is involved and the damage affects body tissue, such diseases are also referred to as autoimmune diseases. Because such system and tissue are part of the same body, the terms "autoimmune disease" and "immune system disease" are used here interchangeably, regardless of what triggers the anomalous immune system response. Furthermore, the identity or the mechanism of the underlying immune problem is not always clear. See, for example, D. J. Marks, et al., Crohn's disease: An immune deficiency state, Clinical Reviews in Allergy and Immunology 38(1), 20-30 (2010); J. D. Lalande, et al, Mycobacteria in Crohn's disease: How innate immune deficiency may result in chronic inflammation, Expert Reviews of Clinical Immunology 6(4), 633-41 (2010); J. K. Yamamoto-Furusho, et al., Crohn's disease: Innate immunodeficiency, World Journal of Gastroenterology, 12(42), 6751-55 (2006). As used herein, the term "autoimmune disease" does not exclude conditions whose causes comprise external factors or agents, such as environmental or bacterial factors, and internal factors such as genetic susceptibility. Accordingly, a condition such as Crohn's disease (CD) is referred to herein as an autoimmune disease, regardless of whether it is triggered by the body itself or by external factors. See, e.g., J. L. Casanova, et al., Revisiting Crohn's disease as a primary immunodeficiency of macrophages, J. Exp. Med. 206(9), 1839-43 (2009).

Among the various adverse effects caused by autoimmune diseases, at least one of the following is typically observed: Damage to, and sometimes destruction of, tissues, and organ alteration that can impact organ growth and organ function. Examples of autoimmune diseases affect most major organs, endocrine and exocrine glands, the blood and muscles, and a plurality of systems, such as the digestive, vascular, connective and nervous systems. Immunosuppressive treatments are often adopted to treat autoimmune diseases.

Multiple theories are known to explain how autoimmune diseases arise, some focusing on endogenous factors and others also including exogenous factors. At the molecular level, the Janus kinase/signal transducer and activator of transcription (JAK/STAT) signaling pathway is considered to play an important role in transmitting information from extracellular chemical signals to the cell nucleus resulting in regulation of genes that are involved in cellular activities such as immunity. Cytokines are an example of an extracellular molecule that plays an important role in cell signaling. Leukocytes such as neutrophils are recruited by cytokines and chemokines to ultimately cause tissue damage in chronic inflammatory diseases.

The Janus kinase (JAK) family of proteins consists of 4 tyrosine kinases, JAK1, JAK2, JAK3 and Tyk2, which are central to the intracellular signaling of type I and type II cytokine receptors. The term JAK refers to either JAK1, JAK2, JAK3 or Tyk2, or any combination thereof. Each JAK selectively associates with receptor subunits which dimerize (or multimerize) to form functional receptors. According to J. D. Clark, et al., Discovery and Development of Janus Kinase (JAK) Inhibitors for Inflammatory Diseases, J. Med. Chem. 57(12), 5023-38 (2014), "the activation step occurs when a cytokine binds to its receptor, inducing a multimerization (dimerization or higher order complexes) of receptor subunits. This brings the JAKs associated with each subunit proximal to one another, triggering a series of phosphorylation events ultimately resulting in the phosphorylation and activation of signal transducers and activators of transcription (STAT) proteins. A phosphorylated STAT dimer then translocates to the nucleus of the cell where it binds to target genes modulating their expression." Once in the nucleus, STATs regulate gene transcription of numerous mediators in the inflammatory process via binding to specific recognition sites on DNA. See, for example, J. Med. Chem. 57(12), 5023-38 (2014), cited above. Considerable evidence exists demonstrating the importance for the JAK/STAT pathway in inflammatory, autoimmune diseases and cancer. See, for example, M. Coskun, et al., Involvement of JAK/STAT signaling in the pathogenesis of inflammatory bowel disease, Pharmacological Research 76, 1-8 (2013); and J. J. O'Shea, et al., JAKs and STATs in immunity, immunodeficiency, and cancer, The New England Journal of Medicine 368, 161-70 (2013).

Inflammatory bowel diseases, including Crohn's disease and ulcerative colitis (UC), are characterized by recurrent intestinal inflammation, disruption of the epithelial barrier and microbial dysbiosis. The excessive inflammatory response in the gastrointestinal tract is mediated by several pro-inflammatory cytokines including TNFα, IFN-γ, IL-1, IL-2, IL-4, IL-6, IL-12, IL-13, IL-15, IL-17, IL-21, and IL-23 that exert their effects on cells of the innate and adaptive immune system including T and B lymphocytes, epithelial cells, macrophages and dendritic cells (DC). See, for example, Pharmacological Research 76, 1-8 (2013), cited above; S. Danese, et al., JAK inhibition using tofacitinib for inflammatory bowel disease treatment: A hub for multiple inflammatory cytokines, American Journal of Physiology, Gastrointestinal and Liver Physiology 310, G155-62 (2016); and M. F. Neurath, Cytokines in inflammatory bowel disease, Nature Reviews Immunology 14, 329-42 (2014).

Prevention and/or control of such excessive inflammatory response is desireable. In light of the mechanism of such response as summarized above, JAK inhibition (see illustration in FIG. 1 in the form of an jagged arrow showing a pan-JAK inhibitor striking upon the JAK/STAT signaling pathway and inflammation) is envisaged to prevent or control excessive inflammatory response. JAK inhibitors that inhibit a plurality of such JAK proteins, are referred to here as pan-JAK inhibitors. Examples of therapeutic benefits of such prevention or control have been seen with tofacitinib, an orally bioavailable pan-JAK inhibitor approved in the United States for the treatment of rheumatoid arthritis and currently in clinical development for ulcerative colitis. In a Phase 2 clinical trial, 194 patients with moderate to severe ulcerative colitis were reportedly evaluated for clinical efficacy. See, e.g., W. J. Sandborn, et al., Tofacitinib, an oral Janus kinase inhibitor, in active ulcerative colitis, The New England Journal of Medicine 367, 616-24 (2012). Published information on this trial indicates that patients receiving twice a day (BID) doses of 0.5, 3, 10 and 15 mg achieved clinical response rates of 32, 48, 61 and 78%, respectively, compared to 42% observed in placebo. It was further reported that the secondary end point of clinical remission (Mayo score ≤2) was 13, 33, 48 and 41% compared to 10% observed in placebo. See, e.g., The New England Journal of Medicine 367, 616-24 (2012), cited above. In a Phase 3 UC clinical trial, 88 out of 476 patients reportedly achieved clinical remission following 8 weeks of treatment with tofacitinib (10 mg BID) compared to 10 out of 122 patients receiving placebo treatment. See W. J. Sandborn, et al. Efficacy and safety of oral tofacitinib as induction therapy in patients with moderate-to-severe ulcerative colitis: results from 2 phase 3 randomised controlled trials, J. Crohns Colitis 10, S15-S (2016). Reports on Crohn's disease indicate that tofacitinib was also in development for the treatment of CD; however, it was reportedly discontinued due to failure to achieve clinical efficacy in a 4 week/Phase 2 clinical trial for moderate to severe CD. See W. J. Sandborn, et al., A phase 2 study of tofacitinib, an oral Janus kinase inhibitor, in patients with Crohn's disease, Clinical gastroenterology and hepatology: The official clinical practice journal of the American Gastroenterological Association 12, 1485-93 e2 (2014). Based on consulted publicly available literature, it is currently unclear whether the tofacitinib failure in CD relates to clinical study design, mechanistic differences between UC and CD or dose-limiting systemic adverse events. See Pharmacological Research 76, 1-8 (2013), cited above; Clinical gastroenterology and hepatology: the official clinical practice journal of the American Gastroenterological Association 12, 1485-93 e2 (2014), cited above; and C. J. Menet, et al., Triazolopyridines as selective JAK1 inhibitors: from hit identification to GLPG0634, J. Med. Chem. 57, 9323-42 (2014). In light of the features of this JAK inhibitor, it is desirable to find additional JAK inhibitors for the prevention and/or control of excessive inflammatory response.

Systemic adverse events have been reported with respect to both Phase 2 and Phase 3 inflammatory bowel disease (IBD) clinical trials with tofacitinib. See The New England Journal of Medicine 367, 616-24 (2012), cited above; Clinical gastroenterology and hepatology: the official clinical practice journal of the American Gastroenterological Association 12, 1485-93 e2 (2014), cited above; and J. Panes, et al. Efficacy and safety of oral tofacitinib for induction therapy in patients with moderate-to-severe Crohn's disease: results of a Phase 2b randomised placebo-controlled trial, J. Crohns Colitis 10, S18-S19 (2016). These adverse events include decreased absolute neutrophil counts (ANC), elevated total cholesterol (low and high-density lipid), intestinal perforation, and infection. Such adverse events are consistent with those observed following tofacitinib treatment in rheumatoid arthritis (RA) patients (see, for example, J. M. Kremer, et al. The safety and efficacy of a JAK inhibitor in patients with active rheumatoid arthritis: Results of a double-blind, placebo-controlled phase IIa trial of three dosage levels of CP-690,550 versus placebo, Arthritis and Rheumatism 60, 1895-905 (2009)), some of which likely result from either JAK2 dependent inhibition of EPO, TPO and colony stimulating factors (csf-2 and GM-CSF (granulocyte macrophage-colony stimulating factor)) and/or JAK1 dependent inhibition of IL-6. See, Arthritis and Rheumatism 60, 1895-905 (2009), cited above; and O. H. Nielsen, et al., Will novel oral formulations change the management of inflammatory bowel disease? Expert Opinion on Investigational Drugs 25, 709-18 (2016).

In reference to FIG. 1, an orally administered medication can in principle follow the gastro-intestinal tract from the mouth to the esophagus (1), to the stomach (2) through the duodenum (3) to the jejunum (4), then to the ileum (5), and then to the colon (6). The relative absorption areas for such various parts are approximately 60% for the jejunum (4), approximately 26% for the ileum (5), and approximately 13% for the colon (6). Absorption through these various gastro-intestinal regions can lead to the onset of systemic distribution that in turn could lead to undesirable side-effects. The gastro-intestinal tract has a very large surface area. See, for example, H. F. Helander, et al., Surface area of the digestive tract—revisited, Scandinavian Journal of Gastroenterology 49(6), 681-89 (2014); and K. J. Filipski, et al., Intestinal Targeting of Drugs: Rational Design Approaches and Challenges Current Topics in Medicinal Chemistry 13, 776-802 (2013). Such an extensive absorption surface area favors systemic distribution of substances that can go through the walls of the various parts of the intestinal tract and into the blood stream, and in turn have the potential to lead to unwanted side effects of a systemically distributed substance. Systemic distribution is represented by dashed line arrows in FIG. 1 as permeating through the colon walls for simplified illustrative purposes, but such distribution is not limited to the colon walls, for it also can take place through the walls of other parts of the gastrointestinal tract shown in FIG. 1, such as those of the small intestine. It is also understood that the dashed arrow lines in FIG. 1 represent systemic distribution beyond the gastrointestinal track as such systemic distribution is known to take place in reference to the gastrointestinal track physiology, and that such dashed line arrows simply refer in a schematic illustrative manner to such systemic distribution. See, for example, Current Topics in Medicinal Chemistry 13, 777-80 (2013), cited above, for a description of intestinal tissue, transport across the same, and metabolism.

One major reason for attrition in drug candidates is safety and tolerability. See, for example, I. Kola, et al., Can the pharmaceutical industry reduce attrition rates? Nature Reviews Drug Discovery 3, 711-5 (2004); M. J. Waring, et al., An analysis of the attrition of drug candidates from four major pharmaceutical companies. Nature Reviews Drug Discovery 14, 475-86 (2015); M. Hay, et al., Clinical development success rates for investigational drugs, Nature Biotechnology 32, 40-51 (2014); and M. E. Bunnage, Getting pharmaceutical R&D back on target, Nature Chemical Biology 7, 335-9 (2011). Increasing local tissue concentrations of compound to the intended target tissue, while limiting exposure to other tissue, can reduce unwanted side effects. See, for example, V. P. Torchilin, Drug targeting. European Journal of Pharmaceutical Sciences: Official Journal of the European Federation for Pharmaceutical Sciencesll Suppl 2, S81-91 (2000). This concept has widely been accepted for certain diseases and tissues, such as eye (see, for example, R. Gaudana, et al., Ocular drug delivery, The AAPS Journal 12, 348-60 (2010)), skin (see, for example, R. Folster-Holst, et al., Topical hydrocortisone 17-butyrate 21-propionate in the treatment of inflammatory skin diseases: pharmacological data, clinical efficacy, safety and calculation of the therapeutic index, Die Pharmazie 71, 115-21 (2016)), and lung (see, for example, J. S. Patil, et al., Pulmonary drug delivery strategies: A concise, systematic review, Lung India: official organ of Indian Chest Society 29, 44-9 (2012)). Similar to these tissue-targeting approaches, increasing intestinal drug concentrations while limiting unwanted drug levels in other tissue can increase safety margins. See, for example, I. R. Wilding, et al., Targeting of drugs and vaccines to the gut, Pharmacology & Therapeutics 62, 97-124 (1994); D. Charmot, Non-systemic drugs: a critical review, Current Pharmaceutical Design 18, 1434-45 (2012); and Current Topics in Medicinal Chemistry 13, at 780 (2013), cited above. Tissue-selective modulation of targets in the gastrointestinal tissue with compounds achieving limited systemic exposures can potentially improve the therapeutic index of such compounds for the treatment of diseases of the gastrointestinal tract including ulcerative colitis and Crohn's disease. See, for example, O. Wolk, et al., New targeting strategies in drug therapy of inflammatory bowel disease: mechanistic approaches and opportunities, Expert Opin. Drug Deliv. 10(9), 1275-86 (2013). The term "systemic effects" is used herein to refer to systemic exposure and the effects of any such systemic exposure, even though they are not always the same.

Because some known JAK inhibitors have adverse effects that are associated with their systemic effects, it is desirable to find new JAK inhibitors as active substances for the prevention and/or control of excessive inflammatory response and whose systemic effects are eliminated or reduced. It is furthermore desireable to find JAK inhibitors with local effects on gastro-intestinal tissues for the treatment of conditions such as, but not limited to IBD, with reduced systemic effects. Because of the role played by the various JAK proteins, it is furthermore desirable to find pan-JAK inhibitors.

Intestinal tissue targeting can in principle be pursued according to multiple strategies. See, for example, Current Topics in Medicinal Chemistry 13, at 780-95 (2013), cited above, referring to approaches that include physicochemical property approaches, transport-mediated approaches, prodrug approaches, and formulation and technology approaches. It is acknowledged, however, that a "number of challenges and pitfalls exist that are endemic to tissue targeting programs" and in particular to intestinally targeted compounds, as described in Current Topics in Medicinal Chemistry 13, at 795 (2013), cited above.

IBD conditions can extend to multiple parts of the gastrointestinal tract. Even though for simplified illustrative purposes only a colonic disease site (10) is shown in the descending colon in FIG. 1, inflammatory bowel disease may affect any part of the gastrointestinal tract as is the case with Crohn's disease, or in the rectum and colon, as with ulcerative colitis. See, for example, NIDDK (National Institute of Diabetes, and Digestive and Kidney Diseases, National Institutes of Health, US Department of Health and Human Services, <http://spotidoc.com/doc/71780/crohns-disease---national-digestive-diseases-information>, accessed Nov. 29, 2016. IBD disease sites can be, for example, ileal (ileum-located), ileocolic (affecting portions of the ileum and colon), and colonic (located in the colon, as illustratively shown in the descending colon in FIG. 1). So, in certain disease scenarios, a drug delivery along the entire or a large portion of the intestinal tract may be desirable. In other disease scenarios, it may be desirable to increase local concentration at any given portion of the gastrointestinal tract. Still in other scenarios, a combination of these two forms of delivery at different sites in the intestinal tract could be desirable.

One of such scenarios would focus on the delivery of an active substance that has limited systemic effects due to limited absorption when passing through the gastrointestinal tract as exemplified by the solid line arrows in FIG. 1, while being available to act in extensive portions of the gastrointestinal (GI) tract, a feature that is referred to herein as "local GI effects". Because of reduced systemic effects, a wider range of dosages could be evaluated for such substance. It would be further desirable if such active substance had low permeability, so that only a small amount passes through the intestinal wall into the blood stream to limit undesirable adverse side effects when it reaches non-targeted areas.

In addition, JAK inhibitors are envisaged as treatment candidates for other diseases. They are envisaged for use in the treatment of ocular conditions including dry eye (B. Colligris, et al., Recent developments on dry eye disease treatment compounds, Saudi J. Ophthalmol. 28(1), 19-30 (2014)), myeloproliferative neoplasms, myeloproliferative diseases (E. J. Baxter, et al., Acquired mutation of the tyrosine kinase JAK2 in human myeloproliferative disorders, Lancet 365, 1054-1061 (2005); C. James, et al., A unique clonal JAK2 mutation leading to constitutive signalling causes polycythaemia vera, Nature 434, 1144-1148 (2005); R. Kralovics, et al., A gain-of-function mutation of JAK2 in myeloproliferative disorders, N. Engl. J. Med. 352, 1779-1790 (2005); R. L. Levine, et al., Activating mutation in the tyrosine kinase JAK2 in polycythemia vera, essential thrombocythemia, and myeloid metaplasia with myelofibrosis, Cancer Cell 7, 387-397 (2005); G. Wernig, et al., Efficacy of TG101348, a selective JAK2 inhibitor, in treatment of a murine model of JAK2V617F-induced polycythemia vera, Cancer Cell 13, 311-320 (2008)), myeloproliferative syndrome, acute myeloid leukemia, systemic inflammatory response syndrome, systemic onset juvenile rheumatoid arthritis, juvenile idiopathic arthritis (H. W. Li, et al., Effect of miR-19a and miR-21 on the JAK/STAT signaling pathway in the peripheral blood mononuclear cells of patients with systemic juvenile idiopathic arthritis, Exp. Ther. Med. 11(6), 2531-2536 (2016)), type III hypersensitivity reactions, type IV hypersensitivity, inflammation of the aorta, iridocyclitis/uveitis/optic neuritis, juvenile spinal muscular atrophy, diabetic retinopathy, diabetic kidney disease including diabetic nephropathy (F. C. Brosius, et al., JAK inhibition in the treatment of diabetic kidney disease, Diabetologia 59(8), 1624-7, (2016); C. C. Berthier, et al., Enhanced expression of Janus kinase-signal transducer and activator of transcription pathway members in human diabetic nephropathy, Diabetes 58(2), 469-77, (2009); E. N. Gurzov, et al., The JAK/STAT pathway in obesity and diabetes, FEBS J. 283(16), 3002-15 (2016)), microangiopathy, inflammation (M. Kopf, et al., Averting inflammation by targeting the cytokine environment, Nature Reviews Drug Discovery 9, 703-718 (2010); J. J. O'Shea, et al., A new modality for immunosuppression: targeting the JAK/STAT pathway, Nature Rev. Drug Discov. 3, 555-564 (2004)), chronic inflammation, inflammatory bowel disease including ulcerative colitis (UC) and Crohn's disease (R. H. Duerr, et al., A genome-wide association study identifies IL23R as an inflammatory bowel disease gene, Science 314, 1461-1463 (2006); M. Coskun, et al., Involvement of JAK/STAT signaling in the pathogenesis of inflammatory bowel disease, Pharmacol. Res. 76, 1-8 (2013); M. J. Waldner, et al., Master regulator of intestinal disease: IL-6 in chronic inflammation and cancer development, Semin. Immunol.

26(1), 75-9 (2014); S. Danese, et al., JAK inhibition using tofacitinib for inflammatory bowel disease treatment: a hub for multiple inflammatory cytokines, Am. J. Physiol. Gastrointest. Liver Physiol. 310(3), G155-62 (2016); W. Strober, et al., Proinflammatory cytokines in the pathogenesis of inflammatory bowel diseases, Gastroenterology 140, 1756-1767 (2011)), allergic diseases, vitiligo, atopic dermatitis (R. Bissonnette, et al., Topical tofacitinib for atopic dermatitis: a phase IIa randomized trial, Br. J. Dermatol. 175(5), 902-911 (2016); W. Amano, et al., JAK inhibitor JTE-052 regulates contact hypersensitivity by downmodulating T cell activation and differentiation, J. Dermatol. Sci. 84, 258-265 (2016); T. Fukuyama, et al., Topically Administered Janus-Kinase Inhibitors Tofacitinib and Oclacitinib Display Impressive Antipruritic and Anti-Inflammatory Responses in a Model of Allergic Dermatitis, J. Pharmacol. Exp. Ther. 354(3), 394-405 (2015)), alopecia areata (A. K. Alves de Medeiros, et al., JAK3 as an Emerging Target for Topical Treatment of Inflammatory Skin Diseases, PLoS One 11(10) (2016); L. Xing, et al., Alopecia areata is driven by cytotoxic T lymphocytes and is reversed by JAK inhibition, Nat. Med. 20(9), 1043-9 (2014)), dermatitis scleroderma, acute or chronic immune disease associated with organ transplantation (P. S. Changelian, et al. Prevention of organ allograft rejection by a specific Janus kinase 3 inhibitor, Science 302, 875-878 (2003); F. Behbod, et al. Concomitant inhibition of Janus kinase 3 and calcineurin-dependent signaling pathways synergistically prolongs the survival of rat heart allografts, J. Immunol, 166, 3724-3732 (2001); S. Busque, et al, Calcineurin-inhibitor-free immunosuppression based on the JAK inhibitor CP-690,550: a pilot study in de novo kidney allograft recipients, Am. J. Transplant, 9, 1936-1945 (2009)), psoriatic arthropathy, ulcerative colitic arthropathy, autoimmune bullous disease, autoimmune haemolytic anaemia, rheumatoid arthritis (J. M. Kremer, et al., A randomized, double-blind placebo-controlled trial of 3 dose levels of CP-690,550 versus placebo in the treatment of active rheumatoid arthritis, Arthritis Rheum. 54 (annual meeting abstract), L40 (2006); W. Williams, et al, A randomized placebo-controlled study of INCB018424, a selective Janus kinase 1&2 (JAK1&2) inhibitor in rheumatoid arthritis (RA), Arthritis Rheum. 58, 5431 (2008); N. Nishimoto, et al., Study of active controlled monotherapy used for rheumatoid arthritis, an IL-6 inhibitor (SAMURAI): evidence of clinical and radiographic benefit from an x ray reader-blinded randomised controlled trial of tocilizumab, Ann. Rheum. Dis. 66(9), 1162-7 (2007)), rheumatoid arthritis associated interstitial lung disease, systemic lupus erythematosus (A. Goropevšek, et al., The Role of STAT Signaling Pathways in the Pathogenesis of Systemic Lupus Erythematosus, Clin. Rev. Allergy Immunol. (on-line pre-publication) <http://www.docguide.com/role-stat-signaling-pathways-pathogenesis-systemic-lupus-erythematosus?tsid=5> May 23, 2016; M. Kawasaki, et al., Possible role of the JAK/STAT pathways in the regulation of T cell-interferon related genes in systemic lupus erythematosus, Lupus. 20(12), 1231-9 (2011); Y. Furumoto, et al., Tofacitinib ameliorates murine lupus and its associated vascular dysfunction, Arthritis Rheumatol., (on-line pre-publication)<https://www.ncbi.nlm.nih.gov/pubmed/27429362>Jul. 18, 2016)), systemic lupus erythematosus associated lung disease, dermatomyositis/polymyositis associated lung disease, asthma (K. Vale, Targeting the JAK/STAT pathway in the treatment of 'Th2-high' severe asthma, Future Med. Chem. 8(4), 405-19 (2016)), ankylosing spondylitis (AS) (C. Thompson, et al., Anti cytokine therapy in chronic inflammatory arthritis, Cytokine 86, 92-9 (2016)), AS-associated lung disease, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, psoriasis (C. L. *Leonardi*, et al., Efficacy and safety of ustekinumab, a human interleukin-12/23 monoclonal antibody, in patients with psoriasis: 76-week results from a randomised, double-blind, placebo-controlled trial (PHOENIX 1), Lancet 371, 1665-1674 (2008); G. Chan, et al., Dose-dependent reduction in psoriasis severity as evidence of immunosuppressive activity of an oral Jak3 inhibitor in humans, Am. J. Transplant. 6, S87 (2006); K. A. Papp, et al., Efficacy and safety of tofacitinib, an oral Janus kinase inhibitor, in the treatment of psoriasis: a phase 2b randomized placebo-controlled dose-ranging study, Br. J. Dermatol. 167, 668-677 (2012); M. Cargill, et al. A large-scale genetic association study confirms IL12B and leads to the identification of IL23R as psoriasis-risk genes, Am. J. Hum. Genet. 80, 273-290 (2007)), psoriasis type 1, psoriasis type 2, plaque psoriasis, moderate to severe chronic plaque psoriasis, autoimmune neutropaenia, sperm autoimmunity, multiple sclerosis (all subtypes, B. M. Segal, et al., Repeated subcutaneous injections of IL12/23 p40 neutralising antibody, ustekinumab, in patients with relapsing-remitting multiple sclerosis: a phase II, double-blind, placebo-controlled, randomised, dose-ranging study, Lancet Neurol. 7, 796-804 (2008); Z. Yan, et al., Role of the JAK/STAT signaling pathway in regulation of innate immunity in neuroinflammatory diseases, Clin. Immunol. (online pre-publication) <https://www.ncbi.nlm.nih.gov/pubmed/27713030>, accessed Oct. 3, 2016; E. N. Benveniste, et al., Involvement of the janus kinase/signal transducer and activator of transcription signaling pathway in multiple sclerosis and the animal model of experimental autoimmune encephalomyelitis, J. Interferon Cytokine Res. 34(8), 577-88 (2014).; Y. Liu, et al., Therapeutic efficacy of suppressing the Jak/STAT pathway in multiple models of experimental autoimmune encephalomyelitis, J. Immunol. 192(1), 59-72 (2014)), acute rheumatic fever, Sjogren's syndrome, Sjogren's syndrome/disease associated lung disease (T. Fujimura, et al., Significance of Interleukin-6/STAT Pathway for the Gene Expression of REG Iα, a New Autoantigen in Sjögren's Syndrome Patients, in Salivary Duct Epithelial Cells, Clin. Rev. Allergy Immunol. (online pre-publication) <https://www.ncbi.nlm.nih.gov/pubmed/27339601> Jun. 24, 2016), autoimmune thrombocytopaenia, neuroinflammation including Parkinson's disease (Z. Yan, et al., Oct. 3, 2016, cited above). JAK inhibitors have been reported as having therapeutic applications in cancer treatment in addition to inflammatory diseases. (S. J. Thomas, et al., The role of JAK/STAT signaling in the pathogenesis, prognosis and treatment of solid tumors, British J. Cancer 113, 365-71 (2015); A. Kontzias, et al., Jakinibs: A new class of kinase inhibitors in cancer and autoimmune disease, Current Opinion in Pharmacology, 12(4), 464-70 (August 2012); M. Pesu, et al., Therapeutic targeting of JANUS kinases, Immunological Reviews, 223, 132-42 (June 2008); P. Norman, Selective JAK inhibitors in development for rheumatoid arthritis, Expert Opinion on Investigational Drugs, 23(8), 1067-77 (August 2014)). In addition, JAK inhibitors could be useful in the prevention of colorectal cancer because inflammation reduction in the colon could lead to cancer prevention in such organ.

BRIEF SUMMARY OF THE INVENTION

This invention relates to the following compounds:

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide;

2-((1r,4r)-4-(2-(1H-Imidazol-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide;

N-(2-Cyanoethyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-pyran-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((tetrahydro-2H-pyran-4-yl)methyl)acetamide;

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide;

N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide; and pharmaceutically acceptable salts of such compounds, and combinations of them.

The term "compounds of the invention" and "compound of the invention" is intended to encompass at least one compound selected from the above group of compounds, whether in a solvent-free form or in any one of hydrated and/or solvated forms as illustrated herein.

Embodiments of the present invention relate to compounds, pharmaceutical compositions containing them, methods of making and purifying them, methods of using them as JAK inhibitors and methods for using them in the treatment of disease states, disorders, and conditions mediated by JAK.

Embodiments of this invention exhibit pan-JAK inhibition effects with local GI effects and low or negligible systemic effects. Furthermore, embodiments of this invention with such features can be orally administered.

An additional embodiment of the invention is a method of treating a subject suffering from or diagnosed with a disease, disorder, or medical condition mediated by JAK using compounds of the invention or active agents of the invention.

Additional embodiments, features, and advantages of the invention will be apparent from the following detailed description and through practice of the invention.

Figure 1:
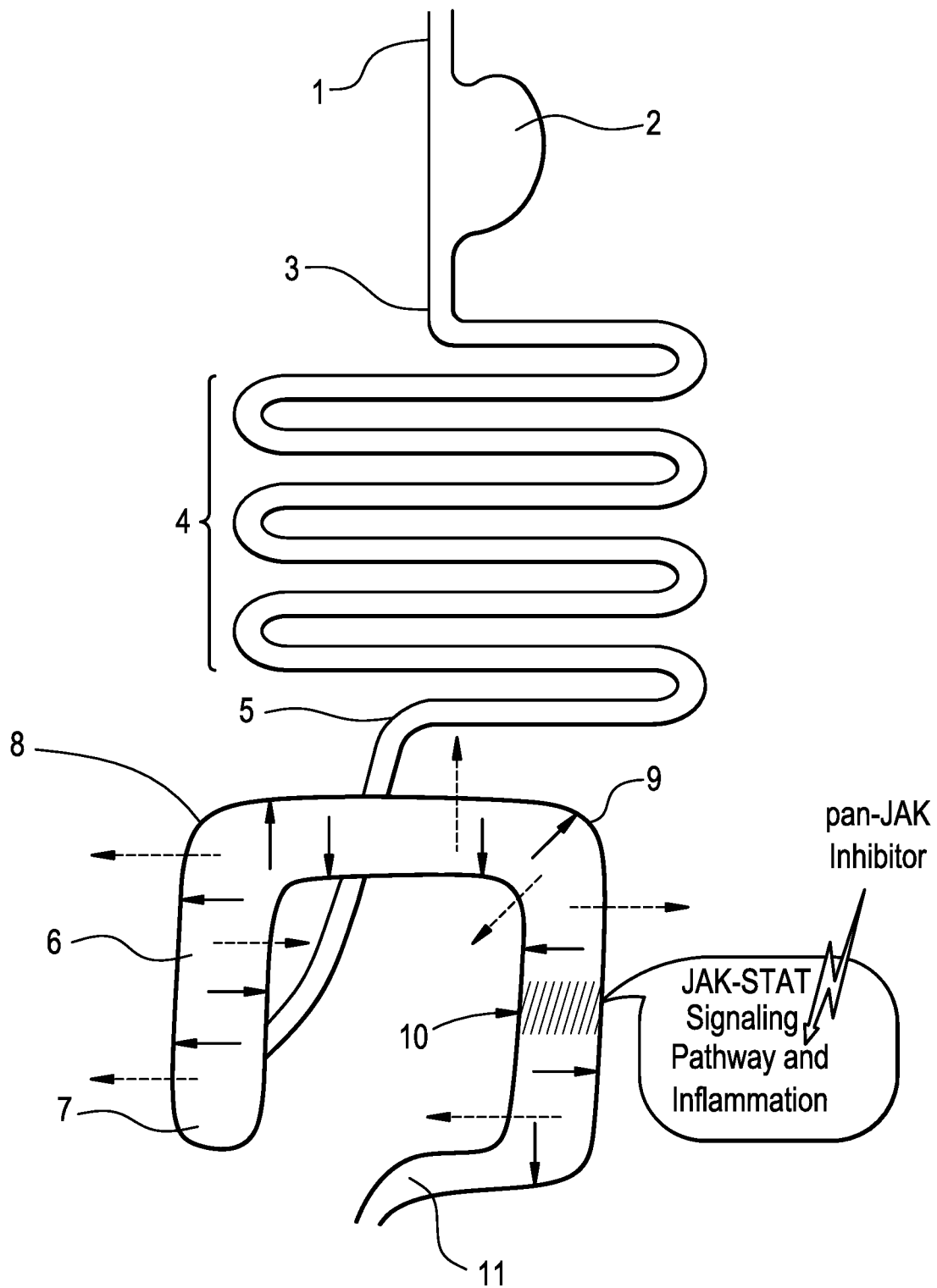
FIG. 1

Schematic diagram of part of the human gastrointestinal tract, shown as a not-at-scale stretched rendering. The duodenum (3), jejunum (4), and ileum (5) (all schematically shown) form the small intestine after the stomach (2) and esophagus (1). The large intestine comprises the colon (6), in turn including the cecum (7) and appendix (not shown), ascending colon, transverse colon, descending colon, sigmoid colon (loop in the same not shown), and rectum (11). The transverse colon is the portion comprised between the right (8) and left (9) colonic flexures, the ascending colon extends from the cecum (7) to the right colonic flexure (8), and the descending colon extends from the left colonic flexure (9) to the rectum (11). Various distribution patterns are illustrated in reference to the colon for convenience, but they can also refer to other parts of the gastrointestinal tract. Systemic distribution is represented by dashed line arrows in FIG. 1 as permeating through the colon walls for simplified illustrative purposes, but such distribution is not limited to the colon walls, for it also can take place through the walls of other parts of the gastrointestinal tract shown in FIG. 1, such as those of the small intestine. Distribution with some tissue penetration is represented by solid line arrows in FIG. 1 as penetrating the colon tissue for simplified illustrative purposes, but such penetration is not limited to the colon tissue, for it also can take place in the tissue of other parts of the gastrointestinal tract shown in FIG. 1, such as the tissue of the small intestine. The effect of an embodiment of a JAK inhibitor according to this invention is illustratively shown as disrupting the JAK/STAT signaling pathway that otherwise would lead to inflammation associated with an inflammatory bowel disease ("IBD"), such as Crohn's disease or ulcerative colitis. By way of example, but not as a limitation, a disease site is illustratively shown as a colonic disease site (10) in the descending colon.

FIG. 2

Schematic diagram showing the preparation/interconversion of embodiments of compound Ex. 1. Embodiments 19-36, 38 and 39 were obtained from embodiment 1s, and embodiments 37 and 40-53 were obtained from embodiment 19, as symbolized in this figure by the dashed line arrow and the legend "19-53" in the box shown in the same.

FIG. 3

Overlay of high throughput X-ray powder diffraction (HT-XRPD) patterns for the following embodiments of compound Ex. 1, from bottom to top: 1s, 2 (obtained by equilibration at room temperature in 1,4-dioxane), 3b (obtained by thermocycling in cyclohexanone), 1b+4 (obtained by cooling crystallization at μL scale in methanol/water (50/50, v/v), 5 (obtained by thermocycling in chloroform), 6 (obtained by cooling crystallization at mL scale in acetonitrile), 7 (obtained of 1 s+7, in turn obtained by solvent equilibration in heptane), 7 (obtained by desolvation of 1 s+7, in turn obtained by solvent equilibration in heptane), 8 (obtained by desolvation of embodiment 5 by cycling differential scanning calorimetry)), and 9 (obtained by desolvation of embodiment 2 by cycling differential scanning calorimetry).

FIG. 4

Overlay of high throughput X-ray powder diffraction (HT-XRPD) patterns for the following embodiments of compound Ex. 1, from bottom to top: is (starting material), la (obtained after exposure to accelerated aging conditions (AAC) (40° C. and 70% relative humidity) several forms of samples of embodiment 1s), 1b (obtained by solvent equilibration at room temperature in toluene), 1c (obtained by cooling crystallization at μL scale in ethyl acetate/1,4-dioxane (50/50, v/v)), 1d (obtained by cooling crystallization at μL scale in acetonitrile/chloroform (50/50, v/v)), 1e (obtained by cooling crystallization at μL scale in ethyl acetate/1,4-dioxane (50/50, v/v)), 1f (obtained by solvent equilibration at room temperature in p-xylene), 1g (obtained by solvent equilibration at 50° C. in anisole), 1h (obtained by cooling crystallization at μL scale in p-xylene).

FIG. 5

Overlay of high throughput X-ray powder diffraction (HT-XRPD) patterns for the following embodiments of compound Ex. 1, from bottom to top: 1s, 3b (obtained by thermocycling in cyclohexanone), 3c (obtained by cooling crystallization at μL scale in 1,4-dioxane), 3d (obtained by cooling crystallization at μL screen in tetrahydrofuran), and 3e (obtained by thermocycling in isobutanol).

FIG. 6

HR-XRPD diffractograms of embodiment 1s in its initial form ("1s"), after a four-day exposure to 40° C. and 70% relative humidity ("1s 70 RH"), and after a four-day exposure to 25° C. and 100% relative humidity (embodiment 10 or "10").

FIG. 7A

X-ray powder diffraction (XRPD) pattern of embodiment 11.

FIG. 7B

X-ray powder diffraction (XRPD) pattern of embodiment 12.

FIG. 7C

X-ray powder diffraction (XRPD) pattern of embodiment 13.

FIG. 7D

X-ray powder diffraction (XRPD) pattern of embodiment 14.

FIG. 7E

X-ray powder diffraction (XRPD) pattern of embodiment 11b.

FIG. 8

Overlay of X-ray powder diffraction (XRPD) patterns for the following embodiments of compound Ex. 1, from bottom to top: embodiment 17, embodiment 18, embodiment 15 and embodiment 16.

FIG. 9

Modulated DSC ("mDSC") profile for embodiment 19 showing a glass transition point ($T_g$) at 115.3° C. ("Rev" in the ordinate axis label refers to "reversible").

FIG. 10A

TGA (thermogravimeteric analysis) of embodiment 18 showing a 6.5% w/w loss between 30° C. and 170° C.

FIG. 10B

DSC (differential scanning calorimetry) of embodiment 18 showing an endotherm of 52.8 J/g between 45° C. and 90° C., an endotherm of 31.0 J/g at 140.6° C., an exotherm of 24.3 J/g at 168.8° C., and an endotherm of 31.3 J/g at 200.0° C.

FIG. 11

Overlay of X-ray powder diffraction (XRPD) patterns for the following embodiments of compound Ex. 1, from bottom to top: embodiment 20 and embodiment 21.

FIG. 12A

TGA of embodiment 17 showing a 4.2% w/w loss between 30° C. and 100° C.

FIG. 12B

DSC of embodiment 17 showing an endotherm of 90.3 J/g between 45° C. and 100° C., an endotherm of 35.5 J/g at 143.8° C., an endotherm of 1.6 J/g at 168.3° C., an exotherm of 3.8 J/g at 178° C., and an endotherm of 9.2 J/g at 200.0° C.

FIG. 13

Overlay of X-ray powder diffraction (XRPD) patterns for the following embodiments of compound Ex. 1, from bottom to top: embodiment 31, embodiment 30, embodiment 17, embodiment 29, embodiment 16, embodiment 26, embodiment 25, embodiment 18, embodiment 24, embodiment 23, embodiment 27 and embodiment 22.

FIG. 14

Overlay of X-ray powder diffraction (XRPD) patterns for the following embodiments of compound Ex. 1, from bottom to top: embodiment 32, embodiment 33, embodiment 23, embodiment 34, embodiment 35, embodiment 36, embodiment 25, embodiment 38, embodiment 17, embodiment 39 and embodiment 28.

FIG. 15

Overlay of X-ray powder diffraction (XRPD) patterns for the following embodiments of compound Ex. 1, from bottom to top: embodiment 46, embodiment 45, embodiment 44, embodiment 43, embodiment 42, embodiment 41, embodiment 40 and embodiment 37.

FIG. 16

Overlay of X-ray powder diffraction (XRPD) patterns for the following embodiments of compound Ex. 1, from bottom to top: embodiment 53, embodiment 52, embodiment 51, embodiment 50, embodiment 49, embodiment 48 and embodiment 47.

FIG. 17A

TGA of embodiment 11 showing a 4.7% w/w loss between 155° C. and 185° C.

FIG. 17B

DSC of embodiment 11 showing a first endotherm of 57.8 J/g at 167.8° C. due to solvent loss and a second endotherm of 90.8 J/g at 194.5° C. due to sample melt.

FIG. 18

Gravimetric Vapor Sorption (GVS) isotherm plot of embodiment 11 showing a mass change of 0.66% between 0-90% RH. The mass change on the ordinate axis is in reference to the mass of the starting sample.

FIG. 19A

TGA of embodiment 6 showing weight loss at temperatures above 260° C., which weight loss is interpreted as being associated with sample degradation.

FIG. 19B

DSC of embodiment 6 showing an endotherm of 95.8 J/g at 194.4° C. due to sample melt.

FIG. 20A

TGA of embodiment 8 showing a 1.4% w/w loss between 40° C. and 240° C., which corresponds to a loss of 0.07 mol of 1,4-dioxane.

FIG. 20B

DSC of embodiment 8 showing an endotherm of 58.6 J/g at 199.7° C. due to sample melt.

FIG. 21A

TGA of embodiment 2 showing a 7.4% w/w loss between 75° C. and 110° C., a 11.9% w/w loss between 110° C. and 130° C., a 2.0% w/w loss between 130° C. and 165° C., and a 2.5% w/w loss between 165° C. and 210° C.

FIG. 21B

DSC of embodiment 2 showing an endotherm of 86.2 J/g at 92.8° C., an endotherm of 11.1 J/g at 111.5° C., an endotherm of 45.5 J/g at 149.0° C., an exotherm of 20.6 J/g at 165.2° C., an endotherm of 3.7 J/g at 177.1° C., an endotherm of 43.0 J/g at 200.2° C., and an endotherm of 29.3 J/g at 220.6° C.

FIG. 22A

TGA of embodiment 9.

FIG. 22B

DSC of embodiment 9 showing an endotherm of 104.4 J/g at 221.8° C.

FIG. 23A

TGA of embodiment 16 showing a 5.2 w/w loss between 30° C. and 105° C.

FIG. 23B

DSC of embodiment 16 showing an endotherm of 48.4 J/g between 35° C. and 90° C., an endotherm of 41.8 J/g at 147.0° C., an endotherm of 1.0 J/g at 166.6° C., an exotherm of 4.4 J/g at 180.7° C., and an endotherm of 7.7 J/g at 201.1° C.

FIG. 24

X-ray powder diffraction (XRPD) of embodiment 11 (labeled "11") and X-ray powder diffraction (XRPD) of embodiment 11 after the variable temperature (VT)-XRPD experiment (labeled "11 post VT"), and X-ray powder diffraction (XRPD) of embodiment 6.

DETAILED DESCRIPTION OF THE INVENTION

As used herein, the terms "including", "containing" and "comprising" are used in their open, non-limiting sense.

Any formula given herein is intended to represent compounds having structures depicted by the structural formula as well as certain variations or forms. Certain structures may exist as tautomers. Additionally, an amorphous form, hydrates, solvates, polymorphs and pseudopolymorphs of such compounds of this invention, and mixtures thereof, are also envisaged as parts of this invention. Embodiments of this invention are in a solvent-free form or in any one of hydrated and/or solvated forms as illustrated herein.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, and oxygen such as $^2$H, $^3$H, $^{11}$C, $^{13}$C, $^{14}$C, $^{15}$N, $^{18}$O, and $^{17}$O, respectively. Such isotopically labeled compounds are useful in metabolic studies (preferably with $^{14}$C), reaction kinetic studies (with, for example deuterium (i.e., D or $^2$H); or tritium (i.e., T or $^3$H)), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased local in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

"Tautomers" refer to compounds that are interchangeable forms of a particular compound structure, and that vary in the displacement of hydrogen atoms and electrons. Thus, two structures that have an H member in different positions may be in equilibrium while satisfying valency rules. For example, enols and ketones are tautomers because they are rapidly interconverted by treatment with either acid or base.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^{1example}$ is $S_2$ and $S^2_{example}$ is $S_3$;

$S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The following JAK inhibitors are illustrative embodiments of the invention:

2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide;

2-((1r,4r)-4-(2-(1H-Imidazol-4-yl)imidazo[4,5-d]pyrrolo[2,3-b]pyridin-1(6H)-yl)cyclohexyl)acetonitrile;

2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide;

N-(2-Cyanoethyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(tetrahydro-2H-pyran-4-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((tetrahydro-2H-pyran-4-yl)methyl)acetamide;

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide;

2-(1-((1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide;

N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide;

2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide; and 2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide.

Additional embodiments of the invention are pharmaceutically acceptable salts of compounds given above.

Additional embodiments of the invention are pharmaceutical compositions each comprising an effective amount of at least one of the compounds given above or a pharmaceutically acceptable salt thereof.

A "pharmaceutically acceptable salt" is a salt of a compound that is non-toxic, biologically tolerable, or otherwise biologically suitable for administration to the subject. See, generally, S. M. Berge, et al., "Pharmaceutical Salts", J. Pharm. Sci. 66, 1-19 (1977), and Handbook of Pharmaceutical Salts, Properties, Selection, and Use, Stahl and Wermuth, Eds., Wiley-VCH and VHCA, Zurich, 2002. Compounds of the invention may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methane-sulfonates, propanesulfonates, naphthalene-1-sulfonates, naphthalene-2-sulfonates, and mandelates.

If the compound of the invention contains at least one basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, and phosphoric acid, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Not all the embodiments of pharmaceutically acceptable salts of compounds according to this invention may be equally suitable for their development, for compounds that are sufficiently weakly basic (e.g., pKa of about 4) might not form sufficiently stable salts for development purposes. See, e.g., G. A. Stephenson, et al., J. Pharm. Sciences 100(5), 1607-17 (2011) "Physical stability of salts of weak bases in the solid state". Some embodiments of this invention are envisaged to encompass co-crystallized forms of a compound according to this invention with a suitable co-crystal former. Design and properties of co-crystals for pharmaceutical use and methods of making and characterizing them have been given in, for example, N. Shan, et al., Drug Discovery Today, 13(9/10), 440-46 (2008) "The role of cocrystals in pharmaceutical science"; N. Qiao, et al., Intl. J. Pharmaceutics, 419, 1-11 (2011) "Pharmaceutical cocrystals: An overview"; R. Thakuria, et al., Intl. J. Pharmaceutics, 453, 101-25 (2013) "Pharmaceutical cocrystals and poorly soluble drugs".

The compounds of the invention, including their pharmaceutically acceptable salts, whether alone or in combination, (collectively, "active agent" or "active agents") are useful as JAK inhibitors in the methods of the invention. Such methods for modulating JAK activity comprise exposing JAK to an effective amount of at least one chemical compound of the invention.

In some embodiments, the JAK inhibitor is used in a subject diagnosed with or suffering from a disease, disorder, or medical condition mediated through JAK activity, such as those described herein. Symptoms or disease states are intended to be included within the scope of "diseases, disorders or medical conditions."

Accordingly, the invention relates to methods of using the active agents described herein to treat subjects diagnosed with or suffering from a disease, disorder, or medical condition mediated through JAK. The term "treat" or "treating" as used herein is intended to refer to administration of an active agent or composition of the invention to a subject for the purpose of affecting a therapeutic or prophylactic benefit through modulation of JAK. Treating includes reversing, ameliorating, alleviating, inhibiting the progress of, lessening the severity of, reducing, or preventing a disease, disorder, or condition, or one or more symptoms of such disease, disorder or condition mediated through modulation of JAK activity. The term "subject" refers to a mammalian patient in need of such treatment, such as a human. The term "inhibitors" or "inhibitor" refers to compounds that decrease, prevent, inactivate, desensitize or down-regulate JAK expression or activity.

Embodiments of this invention provide JAK inhibitors for the prevention and/or control of excessive inflammatory response. Embodiments of JAK inhibitors according to this invention are pan-JAK inhibitors.

Unless indicated otherwise, the term "JAK inhibitor physico-chemical properties" refers to the corresponding named properties as follows:
 as given in the description for compounds Ex. 1-12, in the case of molar masses;
 as determined according to the respective definitions, in the case of numbers of H bond donors, acceptors and rotatable bonds; and
 as measured in reference to Table 1a, column 2, in case of plasma concentrations, and Table 7, columns 3 and 4, in case of the A-B permeability coefficients in the presence of P-gp inhibitor and B-A permeability coefficients.

Embodiments of this invention provide methods of inhibiting JAK, comprising exposing a JAK receptor to a JAK inhibitor that is characterized by having the following JAK inhibitor physico-chemical properties: a plasma concentration in the range from about 0.1 ng/mL to about 60 ng/mL, cLog P in the range from about 0.1 to about 2.8, A-B permeability coefficients in the presence of a P-gp inhibitor in the range from about 0.1 to about 2.5, B-A permeability coefficients in the range from about 0.5 to about 20, tPSA in the range from about 85 to about 120.

In other embodiments of methods of inhibiting JAK according to this invention, the plasma concentration is in the range from about 10 ng/mL to about 20 ng/mL.

In other embodiments of methods of inhibiting JAK according to this invention, cLogP is in the range from about 0.8 to about 1.4.

In other embodiments of methods of inhibiting JAK according to this invention, the A-B permeability coefficient in the presence of a P-gp inhibitor is in the range from about 0.6 to about 1.5.

In other embodiments of methods of inhibiting JAK according to this invention, the B-A permeability coefficient is in the range from about 0.5 to about 5.

In other embodiments of methods of inhibiting JAK according to this invention, the tPSA is in the range from about 100 to about 120.

Further embodiments of this invention provide methods of inhibiting JAK, comprising exposing a JAK receptor to a JAK inhibitor that is further characterized by having the following JAK inhibitor physico-chemical properties: A molar mass in the range from about 300 g mol$^{-1}$ to about 500 g mol$^{-1}$, a number of hydrogen bond donors in the range from about 2 to about 3, a number of hydrogen bond acceptors in the range from about 4 to about 5, and a number of rotatable bonds in the range from about 3 to about 6, in addition to the plasma concentrations, clogP values, permeability coefficients, and tPSA values described above for methodologies of inhibiting JAK according to this invention.

In other embodiments of methods of inhibiting JAK according to this invention, the molar mass is in the range from about 340 g mol$^{-1}$ to about 430 g mol$^{-1}$.

In other embodiments of methods of inhibiting JAK according to this invention, the number of rotatable bonds is in the range from about 5 to about 6.

Embodiments of this invention provide methods for treating inflammation in the gastrointestinal tract of a subject, comprising administering to a subject a pharmaceutically effective amount of a JAK inhibitor that is characterized by having the following JAK inhibitor physico-chemical properties: A plasma concentration in the range from about 0.1 ng/mL to about 60 ng/mL, cLog P in the range from about 0.1 to about 2.8, A-B permeability coefficients in the presence of a P-gp inhibitor in the range from about 0.1 to about 2.5, B-A permeability coefficients in the range from about 0.5 to about 20, tPSA in the range from about 85 to about 120.

In other embodiments of methods of treating inflammation in the gastrointestinal tract according to this invention, the plasma concentration is in the range from about 10 ng/mL to about 20 ng/mL.

In other embodiments of methods of treating inflammation in the gastrointestinal tract according to this invention, cLogP is in the range from about 0.8 to about 1.4.

In other embodiments of methods of treating inflammation in the gastrointestinal tract according to this invention, the A-B permeability coefficient is in the presence of a P-gp inhibitor is in the range from about 0.6 to about 1.5.

In other embodiments of methods of treating inflammation in the gastrointestinal tract according to this invention, the B-A permeability coefficient is in the range from about 0.5 to about 5.

In other embodiments of methods of treating inflammation in the gastrointestinal tract according to this invention, the tPSA is in the range from about 100 to about 120.

Further embodiments of this invention provide methods for treating inflammation in the gastrointestinal tract of a subject wherein the JAK inhibitor physico-chemical properties are further characterized by having the following JAK inhibitor physico-chemical properties: A molar mass in the range from about 300 g mol$^{-1}$ to about 500 g mol$^{-1}$, a number of hydrogen bond donors in the range from about 2 to about 3, a number of hydrogen bond acceptors in the range from about 4 to about 5, and a number of rotatable bonds in the range from about 3 to about 6, in addition to the plasma concentrations, cLogP values, permeability coefficients, and tPSA values described above for methodologies of treating inflammation according to this invention.

In other embodiments of methods of treating inflammation in the gastrointestinal tract according to this invention, the molar mass is in the range from about 350 g mol$^{-1}$ to about 430 g mol$^{-1}$.

In other embodiments of methods of treating inflammation in the gastrointestinal tract according to this invention, the number of rotatable bonds is in the range from about 5 to about 6.

Embodiments of JAK inhibitors according to this invention have the following JAK physico-chemical properties: a plasma concentration in the range from about 0.1 ng/mL to about 60 ng/mL, a cLogP in the range from 0.1 to about 2.8, an A-B permeability coefficient in the presence of a P-gp inhibitor in the range from about 0.1 to about 2.5, a B-A permeability coefficient in the range from about 0.5 to about 20, and a tPSA in the range from about 85 to about 120.

Further embodiments of JAK inhibitors according to this invention have a plasma concentration is in the range from about 10 ng/mL to about 20 ng/mL.

Further embodiments of JAK inhibitors according to this invention have cLogP values in the range from about 0.8 to about 1.4.

Further embodiments of JAK inhibitors according to this invention have A-B permeability coefficient in the presence of a P-gp inhibitor in the range from about 0.6 to about 1.5.

Further embodiments of JAK inhibitors according to this invention have B-A permeability coefficient in the range from about 0.5 to about 5.

Further embodiments of JAK inhibitors according to this invention have tPSA values in the range from about 100 to about 120.

Other embodiments of JAK inhibitors according to this invention have the following JAK inhibitor physico-chemical properties: A molar mass in the range from about 300 g mol$^{-1}$ to about 500 g mol$^{-1}$, a number of hydrogen bond donors in the range from about 2 to about 3, a number of hydrogen bond acceptors in the range from about 4 to about 5, and a number of rotatable bonds in the range from about 3 to about 6 in addition to the plasma concentrations, cLogP values, permeability coefficients, and tPSA values described above for JAK inhibitors according to this invention.

Further embodiments of JAK inhibitors according to this invention have a molar mass is in the range from about 350 g mol$^{-1}$ to about 430 g mol$^{-1}$.

Further embodiments of JAK inhibitors according to this invention have a number of rotatable bonds is in the range from about 5 to about 6.

In treatment methods according to the invention, an effective amount of at least one active agent according to the invention is administered to a subject suffering from or diagnosed as having such a disease, disorder, or medical condition. An "effective amount" means an amount or dose sufficient to generally bring about the desired therapeutic or prophylactic benefit in patients in need of such treatment for the designated disease, disorder, or medical condition. Effective amounts or doses of the active agents of the present invention may be ascertained by methods such as modeling, dose escalation studies or clinical trials, and by taking into consideration factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units.

Embodiments of this invention are new JAK inhibitors as active substances for the prevention and/or control of excessive inflammatory response and whose systemic effects are eliminated or reduced. Further embodiments of this invention are JAK inhibitors with local effects on gastro-intestinal tissues for the treatment of conditions such as, but not limited to, IBD, without causing systemic effects or with such systemic effects acceptably reduced.

Embodiments of this invention are low permeability JAK inhibitors. Further embodiments of this invention are JAK inhibitors that have aqueous solubility.

Once improvement of the patient's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases mediated by JAK activity, such as another JAK inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect the activity of at least one of the JAK family of proteins. Measuring the activity of the target may be performed by analytical methods.

The active agents of the invention are envisaged for use, alone or in combination with one or more additional active ingredients, to formulate pharmaceutical compositions of the invention. A pharmaceutical composition of the invention comprises an effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, subcutaneous injection, topical administration, or oral administration. Preferably, the compositions may be formulated for oral administration.

For oral administration, the active agents of the invention can be provided in the form of tablets, capsules, or beads, or as a solution, emulsion, or suspension. To prepare the oral compositions, the active agents may be formulated to yield a dosage of, e.g., for a 70-kg human, from about 1 to 1000 mg/day in single or multiple dosage units as an illustrative range.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Liquid oral excipients include ethanol, glycerol, water, and the like. Starch, polyvinyl-pyrrolidone (PVP), sodium starch glycolate, microcrystalline cellulose, and alginic acid are disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating. Additional coating that may be used include coatings that are designed to release the compound or active agent as a function of time, pH or bacterial content.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Soft gelatin capsules may be prepared by mixing the active ingredient with an oil such as peanut oil or olive oil, liquid paraffin, a mixture of mono and di-glycerides of short chain fatty acids, polyethylene glycol 400, or propylene glycol. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to effect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or medical condition mediated by JAK, comprising administering to the subject in need of such treatment an effective amount of the active agent.

In certain embodiments of the inventive method, the disease, disorder, or medical condition is an inflammatory bowel disease, such as Crohn's disease and ulcerative colitis.

Other embodiments of this invention provide for a method for modulating JAK activity, including when such kinase is in a subject, comprising exposing JAK to an effective amount of at least one compound selected from compounds of the invention.

The compounds of the invention are useful as JAK inhibitors that can be dosed orally and specifically distribute to intestinal tissue while maintaining low systemic exposures. This is in contrast to most known JAK inhibitors which are dosed orally and distribute to many tissues due to the fact that they have extensive systemic exposure.

Table 1a and Table 1b show results of in vivo experiments. These results comprise plasma and colon tissue concentrations for fifteen compounds that had been administered to mice as described in Protocols 1, 2 or 3. Plasma and colon concentration results were obtained by following Protocol 1 using venipuncture of dorsal metatarsal vein bleed for Compounds (B), (C), and Examples 6 and 11. Plasma and colon concentration results were obtained by following Protocol 2 using retro-orbital bleed for Compounds (A), and Examples 1, and 3-5 and Protocol 2 using venipuncture of the dorsal metatarsal vein for Examples 2, 7-10, and 12. The results of Protocols 1 and 2 are shown in Table 1a. Plasma and colon concentration results were obtained by following Protocol 3 for Examples 1, 3 and 4. The results of Protocol 3 are shown in Table 1b. These protocols are described below under the heading In vivo Studies.

TABLE 1a

Results of In Vivo Experiments After p.o. Dosing - Mean Concentration of Test Compounds

| Test Compound | Plasma Concentration After p.o. Dosing (ng/mL) | | | | | | Colon Concentration After p.o. Dosing (ng/g) | |
|---|---|---|---|---|---|---|---|---|
| | Time = 0.5 h | | Time = 2 h | | Time = 4 h | | Time = 4 h | |
| | Mean* | Standard Deviation | Mean* | Standard Deviation | Mean* | Standard Deviation | Mean* | Standard Deviation |
| A | 347.0 | 78.5 | 69.1 | 40.8 | 84.5 | 25.5 | 895.0 | 260.6 |
| B | 352.7 | 85.7 | 66.3 | 26.2 | 11.3 | 3.7 | 6076.7 | 3125.8 |
| C | 547.0 | 71.4 | 130.2 | 63.7 | 16.7 | 5.9 | 7776.7 | 3500.2 |
| Ex. 1 | 13.4 | 1.5 | 6.1 | 3.7 | 3.3 | 1.2 | 8591.7 | 10245.7 |
| Ex. 2 | 24.5 | 3.6 | 4.2 | 1.8 | 1.3 | 0.1 | 7600.0 | 983.6 |
| Ex. 3 | 41.4 | 15.1 | 3.9 | 0.7 | 1.5** | *** | 2147.2 | 1821.6 |
| Ex. 4 | 12.9 | 1.6 | 7.5 | 2.8 | 3.3 | 1.5 | 4448.3 | 989.3 |
| Ex. 5 | 31.9 | 5.1 | 8.8 | 1.7 | 6.0 | 1.2 | 5328.3 | 986.0 |
| Ex. 6 | 18.8 | 20.6 | 3.0 | 0.9 | 1.7# | ## | 11706.7 | 11305.2 |
| Ex. 7 | 47.0 | 3.8 | 9.6 | 4.4 | 5.0 | 1.2 | 12008.3 | 9461.1 |
| Ex. 8 | 43.1 | 8.7 | 5.4 | 0.6 | 2.6 | 0.6 | 7396.7 | 3037.3 |
| Ex. 9 | 15.1 | 1.8 | 6.2 | 4.5 | 3.9 | 0.9 | 7683.3 | 230.9 |
| Ex. 10 | 26.6 | 4.0 | 3.2 | 1.0 | 3.1 | 0.7 | 3005.0 | 1347.2 |
| Ex. 11 | 1.6** | *** | ^ | ^^ | ^ | ^^ | 4785.0 | 1059.9 |
| Ex. 12 | 15.6 | 8.7 | 4.2 | 1.4 | 2.3 | 1.0 | 5885.0 | 3154.1 |

*Mean calculated from the values obtained from three mice unless otherwise noted.
**Mean was calculated with values obtained from two mice as the values obtained from the third mouse were below the lower limit of quantitation.
***No standard deviation calculated as the mean was calculated from only two values.
Mean given as the value obtained from one mouse as the values obtained from the second and third mice were below the lower limit of quantitation.
No standard deviation calculated in light of note # in this table.
^Mean was not calculated as the values for all three mice were below the lower limit of quantitation.
^^No standard deviation calculated in light of note ^ in this table.

TABLE 1b

Results of In Vivo Experiments After i.c. Dosing - Mean Concentration of Test Compounds

| Test Compound | Plasma Concentration After i.c. Dosing (ng/mL) | | | | | | Colon Concentration After i.c. Dosing (ng/g) | |
|---|---|---|---|---|---|---|---|---|
| | Time = 0.5 h | | Time = 2 h | | Time = 4 h | | Time = 4 h | |
| | Mean* | Standard Deviation | Mean* | Standard Deviation | Mean* | Standard Deviation | Mean* | Standard Deviation |
| Ex. 1 | 2.5# | ## | ^ | ^^ | ^ | ^^ | 681.0 | 437.0 |
| Ex. 3 | 1.5# | ## | ^ | ^^ | ^ | ^^ | 227.8 | 254.1 |
| Ex. 4 | 3.8** | *** | 2.5# | ## | ^ | ^^ | 26.1# | ## |

*Mean calculated from the values obtained from three mice unless otherwise noted.
**Mean was calculated with values obtained from two mice as the values obtained from the third mouse were below the lower limit of quantitation.
***No standard deviation calculated as the mean was calculated from only two values.
Mean given as the value obtained from one mouse as the values obtained from the second and third mice were below the lower limit of quantitation.
No standard deviation calculated in light of note # in this table.
^Mean was not calculated as the values for all three mice were below the lower limit of quantitation.
^^No standard deviation calculated in light of note ^ in this table.

Compounds (A)-(C) are the following reference compounds that have been disclosed in WO2013/007765 or WO2011/086053 for their use as inhibitors of Janus kinases:

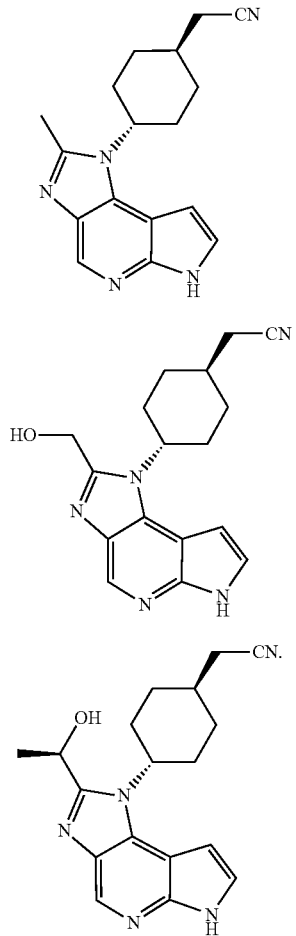

Compounds Ex. 1-12 in Tables 1a and 1b are embodiments of this invention given in the respective Examples.

As evinced in Table 1a, colon concentrations for compounds Ex. 1-12 were found to be much higher than the respective plasma concentrations, with [colon (4 h)]: [plasma (0.5 h)] concentration ratios ranging from about 52 to about 3,000. In contrast, such ratios for compounds (A)-(C) ranged from about 3 to about 17. Table 1b also provides supportive data that Examples 1, 3 and 4 have low systemic exposures after i.c. dosing. The contrast between properties of embodiments of this invention with respect to reference compounds is much more accentuated when the comparison is referred to the 4 h plasma concentration values. In this regard, the [colon (4 h)]: [plasma (4 h)] concentration ratios for compounds Ex. 1-12 range from about 888 to about 6886. In contrast, such ratios for compounds (A)-(C) range from about 11 to about 538. These colon-to-plasma concentration ratios are indicative of compounds Ex. 1-12 having low systemic effects at any time post oral dose, while compounds (A)-(C) have comparatively high systemic effects. This is an unexpected finding of local GI effects for compounds Ex. 1-12.

As shown in Table 4, the enzymatic activity of compounds Ex. 1-12 was measured to determine activity for each individual enzyme. For all compounds tested, there was measured inhibition of enzyme activity, demonstrating that these compounds are pan-JAK inhibitors. The data given in this table for compounds (A)-(C) also demonstrate inhibition of enzyme activity for all JAK proteins by these compounds.

As shown in Table 5, the cellular activities of compounds Ex. 1-12 were assessed in peripheral blood mononuclear cell (PBMC) using stimuli IL-2, IFN-α, and GM-CSF and measuring inhibition of phosphorylation of STAT5, STAT4, and STAT5, respectively. For all compounds tested, there was measured inhibition of STAT phosphorylation with all three stimuli.

As shown in Table 6, the solubilities of compounds Ex. 1-12 were measured in simulated gastric fluid ("SGF") and simulated intestinal fluid ("SIF"). All compounds tested showed measurable solubility above 400 μM in SGF, and in the range of 81 μM to above 400 μM with SIF. As shown in the same table, these solubility data were comparable to the solubilities of compounds (A)-(C).

As shown in Table 7, the permeability of compounds (A)-(C) and Ex. 1-12 was measured using MDCK-MDR1 cell line with and without elacridar, a P-gp inhibitor. All compounds demonstrated low permeability for apical-to-basolateral transport measurements, with and without P-gp inhibitor (elacridar). The permeability coefficient values for compounds (A)-(C) and Ex. 1-12 were low and comparable for apical-to-basolateral transport without elacridar (for all such compounds) and with elacridar (for compounds (B)-(C) and compounds Ex. 1-12) (columns 2 and 3 in such table), but the basolateral-to-apical permeability coefficients for compounds (A)-(C) were greater than those for most of the compounds Ex. 1-12, as shown in column 4 of the same table. In reference to columns 3 and 4 in Table 7, most of compounds Ex. 1-12 have low apical-to-basolateral permeability coefficients measured in the presence of elacridar (column 3), and also low basolateral-to-apical permeability coefficients (column 4). These two features characterize such compounds as being low permeability compounds. The same characterization cannot be made for compounds (A)-(C), whose basolateral-to-apical permeability coefficients (column 4) are greater than those for most of the compounds Ex. 1-12. Efflux ratios given in the same table for compounds (A)-(C) and Ex. 1-12 show that all these compounds are P-gp substrates.

There is no known reference teaching or suggestion indicating that the marked lack of systemic effects for embodiments of this invention in comparison with those of reference compounds (A)-(C) can be inferred and/or predicted on the basis of structural comparisons or other features of compounds (A)-(C) such as those discussed in reference to Tables 4, 6 and 7 This is so even though reference compounds (A)-(C) present structural similarities of certain moieties with similar moieties of embodiments of this invention.

In addition, there is no known reference teaching or suggestion indicating that the low permeability feature for embodiments of this invention in comparison with those of reference compounds (A)-(C) can be inferred and/or predicted on the basis of structural comparisons.

The following specific examples are provided to further illustrate the invention and various embodiments.

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using Merck silica gel 60 $F_{254}$ 2.5 cm×7.5 cm, 250 µm or 5.0 cm×10.0 cm, 250 µm pre-coated silica gel plates.

Normal-phase flash column chromatography (FCC) was performed on silica gel ($SiO_2$) eluting with 2 M $NH_3$ in MeOH/DCM, unless otherwise noted.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated by either ChemDraw (CambridgeSoft, Cambridge, Mass.) or ACD/Name Version 9 (Advanced Chemistry Development, Toronto, Ontario, Canada). By way of example, the designation (1r,4r) refers to the trans orientation around the cyclohexyl ring as generated using the naming function of Chemdraw Ultra Pro 14.0.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

Experiments such as TGA, DSC, GVS typically show slight variability in the data presented based on the individual samples that are being analyzed and slight variations in hydration and/or amount of solvent present.

The TGA plots for individual embodiments are shown in terms of temperature in ° C. on the X-axis and weight loss in % on the Y-axis.

The DSC plots for individual embodiments are shown in terms of temperature in ° C. on the X-axis and heat flow in W/g on the Y-axis. The DSC heating rate was 10° C./min. Integrations of endothermic and exothermic events provide the energy absorbed (for an endothermic event) or energy released (for an exothermic event) in J/g. Dashed lines shown going across the trace represent the area that was integrated.

In the figures where the term "Exo Up" is present, an endothermic event is reflected by a curve that goes down and an exotherm event is reflected by a curve that goes up.

Some diffractograms have been presented in an overlay arrangement of diffractograms that are separated by spacings to allow visualization. Each of the diffractograms is referenced to a zero relative intensity that is the intersection of each of such diffractograms with the ordinate axis or to the lowest relative intensity reading of each of such diffractograms.

Figures that display a plurality of XPRD patterns for any single embodiment reflect different patterns obtained for samples of such embodiment that were nevertheless prepared with the same method in different solvents.

Abbreviations and acronyms used herein include the following as shown below:

Abbreviations and acronyms defined

| Acronym | Term |
| --- | --- |
| AAC | Accelerated aging conditions (40° C. and 70% RH) |
| ACN | Acetonitrile |
| aq | Aqueous |
| br | Broad |
| cLogP | Calculated logP |
| DCM | Dichloromethane |
| DIPEA, DIEA, or Hunig's base | Diisopropylethylamine |
| DMA | Dimethylacetamide |
| DMF | N,N-Dimethylformamide |
| DMPU | 1,3-Dimethyl-3,4,5,6-tetrahydro-2(1H)-pyrimidinone |
| DMSO | Dimethyl sulfoxide |
| DSC | Differential Scanning Calorimetry |
| EtOAc, or EA | Ethyl Acetate |
| EtOH | Ethanol |
| ESI | Electrospray ionization |
| FCC | Normal-phase silica gel flash column chromatography |
| g | Gram(s) |
| GVS | Gravimetric Vapor Sorption |
| h | Hour(s) |
| HPLC | High-pressure liquid chromatography |
| HR-XRPD | High resolution X-ray powder diffraction |
| HT-XRPD | High throughput X-ray powder diffraction |
| IPA | isopropanol |
| i.c. | Intra-colonic |
| Hz | Hertz |
| LCMS | Liquid chromatography and mass spectrometry |
| M | Molar |
| mDSC | Modulated Differential Scanning Calorimetry |
| m/z | Mass to charge ratio |
| MeOH | Methanol |
| mg | Milligram(s) |
| min | Minute(s) |
| mL | Milliliter(s) |
| µL | Microliter(s) |
| Acronym | Term |
| mmol | Millimole(s) |
| MTBE | Methyl tert-butyl ether |
| MS | Mass spectrometry |
| NMR | Nuclear magnetic resonance |
| p.o. | per os or by mouth |
| ppm | Parts per million |
| PTFE | polytetrafluoroethylene |
| PyBOP | Benzotriazol-1-yl-oxytripyrrolidinophosphonium hexafluorophosphate |
| PyBrOP | Bromotripyrrolidinophosphonium hexafluorophosphate |
| RH | Relative humidity |
| Rt | Retention time |
| Rt or RT | Room temperature |
| TFA | Trifluoroacetic acid |
| TGA | Thermogravimeteric Analysis |
| THF | Tetrahydrofuran |
| TLC | Thin layer chromatography |
| tPSA | Topological polar surface area |
| XRPD | X-ray powder diffraction |

Intermediate 1 Synthesis and Characterization 2-((1r, 4r)-4-((5-Nitro-1-(phenylsulfonyl)-1H-pyrrolo[2,3-b]pyridin-4-yl)amino)cyclohexyl)acetonitrile

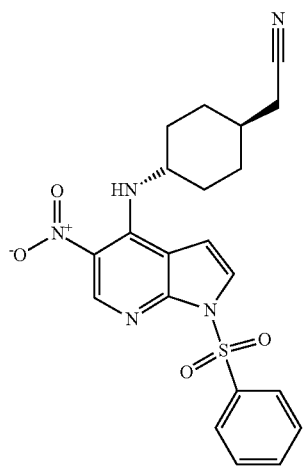

Step A: tert-butyl N-[(1r,4r)-4-(Hydroxymethyl)cyclohexyl]carbamate. To a 20-L 4-necked round-bottom flask purged and maintained with an inert atmosphere of nitrogen was placed (1r, 4r)-4-[[(tert-butoxy)carbonyl]amino]cyclohexane-1-carboxylic acid (1066 g, 4.38 mol, 1.00 equiv) and THF (10 L). This was followed by the dropwise addition of $BH_3$-$Me_2S$ (10 M, 660 mL) at −10° C. over 1 h. The resulting solution was stirred for 3 h at 15° C. This reaction was performed three times in parallel and the reaction mixtures were combined. The reaction was then quenched by the addition of methanol (2 L). The resulting mixture was concentrated under vacuum. This resulted in of tert-butyl N-[(1r,4r)-4-(hydroxymethyl)cyclohexyl]carbamate (3000 g, 99.6%) as a white solid. MS (ESI): mass calcd. for $C_{12}H_{23}NO_3$, 229.32; m/z found, 215.2 [M−tBu+MeCN+H]$^+$; $^1$H NMR: (300 MHz, CDCl$_3$): δ 4.40 (s, 1H), 3.45 (d, J=6.3 Hz, 2H), 3.38 (s, 1H), 2.05-2.02 (m, 2H), 1.84-1.81 (m, 2H), 1.44 (s, 11H), 1.17-1.01 (m, 4H).

Step B: tert-butyl N-[(1r,4r)-4-[(Methanesulfonyloxy)methyl]cyclohexyl]carbamate. To a 20 L 4-necked round-bottom flask purged and maintained with an inert atmosphere of nitrogen, was placed tert-butyl N-[(1r,4r)-4-(hydroxymethyl)cyclohexyl]carbamate (1000 g, 4.36 mol, 1.00 equiv.), dichloromethane (10 L), pyridine (1380 g, 17.5 mol, 4.00 equiv.). This was followed by the dropwise addition of MsCl (1000 g, 8.73 mol, 2.00 equiv.) at −15° C. The resulting solution was stirred overnight at 25° C. This reaction was performed in parallel for 3 times and the reaction mixtures were combined. The reaction was then quenched by the addition of 2 L of water. The water phase was extracted with ethyl acetate (1×9 L). The organic layer was separated and washed with 1 M HCl (3×10 L), NaHCO$_3$ (saturated aq.) (2×10 L), water (1×10 L) and brine (1×10 L). The mixture was dried over anhydrous sodium sulfate, filtered and concentrated under vacuum. This resulted in of tert-butyl N-[(1r,4r)-4-[(methanesulfonyloxy)methyl]cyclohexyl]carbamate (3300 g, 82%) as a white solid. LC-MS: MS (ESI): mass calcd. for $C_{13}H_{25}NO_5S$, 307.15; m/z found 292.1, [M−tBu+MeCN+H]$^+$; $^1$H NMR: (300 MHz, CDCl$_3$): δ 4.03 (d, J=6.6 Hz, 2H), 3.38 (s, 1H), 3.00 (s, 3H), 2.07-2.05 (m, 2H), 1.87-1.84 (m, 2H), 1.72-1.69 (m, 1H), 1.44 (s, 9H), 1.19-1.04 (m, 4H).

Step C: tert-butyl N-[(1r,4r)-4-(Cyanomethyl)cyclohexyl]carbamate. To a 10 L 4-necked round-bottom flask, was placed tert-butyl N-[(1r,4r)-4-[(methanesulfonyloxy)methyl]cyclohexyl]carbamate (1100 g, 3.58 mol, 1.00 equiv.), DMSO (5500 mL) and NaCN (406 g, 8.29 mol, 2.30 equiv.). The resulting mixture was stirred for 5 h at 90° C. This reaction was performed in parallel 3 times and the reaction mixtures were combined. The reaction was then quenched by the addition of 15 L of water/ice. The solids were collected by filtration. The solids were washed with water (3×10 L). This resulted in tert-butyl N-[(1r,4r)-4-(cyanomethyl)cyclohexyl]carbamate (2480 g, 97%) as a white solid. MS (ESI): mass calcd. for $C_{13}H_{22}N_2O_2$, 238.17; m/z found 224 [M−tBu+MeCN+H]$^+$; $^1$H NMR: (300 MHz, CDCl$_3$): δ 4.39 (s, 1H), 3.38 (s, 1H), 2.26 (d, J=6.9 Hz, 2H), 2.08-2.04 (m, 2H), 1.92-1.88 (m, 2H), 1.67-1.61 (m, 1H), 1.44 (s, 9H), 1.26-1.06 (m, 4H).

Step D: 2-[(1r,4r)-4-Aminocyclohexyl]acetonitrile hydrochloride. To a 10-L round-bottom flask was placed tert-butyl N-[(1r,4r)-4-(cyanomethyl)cyclohexyl]carbamate (620 g, 2.60 mol, 1.00 equiv.), and 1,4-dioxane (2 L). This was followed by the addition of a solution of HCl in 1,4-dioxane (5 L, 4 M) dropwise with stirring at 10° C. The resulting solution was stirred overnight at 25° C. This reaction was performed for 4 times and the reaction mixtures were combined. The solids were collected by filtration. The solids were washed with 1,4-dioxane (3×3 L), ethyl acetate (3×3 L) and hexane (3×3 L). This resulted in 2-[(1r,4r)-4-aminocyclohexyl]acetonitrile hydrochloride (1753 g, 96%) as a white solid. MS (ESI): mass calcd. for $C_8H_{14}N_2$, 138.12; m/z found 139.25, [M+H]$^+$; $^1$H NMR (300 MHz, DMSO-d$_6$): δ 8.14 (s, 3H), 2.96-2.84 (m, 1H), 2.46 (d, J=6.3 Hz, 2H), 1.98 (d, J=11.1 Hz, 2H), 1.79 (d, J=12.0 Hz, 2H), 1.64-1.49 (m, 1H), 1.42-1.29 (m, 2H), 1.18-1.04 (m, 2H).

Step E: 2-((1r,4r)-4-((5-Nitro-1-(phenylsulfonyl)-1H-pyrrolo[2,3-b]pyridin-4-yl)amino)cyclohexyl)acetonitrile. To a 1000 mL round bottom flask containing 2-[(1r,4r)-4-aminocyclohexyl]acetonitrile hydrochloride (29.10 g, 166.6 mmol) was added DMA (400 mL). The resulting suspension was treated with 4-chloro-5-nitro-1-(phenylsulfonyl)-1H-pyrrolo[2,3-b]pyridine (51.53 g, 152.6 mmol), followed by DIPEA (63.0 mL, 366 mmol). The reaction mixture was placed under N$_2$ and heated at 80° C. for 4 h. The crude reaction mixture was cooled to room temperature and slowly poured into a vigorously stirred 2 L flask containing 1.6 L water. The resulting suspension was stirred for 15 minutes at room temperature, then filtered and dried for 16 h in a vacuum oven with heating at 70° C. to provide the title compound (63.37 g, 95%) as a yellow solid. MS (ESI): mass calcd. for $C_{21}H_{21}N_5O_4S$, 439.1; m/z found, 440.1 [M+H]$^+$. $^1$H NMR (500 MHz, CDCl$_3$): δ 9.10 (s, 1H), 8.99 (d, J=7.8 Hz, 1H), 8.23-8.15 (m, 2H), 7.66-7.59 (m, 2H), 7.56-7.49 (m, 2H), 6.67 (d, J=4.2 Hz, 1H), 3.95-3.79 (m, 1H), 2.38 (d, J=6.2 Hz, 2H), 2.32-2.21 (m, 2H), 2.08-1.98 (m, 2H), 1.88-1.76 (m, 1H), 1.60-1.32 (m, 4H).

Intermediate 2 Synthesis and Characterization 2-((1r,4r)-4-((5-Amino-1-(phenylsulfonyl)-1H-pyrrolo[2,3-b]pyridin-4-yl)amino)cyclohexyl)acetonitrile

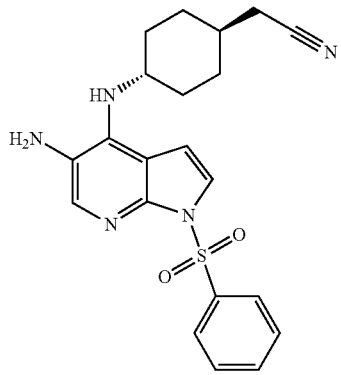 [SMILES: N#CC[C@H]1CC[C@H](Nc2c(N)cnc3c2ccn3S(=O)(=O)c2ccccc2)CC1]

2-((1r,4r)-4-((5-Nitro-1-(phenylsulfonyl)-1H-pyrrolo[2,3-b]pyridin-4-yl)amino)cyclohexyl)acetonitrile (Intermediate 1, 58.60 g, 133.3 mmol) was dissolved in THF/MeOH (1:1, 4800 mL). The mixture was passed through a continuous-flow hydrogenation reactor (10% Pd/C), such as a Thales Nano H-Cube®, at 10 mL/min with 100% hydrogen (atmospheric pressure, 80° C.), then the solution was concentrated to provide the product as a purple solid. The solid was triturated with EtOAc (400 mL) and then triturated again with MeOH (200 mL) then filtered and dried under vacuum to provide the title compound (50.2 g, 91.9% yield). MS (ESI): mass calcd. for $C_{21}H_{23}N_5O_2S$, 409.2; m/z found, 410.2 [M+H]$^+$. $^1$H NMR (400 MHz, CDCl$_3$) δ 8.10-8.03 (m, 2H), 7.76 (s, 1H), 7.51-7.43 (m, 1H), 7.43-7.34 (m, 3H), 6.44 (d, J=4.2 Hz, 1H), 4.61 (d, J=8.5 Hz, 1H), 3.65-3.51 (m, 1H), 2.74 (s, 2H), 2.26 (d, J=6.4 Hz, 2H), 2.19-2.05 (m, 2H), 1.97-1.86 (m, 2H), 1.76-1.59 (m, 1H), 1.33-1.12 (m, 4H).

Intermediate 3 Synthesis and Characterization

Ethyl 2-((1r,4r)-4-(cyanomethyl)cyclohexyl)-6-(phenylsulfonyl)-1,6-dihydroimidazo[4,5-d]pyrrolo[2,3-b]pyridin-2-yl)acetate

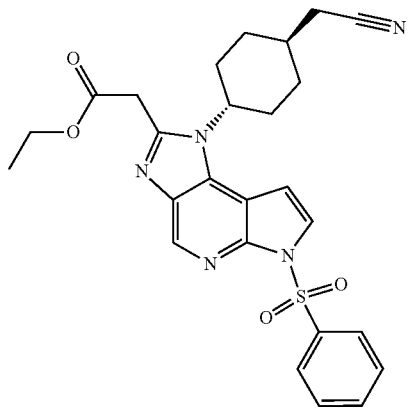 [SMILES: CCOC(=O)Cc1nc2cnc3c(ccn3S(=O)(=O)c3ccccc3)c2n1[C@H]1CC[C@H](CC#N)CC1]

To a 1 L round bottom flask containing a stir bar and 2-((1r,4r)-4-((5-amino-1-(phenylsulfonyl)-1H-pyrrolo[2,3-b]pyridin-4-yl)amino)cyclohexyl)acetonitrile (Intermediate 2, 58.31 g, 142.4 mmol) was added ethyl 3-ethoxy-3-iminopropanoate (60.51 g, 309.3 mmol), followed by EtOH (600 mL, dried over 3 Å molecular sieves for 48 h). A reflux condenser was attached to the reaction flask, the reaction was purged with N$_2$, and was heated at 90° C. for 9 h. The reaction mixture was cooled to room temperature and left to stand for 30 h where the product crystallized out as brown needles. The solids were broken up with a spatula and the reaction mixture was transferred to a 2 L flask. Water (1.4 L) was added slowly via separatory funnel with vigorous stirring. After addition of the water was complete, the suspension was stirred for 30 minutes. The brown needles were isolated by filtration and then dried by pulling air through the filter for 1 h. The product was transferred to a 500 mL flask and treated with EtOAc (200 mL). A small quantity of seed crystals were added, which induced the formation of a white solid precipitate. The suspension was stirred for 30 minutes at room temperature, filtered, rinsed with EtOAc (25 mL), and dried under vacuum to provide the product as a white solid (48.65 g, 68% yield). MS (ESI): mass calcd. for $C_{26}H_{27}N_5O_4S$, 505.2; m/z found, 506.2 [M+H]$^+$. $^1$H NMR (400 MHz, CDCl$_3$) δ 8.85 (s, 1H), 8.28-8.19 (m, 2H), 7.84 (d, J=4.0 Hz, 1H), 7.61-7.53 (m, 1H), 7.52-7.43 (m, 2H), 6.84 (d, J=4.1 Hz, 1H), 4.32 (s, 1H), 4.20 (q, J=7.1 Hz, 2H), 4.09 (s, 2H), 2.44 (d, J=6.2 Hz, 2H), 2.40-2.27 (m, 2H), 2.16 (d, J=13.3 Hz, 2H), 2.12-1.96 (m, 3H), 1.54-1.38 (m, 2H), 1.27 (t, J=7.1 Hz, 3H).

Intermediate 4 Synthesis and Characterization

Sodium 2-(1-((1r,4r)-4-(cyanomethyl)cyclohexyl)-1,6-dihydroimidazo[4,5-d]pyrrolo[2,3-b]pyridin-2-yl)acetate

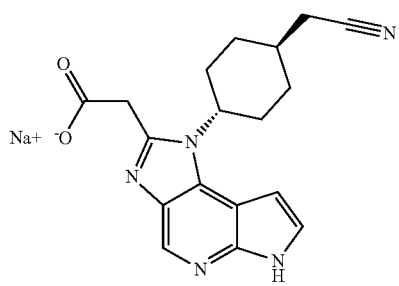

To a solution of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 9.50 g, 18.8 mmol) in MeOH (30 mL) and THF (30 mL) was added aq sodium hydroxide (56.4 mL, 56.4 mmol, 1 M) and was stirred at room temperature for 14 hours. The solvent was removed under reduced pressure at room temperature to provide the title compound (7 g) as a brown solid, which was used in the next step without further purification. MS (ESI): mass calcd. for $C_{18}H_{18}N_5NaO_2$, 359.1; m/z found, 337.9 [M+H−Na]$^+$. $^1$H NMR (400 MHz, CD$_3$OD) δ 8.52-8.47 (m, 1H), 7.85-7.81 (m, 2H), 7.46-7.41 (m, 4H), 6.85-6.81 (m, 1H), 4.60-4.46 (m, 1H), 3.96 (s, 2H), 2.59-2.49 (m, 4H), 2.19-2.05 (m, 6H), 1.56-1.43 (m, 2H) (a 1:1 mixture of the title compound and benzenesulfonic acid).

Example 1 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide

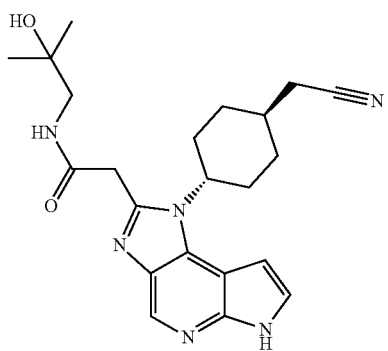

(Ex. 1)

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide. To ensure dry starting material, ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3) was heated under vacuum at 50° C. for 18 h prior to the reaction. In a 1 L flask, ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 52.585 g, 104.01 mmol) was suspended in DMA (50 mL). 1-Amino-2-methylpropan-2-ol (50 mL) was added and the reaction was heated to 110° C. for 45 minutes, then to 125° C. for 5 hours. The reaction was cooled to room temperature and diluted with EtOAc (800 mL). The organic layer was extracted three times with a solution of water/brine wherein the solution was made up of 1 L water plus 50 mL brine. The aqueous layers were back extracted with EtOAc (2×600 mL). The combined organic layers were dried over anhydrous MgSO$_4$, concentrated to dryness, and then dried for 3 days under vacuum to provide the title compound (65.9 g, 98% yield) as a yellow foam. The product was taken to the next step with no further purification. MS (ESI): mass calcd. for C$_{24}$H$_{32}$N$_6$O$_4$S, 548.22; m/z found, 549.2 [M+H]$^+$. $^1$H NMR (400 MHz, CDCl$_3$): δ 8.76 (s, 1H), 8.26-8.19 (m, 2H), 7.84 (d, J=4.1 Hz, 1H), 7.60-7.53 (m, 1H), 7.50-7.44 (m, 2H), 6.84 (d, J=4.2 Hz, 1H), 4.76-4.61 (m, 1H), 3.97 (s, 2H), 3.45 (s, 1H), 3.27 (d, J=5.9 Hz, 2H), 2.41 (d, J=6.5 Hz, 2H), 2.38-2.25 (m, 2H), 2.23-2.12 (m, 2H), 2.09-1.94 (m, 4H), 1.48 (qd, J=13.6, 4.0 Hz, 2H), 1.21 (s, 6H).

Step B: 2-(1-((1r,4r)-4-(Cyanomethyl)cyclohexyl)-1,6-dihydroimidazo[4,5-d]pyrrolo[2,3-b]pyridin-2-yl)-N-(2-hydroxy-2-methylpropyl)acetamide. 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide (65.90 g, 102.1 mmol) was added to a 1 L flask containing a stir bar. 1,4-dioxane (300 mL) was added, followed by aq KOH (3 M, 150 mL).

The reaction was heated at 80° C. for 2 h. The reaction was cooled to room temperature and the solvent volume was reduced to about 200 mL on a rotovap. The residue was treated with a solution of water/brine (100 mL/100 mL), then extracted with 10% MeOH in CH$_2$Cl$_2$ (2×1 L). The organic layers were combined, dried over anhydrous MgSO$_4$, and concentrated to dryness to provide a yellow solid. The solid was suspended in CH$_2$Cl$_2$ (200 mL), stirred vigorously for 30 minutes, and then collected by filtration. The solid was rinsed with CH$_2$Cl$_2$ (100 mL), dried by pulling air through the filter, and then further dried under vacuum at room temperature for 16 h to provide the title compound (41.59 g, 89% yield) as a white solid. MS (ESI): mass calcd. for C$_{22}$H$_{28}$N$_6$O$_2$, 408.23; m/z found, 409.2 [M+H]$^+$. $^1$H NMR (600 MHz, DMSO-d$_6$): δ 11.85 (s, 1H), 8.50 (s, 1H), 8.21-8.10 (m, 1H), 7.49-7.43 (m, 1H), 6.74-6.65 (m, 1H), 4.53-4.42 (m, 2H), 4.07 (s, 2H), 3.08 (d, J=6.0 Hz, 2H), 2.58 (d, J=6.1 Hz, 2H), 2.41-2.28 (m, 2H), 2.09-1.92 (m, 5H), 1.42-1.31 (m, 2H), 1.09 (s, 6H). The synthesis and active compound characterization of each of the embodiments of this invention are provided herein in the form of examples. Due to the crystal structure of some of the embodiments of this invention, polymorph screening may be pursued to further characterize specific forms of any such compound. This is illustrated in a non-limiting manner for compound Ex. 1 by the example under the heading polymorph screening. Tests reported herein concerning compound Ex. 1 were performed with such compound in a form given by embodiment 1s as described in the polymorph screening example below.

Example 2 Synthesis and Characterization 2-((1r,4r)-4-(2-(1H-Imidazol-4-yl)imidazo[4,5-d]pyrrolo[2,3-b]pyridin-1(6H)-yl)cyclohexyl)acetonitrile

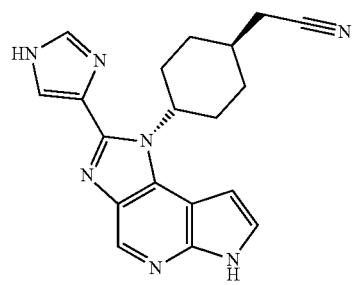

(Ex. 2)

Step A: 2-((1r,4r)-4-(2-(1H-Imidazol-4-yl)-6-(phenylsulfonyl)imidazo[4,5-d]pyrrolo[2,3-b]pyridin-1(6H)-yl)cyclohexyl)acetonitrile. 2-((1r,4r)-4-((5-Nitro-1-(phenylsulfonyl)-1H-pyrrolo[2,3-b]pyridin-4-yl)amino)cyclohexyl)acetonitrile (Intermediate 1, 23.3 g, 53.0 mmol) was added into a 1 L round-bottomed flask containing a magnetic stir-bar followed by the addition of DMSO (200 mL) and methanol (200 mL). 1H-Imidazole-4-carbaldehyde (8.56 g, 89.1 mmol) was added as a solid, followed by the addition of sodium hydrosulfite (32.7 g, 188 mmol) as a solution in water (100 mL). The reaction vessel was equipped with a reflux condenser and heated to 90° C. in a heating block for 15 h. The reaction mixture was then cooled to room temperature and added to a flask containing water (2000 mL) with stirring, which resulted in formation of a white precipitate. The mixture was stirred for 30 minutes and the solids were collected by filtration. The solids were dried by pulling air through the filter for 6 h and then further dried in a vacuum oven heating at 60° C. for 3 days to provide the title compound (22.7 g, 88% yield) as a yellow solid. MS (ESI): mass calcd. for $C_{25}H_{23}N_7O_2S$, 485.16; m/z found, 486.1 [M+H]$^+$. $^1$H NMR (400 MHz, CDCl$_3$): δ 8.74 (s, 1H), 8.29 (s, 1H), 8.20-8.11 (m, 2H), 8.04-7.96 (m, 2H), 7.76-7.68 (m, 1H), 7.68-7.60 (m, 2H), 7.19 (d, J=4.2 Hz, 1H), 5.56 (s, 1H), 2.58 (d, J=6.3 Hz, 2H), 2.38-2.24 (m, 2H), 2.07 (s, 1H), 1.98 (d, J=10.8 Hz, 5H), 1.35 (q, J=12.3 Hz, 2H).

Step B: 2-((1r,4r)-4-(2-(1H-Imidazol-4-yl)imidazo[4,5-d]pyrrolo[2,3-b]pyridin-1(6H)-yl)cyclohexyl)acetonitrile. The title compound was prepared using conditions analogous to those described in Example 1, Step B using 2-((1r,4r)-4-(2-(1H-imidazol-4-yl)-6-(phenylsulfonyl)imidazo[4,5-d]pyrrolo[2,3-b]pyridin-1(6H)-yl)cyclohexyl)acetonitrile (222 mg, 0.46 mmol) instead of 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)-N-(2-hydroxy-2-methylpropyl)acetamide and the residue was purified by flash column chromatography (0-15% 2 N NH$_3$-MeOH/EA) to provide the title compound (97 mg, 69% yield). MS (ESI): mass calcd. for $C_{19}H_{19}N_7$, 345.17; m/z found, 346.0 [M+H]$^+$. $^1$H NMR (400 MHz, DMSO-d$_6$): δ 12.61 (s, 1H), 11.86 (s, 1H), 8.55 (s, 1H), 7.92 (d, J=1.3 Hz, 1H), 7.83 (s, 1H), 7.48 (t, J=3.0 Hz, 1H), 6.76 (dd, J=3.5, 1.8 Hz, 1H), 5.85 (s, 1H), 2.60 (d, J=6.0 Hz, 2H), 2.57-2.41 (m, 2H), 2.14-1.88 (m, 5H), 1.45-1.27 (m, 2H).

Example 3 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide

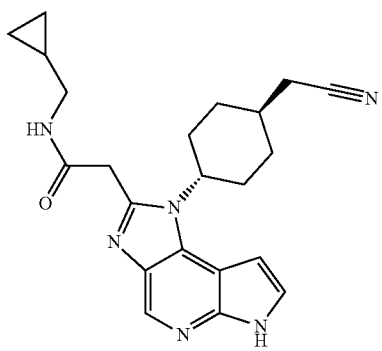
(Ex. 3)

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(cyclopropylmethyl)acetamide. A mixture of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 555 mg, 1.06 mmol) and cyclopropylmethylamine (1.87 mL, 21.1 mmol) was heated at 125° C. for 1 h in a microwave reactor. The residue was treated with water then extracted with ethyl acetate. The organic layers were combined, dried over sodium sulfate, passed through a silica plug, and concentrated to dryness using a rotovap to provide the title compound (642 mg). MS (ESI): mass calcd. for $C_{28}H_{30}N_6O_3S$, 530.21; m/z found, 531.2 [M+H]$^+$. $^1$H NMR (400 MHz, CD$_3$OD): δ 8.64 (s, 1H), 8.19-8.11 (m, 2H), 7.95 (d, J=4.1 Hz, 1H), 7.66-7.57 (m, 1H), 7.57-7.48 (m, 2H), 7.11 (d, J=4.1 Hz, 1H), 4.53 (s, 1H), 4.08 (s, 2H), 3.07 (d, J=7.1 Hz, 2H), 2.53 (d, J=5.9 Hz, 2H), 2.45-2.30 (m, 2H), 2.14-2.03 (m, 5H), 1.55-1.42 (m, 2H), 1.02-0.94 (m, 1H), 0.54-0.47 (m, 2H), 0.24-0.18 (m, 2H).

Step B: 2-(1-((1r,4r)-4-(Cyanomethyl)cyclohexyl)-1,6-dihydroimidazo[4,5-d]pyrrolo[2,3-b]pyridin-2-yl)-N-(cyclopropylmethyl)acetamide. To a mixture of 2-(1-((1r, 4r)-4-(cyanomethyl)cyclohexyl)-6-(phenylsulfonyl)-1,6-dihydroimidazo[4,5-d]pyrrolo[2,3-b]pyridin-2-yl)-N-(cyclopropylmethyl)acetamide (560 mg, 1.05 mmol) in 1,4-dioxane (4.22 mL) was added 3N KOH (2.81 mL). The mixture was heated at 80° C. for 1 hr, then purified with basic HPLC: Xbridge Prep OBD C$_{18}$ 50 mm×100 mm, 5 μm column (eluent 0-100% aq NH$_4$OH/ACN (10 min)) to provide the title compound (187 mg, 46% yield). MS (ESI): mass calcd. for $C_{22}H_{26}N_6O$, 390.22; m/z found, 391.2 [M+H]$^+$. $^1$H NMR (400 MHz, CD$_3$OD): δ 8.57 (s, 1H), 7.50 (d, J=3.5 Hz, 1H), 6.86 (d, J=3.5 Hz, 1H), 4.57 (s, 1H), 4.11 (s, 2H), 3.13 (d, J=7.0 Hz, 2H), 2.67-2.52 (m, 4H), 2.20-2.03 (m, 5H), 1.58-1.44 (m, 2H), 1.12-0.97 (m, 1H), 0.60-0.48 (m, 2H), 0.31-0.22 (m, 2H).

Example 4 Synthesis and Characterization

N-(2-Cyanoethyl)-2-(1-((1r,4r)-4-(cyanomethyl)cyclohexyl)-1,6-dihydroimidazo[4,5-d]pyrrolo[2,3-b]pyridin-2-yl)acetamide

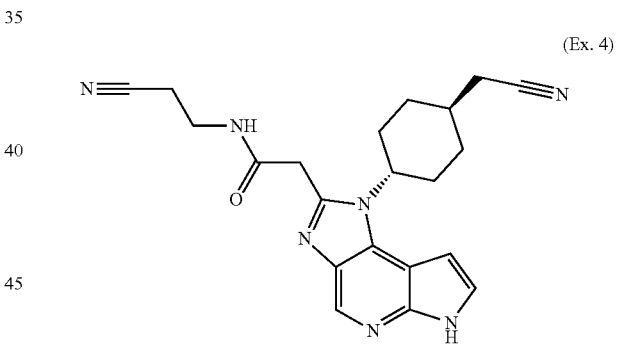
(Ex. 4)

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 400 mg, 1.11 mmol) and 3-aminopropanenitrile (320 mg, 2.24 mmol) in DMF (5 mL) was added PyBOP (870 mg, 1.67 mmol) and DIPEA (0.60 mL, 3.5 mmol). The reaction mixture was stirred at room temperature for 40 h. After removal of the DMF in vacuo, the residue was purified by flash column chromatography using 50-100% ethyl acetate in heptane. The collected fractions were concentrated in vacuo to a small volume and white solid which had precipitated out was filtered off, washed with 10% MeOH in CH$_2$Cl$_2$, and dried to provide to provide the title compound (75 mg, 17% yield). The filtrate was concentrated to dryness and purified by reverse phase-HPLC using a Varian Pursuit XR$_s$5 Diphenyl 100 mm×30 mm column (eluent 10-90% CH$_3$CN in water, 0.1% TFA) to provide a clear oil. This material was dissolved in 10%

MeOH in CH$_2$Cl$_2$, passed through three 500 mg columns of SILICYCLE SPE-R66030B-03P Carbonate (SiliaBond acid scavenger solid phase extraction cartridge) to remove the TFA and eluted with 10% MeOH in CH$_2$Cl$_2$ to provide an additional fraction of the title compound (88 mg, 20% yield). The two fractions were combined to provide the final product (163 mg, 37% yield) as a white solid. MS (ESI): mass calcd. for C$_{21}$H$_{23}$N$_7$O, 389.20; m/z found, 390.3 [M+H]$^+$. $^1$H NMR (400 MHz, CD$_3$OD): δ 8.53 (s, 1H), 7.48 (d, J=3.0 Hz, 1H), 6.84 (d, J=3.5 Hz, 1H), 4.51 (br s, 1H), 4.12 (s, 2H), 3.50 (t, J=6.6 Hz, 2H), 2.71 (t, J=6.6 Hz, 2H), 2.45-2.63 (m, 4H), 2.03-2.19 (m, 5H), 1.44-1.57 (m, 2H).

Example 5 Synthesis and Characterization 2-(1-((1r,4r)-4-(cyanomethyl)cyclohexyl)-1,6-dihydroimidazo[4,5-d]pyrrolo[2,3-b]pyridin-2-yl)-N-(tetrahydro-2H-pyran-4-yl)acetamide

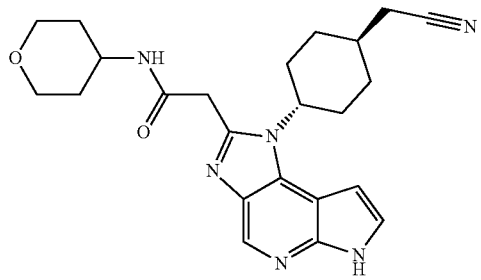

(Ex. 5)

A mixture of ethyl 2-(1-((1r,4r)-4-(cyanomethyl)cyclohexyl)-6-(phenylsulfonyl)-1,6-dihydroimidazo[4,5-d]pyrrolo[2,3-b]pyridin-2-yl)acetate (Intermediate 3, 309 mg, 0.61 mmol) and 4-aminotetrahydropyran (195 mg, 1.93 mmol) in 1,4-dioxane (0.5 mL) was heated in a microwave reactor at 180° C. for 1 hr. The reaction mixture was then diluted with 1,4-dioxane (1.5 mL), treated with aq 3N KOH (2 mL), and heated at 80° C. for 1.5 hr. The residue was then treated with water (10 mL) and extracted with CH$_2$Cl$_2$ (3×50 mL). The organic layers were combined, dried over MgSO$_4$ and concentrated in vacuo. The crude material was purified using flash column chromatography (5-10% MeOH/CH$_2$Cl$_2$) to yield the title compound (146 mg, 57% yield). MS (ESI): mass calcd. for C$_{23}$H$_{28}$N$_6$O$_2$, 420.23; m/z found, 421.2 [M+H]$^+$. $^1$H NMR (600 MHz, DMSO-d$_6$): δ 11.84 (s, 1H), 8.49 (s, 1H), 8.36 (d, J=7.5 Hz, 1H), 7.46 (t, J=3.0 Hz, 1H), 6.73-6.67 (m, 1H), 4.54-4.41 (m, 1H), 3.98 (s, 2H), 3.86-3.81 (m, 2H), 3.81-3.74 (m, 1H), 3.40-3.34 (m, 2H), 2.60 (d, J=6.0 Hz, 2H), 2.41-2.29 (m, 2H), 2.10-2.01 (m, 1H), 2.00-1.93 (m, 4H), 1.77-1.70 (m, 2H), 1.49-1.33 (m, 4H).

Example 6 Synthesis and Characterization 2-(1-(((1r,4r)-4-(Cyanomethyl)cyclohexyl)-1,6-dihydroimidazo[4,5-d]pyrrolo[2,3-b]pyridin-2-yl)-N-((tetrahydro-2H-pyran-4-yl)methyl)acetamide

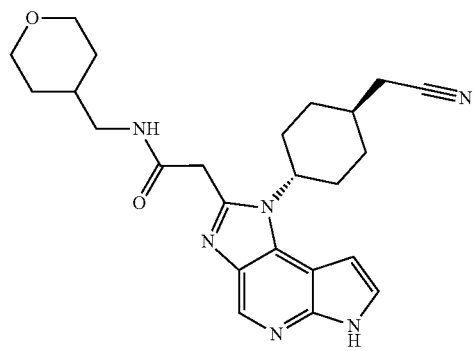

(Ex. 6)

To a microwave vial were added ethyl 2-(1-((1r,4r)-4-(cyanomethyl)cyclohexyl)-6-(phenylsulfonyl)-1,6-dihydroimidazo[4,5-d]pyrrolo[2,3-d]pyridin-2-yl)acetate (Intermediate 3, 300 mg, 0.593 mmol) and 4-aminomethyltetrahydropyran (683 mg, 5.93 mmol). The resulting solution was stirred at 125° C. for 1 h. Next were added dioxane (2.37 mL) and KOH (3 M in water, 1.58 mL, 4.75 mmol) and the reaction was stirred in the microwave at 80° C. for 1 h. The reaction was purified over basic HPLC using a Waters Xbridge Prep OBD C$_{18}$ 150 mm×30 mm, 5 µm column (eluent 0-100% water (0.05% NH$_4$OH)/ACN (10 min)) to provide the title compound (97 mg, 38% yield). MS (ESI): mass calcd. for C$_{24}$H$_{30}$N$_6$O$_2$, 434.24; m/z found, 435.2 [M+H]$^+$. $^1$H NMR (500 MHz, CD$_3$OD): δ 8.43 (s, 1H), 7.38 (d, J=3.5 Hz, 1H), 6.74 (d, J=3.5 Hz, 1H), 4.43 (s, 1H), 4.03-3.96 (m, 2H), 3.89-3.79 (m, 2H), 3.34-3.25 (m, 2H), 3.04 (d, J=6.8 Hz, 2H), 2.54-2.38 (m, 4H), 2.08-1.96 (m, 5H), 1.74-1.63 (m, 1H), 1.59-1.54 (m, 2H), 1.46-1.33 (m, 2H), 1.25-1.14 (m, 2H).

Example 7 Synthesis and Characterization

N-(2-Cyano-2-methylpropyl)-2-(1-((1r,4r)-4-(cyanomethyl)cyclohexyl)-1,6-dihydroimidazo[4,5-d]pyrrolo[2,3-b]pyridin-2-yl)acetamide

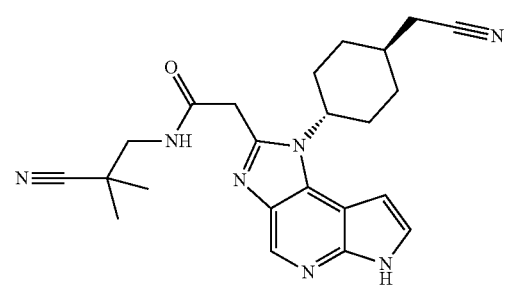

(Ex. 7)

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 3-amino-2,2-dimethylpropanenitrile (82.0 mg, 0.835 mmol), DIPEA (216 mg, 1.67 mmol), and DMF (5 mL) was stirred at 0° C. for 1 h. Then PyBrOP (467 mg, 1.00 mmol) was added and the reaction mixture stirred overnight at room temperature. The mixture was quenched with 10 mL water and was purified by preparative HPLC using a Waters Xbridge Prep OBD Cis 150 mm×30 mm 5 µm column (eluent: 28% water (0.05% ammonia hydroxide v/v)-ACN to provide the title compound (58 mg, 16% yield) as a white solid. MS (ESI): mass calcd. for $C_{23}H_{27}N_7O$, 417.23; m/z found, 418.2 [M+H]$^+$. $^1$H NMR (400 MHz, DMSO-d$_6$): δ 11.86 (br s, 1H), 8.71-8.66 (m, 1H), 8.50 (s, 1H), 7.48-7.45 (m, 1H), 6.73-6.69 (m, 1H), 4.53-4.42 (m, 1H), 4.10 (s, 2H), 3.33-3.31 (m, 1H), 2.57 (d, J=5.6 Hz, 2H), 2.41-2.27 (m, 2H), 2.05-1.93 (m, 5H), 1.45-1.26 (m, 9H).

Example 8 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1-hydroxycyclobutyl)methyl)acetamide

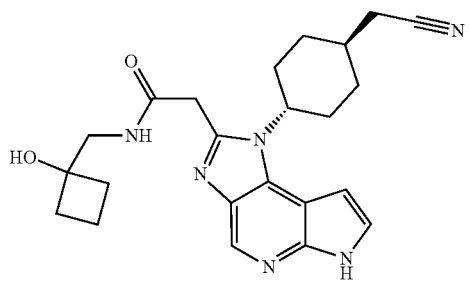
(Ex. 8)

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 1-(aminomethyl)cyclobutanol (84.4 mg, 0.835 mmol), DIPEA (216 mg, 1.67 mmol), and DMF (5 mL) was stirred at 0° C. for 1 h. Next, PyBrOP (467 mg, 1.00 mmol) was added and was stirred at room temperature overnight, then quenched with 10 mL water. The reaction was purified by preparative basic HPLC using a Kromasil 150 mm×25 mm, 10 µm column (eluent: water (0.05% ammonia hydroxide v/v)-ACN from 9% to 39%, v/v) to provide the title compound (90 mg, 26% yield) as a white solid. MS (ESI): mass calcd. for $C_{23}H_{28}N_6O_2$, 420.23; m/z found, 421.2 [M+H]$^+$. $^1$H NMR (400 MHz, DMSO-d$_6$): δ 11.58 (br s, 1H), 8.50 (s, 1H), 7.94-7.85 (m, 1H), 7.46-7.40 (m, 1H), 6.75-6.70 (m, 1H), 4.89 (br s, 1H), 4.57-4.47 (m, 1H), 4.04 (s, 2H), 3.27 (d, J=6.0 Hz, 2H), 2.55 (d, J=6.0 Hz, 2H), 2.45-2.31 (m, 2H), 2.10-1.88 (m, 9H), 1.71-1.60 (m, 1H), 1.54-1.35 (m, 3H).

Example 9 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1-methyl-1H-pyrazol-4-yl)acetamide

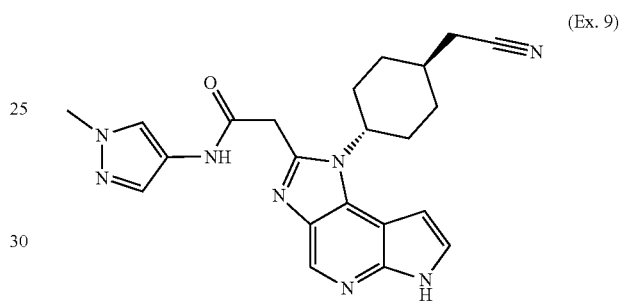
(Ex. 9)

To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 100 mg, 0.278 mmol) and 1-methyl-1H-pyrazol-4-amine (54.0 mg, 0.557 mmol) in DMF (0.8 mL) were added PyBrOP (217 mg, 0.417 mmol) and DIPEA (0.144 mL, 0.835 mmol) and the mixture was stirred at room temperature overnight. The DMF was removed under reduced pressure and the residue was purified by flash column chromatography (50-100% EtOAc/heptanes, then 10% MeOH/DCM) and the subsequently by reverse phase HPLC using a Varian Pursuit XR$_s$5 Diphenyl 100 mm×30 mm column (eluent 10-90% $CH_3CN$ in water, 0.1% TFA) to provide the product as the TFA salt. This material was dissolved in 10% MeOH in $CH_2Cl_2$ and passed through a 500 mg column of SILICYCLE SPE-R66030B-03P Carbonate (SiliaBond acid scavenger solid phase extraction cartridge) to remove the TFA to provide the title compound (34 mg, 29% yield) as a white solid. MS (ESI): mass calcd. for $C_{22}H_{24}N_8O$, 416.21; m/z found, 417.3 [M+H]$^+$. $^1$H NMR (400 MHz, CDCl$_3$) δ=12.77 (br s, 1H), 11.24 (br s, 1H), 7.94 (s, 1H), 7.89 (br s, 1H), 7.46 (s, 1H), 7.29-7.20 (m, 1H), 6.74 (br s, 1H), 4.85-4.65 (m, 1H), 4.23 (s, 2H), 3.85 (s, 3H), 2.80-2.55 (m, 1H), 2.45 (d, J=6.6 Hz, 2H), 2.32-1.98 (m, 6H), 1.62-1.44 (m, 2H).

Example 10 Synthesis and Characterization

N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide

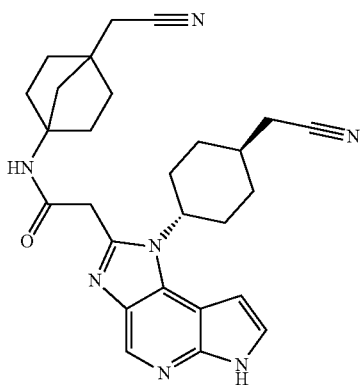

(Ex. 10)

Step A: Dimethyl cyclopentane-1,3-dicarboxylate. A solution of cyclopentane-1,3-dicarboxylic acid (70.0 g, 443 mmol) and anhydrous methanol (300 mL) was cooled to 0° C. in an ice water bath. Concentrated sulfuric acid (14 mL) was added dropwise, maintaining the temperature at <15° C. After the addition, the reaction was heated to 90° C. and stirred overnight. The reaction was cooled to room temperature and concentrated to dryness. The residue was treated with MTBE (500 mL) and $H_2O$ (100 mL). The aqueous layer was separated and extracted with MTBE (2×100 mL). The combined organic extracts were washed with saturated sodium bicarbonate (2×100 mL), brine (100 mL), dried over anhydrous $MgSO_4$, filtered, and concentrated to dryness to provide the title compound (72.5 g, 88%) as a pale yellow oil. $^1$H NMR (400 MHz, $CDCl_3$) δ 3.65 (s, 6H), 2.84-2.72 (m, 2H), 2.26-2.17 (m, 1H), 2.11-2.02 (m, 1H), 1.96-1.88 (m, 4H).

Step B: Dimethyl bicyclo[2.2.1]heptane-1,4-dicarboxylate. n-Butyllithium (2.5 M in hexane, 419.0 mL, 1048 mmol) was added slowly to a solution of diisopropylamine (152 mL, 1090 mmol) and anhydrous THF (1000 mL) at −78° C. (dry ice/acetone) under $N_2$. Next, the reaction was stirred for 0.5 hours at 0° C. before cooling to −78° C. DMPU (404 mL, 3350 mmol) was added via an addition funnel. Then a solution of dimethyl cyclopentane-1,3-dicarboxylate (78.0 g, 419 mmol) and anhydrous THF (300 mL) was added slowly via an addition funnel. The reaction was warmed to 0° C. and stirred for 30 minutes, then cooled to −78° C. and treated with a solution of 1-bromo-2-chloroethane (59.0 mL, 712 mmol) and anhydrous THF (200 mL). The reaction was allowed to warm slowly to room-temperature and was stirred for 12 hours at room-temperature. The reaction was quenched with saturated aqueous ammonium chloride (400 mL). The reaction was diluted with ethyl acetate (500 mL), the organic layer separated, and the aqueous layer was further extracted with ethyl acetate (2×500 mL). The combined organic extracts were washed with brine (2×300 mL), dried over anhydrous $MgSO_4$, filtered, and concentrated to dryness. The residue was filtered through a pad of silica gel and washed with ethyl acetate (2000 mL). The filtrate was concentrated to dryness and the residue was purified by flash column chromatography (petroleum ether/ethyl acetate, 30:1 to 20:1, gradient elution) to provide the title compound (48.5 g, 54%) as white solid. $^1$H NMR (400 MHz, $CDCl_3$): δ 3.69 (s, 6H), 2.08-1.99 (m, 4H), 1.91 (s, 2H), 1.73-1.63 (m, 4H).

Step C: 4-(Methoxycarbonyl)bicyclo[2.2.1]heptane-1-carboxylic acid. A methanol (80 mL) solution of sodium hydroxide (5.145 g, 128.6 mmol) was added slowly to a solution of dimethyl bicyclo[2.2.1]heptane-1,4-dicarboxylate (27.3 g, 129 mmol) and THF (700 mL) at 0° C. and the reaction mixture was stirred at room temperature overnight. The reaction was concentrated to dryness and the residue was triturated with MTBE (15 mL). The precipitate was collected by filtration, washed with MTBE (5 mL), and dissolved in 100 mL of $H_2O$. The solution was acidified to pH=4 with 2 M HCl. The precipitate was collected by filtration and dried under vacuum to provide the title compound (13.0 g, 51.0%) as white solid. The filtrate was extracted with ethyl acetate (3×75 mL) and the combined organic extracts were washed with brine (50 mL), dried over anhydrous $MgSO_4$, filtered and concentrated to dryness to provide a second fraction of the title compound (8.0 g, 31%) as a white solid. $^1$H NMR (400 MHz, DMSO-$d_6$) δ 12.21 (br s, 1H), 3.59 (s, 3H), 1.94-1.86 (m, 4H), 1.74 (s, 2H), 1.61-1.54 (m, 4H).

Step D: Methyl 4-(((benzyloxy)carbonyl)amino)bicyclo[2.2.1]heptane-1-carboxylate. Diphenylphosphoryl azide (17.1 mL, 78.6 mmol) was added to a solution of 4-(methoxycarbonyl)bicyclo[2.2.1]heptane-1-carboxylic acid (13.0 g, 65.6 mmol), DIPEA (22.8 mL, 131 mmol), and anhydrous toluene (200 mL) and the reaction mixture was stirred at 110° C. for 2 hours. The reaction was cooled to 50° C. and benzyl alcohol (13.6 mL, 131 mmol) was added and the reaction mixture was stirred at 110° C. overnight. The reaction was concentrated to dryness, dissolved in MTBE (250 mL) and washed with $H_2O$ (150 mL). The organic layer was separated and the aqueous layer was extracted with MTBE (2×100 mL). The combined organic extracts were washed with brine (100 mL), dried over anhydrous $MgSO_4$, filtered, and concentrated to dryness. The residue was purified by flash column chromatography (petroleum ether/ethyl acetate, 10:1 to 5:1, gradient elution) to provide an impure product (28.5g) as pale yellow oil. The product was further purified by preparative acidic HPLC using a Phenomenex Synergi Max-RP 250×50 mm×10 μm column (eluent: 38% to 68% (v/v) $CH_3CN$ and $H_2O$ with 0.1% TFA). The pure fractions were combined and the volatiles were removed under vacuum. The residue was diluted with $H_2O$ (80 mL), the pH of the solution was adjusted to pH=8 with saturated aqueous $NaHCO_3$ solution, and the resulting solution was extracted with $CH_2Cl_2$ (3×100 mL). The combined organic extracts were washed with brine (75 mL), dried over anhydrous $MgSO_4$, filtered, and concentrated to dryness to provide the title compound (17.3 g, 85%) as a colorless oil. MS (ESI): mass calcd. for $C_{17}H_{21}NO_4$, 303.2; m/z found, 303.9 [M+H]$^+$. $^1$H NMR (400 MHz, DMSO-$d_6$) δ 7.56 (br s, 1H), 7.37-7.30 (m, 5H), 4.97 (s, 2H), 3.58 (s, 3H), 1.90-1.80 (m, 6H), 1.65-1.59 (m, 4H).

Step E: Methyl 4-((tert-butoxycarbonyl)amino)bicyclo[2.2.1]heptane-1-carboxylate. A mixture of methyl 4-(((benzyloxy)carbonyl)amino)bicyclo[2.2.1]heptane-1-carboxylate (17 g, 56 mmol), di-tert-butyl dicarbonate (18.35 g, 84.06 mmol), MeOH (200 mL) and wet Pd/C (4 g, 10 wt. %, 50% $H_2O$) was added to a 500 mL round-bottom flask with a hydrogen balloon (13 psi) and was stirred at room temperature for 72 hours. The catalyst was filtered off and the filtrate was concentrated to dryness. The residue was purified by flash column chromatography (petroleum ether/ethyl acetate, 20:1 to 1:1, gradient elution) to provide the title compound (12.0 g, 79.5%) as a white solid. $^1$H NMR (400 MHz, DMSO-$d_6$) δ 7.04 (br s, 1H), 3.57 (s, 3H), 1.93-1.78 (m, 4H), 1.77 (s, 2H), 1.63-1.53 (m, 4H), 1.35 (s, 9H).

Step F: 4-((tert-Butoxycarbonyl)amino)bicyclo[2.2.1]heptane-1-carboxylic acid. To a solution of methyl 4-((tert-butoxycarbonyl)amino)bicyclo[2.2.1]heptane-1-carboxylate (5.0 g, 19 mmol), THF (40 mL) and MeOH (20 mL) was added aqueous sodium hydroxide (1.0 M, 46.4 mL, 46.4 mmol) at room temperature and the reaction mixture was stirred at room temperature for 24 hours. The reaction was concentrated to dryness and the residue was diluted with H$_2$O (20 mL), acidified to pH=4-5 with 2 M HCl to provide a precipitate. The precipitate was dissolved in 150 mL of ethyl acetate, washed with brine (45 mL), dried over anhydrous Na$_2$SO$_4$, filtered, and concentrated to dryness to provide the title compound (4.74 g, 100% yield) as white solid, which was used directly in the next step. $^1$H NMR (400 MHz, DMSO-$d_6$) δ 12.06 (br s, 1H), 7.00 (br s, 1H), 1.87-1.73 (m, 6H), 1.58-1.50 (m, 4H), 1.35 (s, 9H).

Step G: tert-Butyl (4-(hydroxymethyl)bicyclo[2.2.1]heptan-1-yl)carbamate. A solution of borane-tetrahydrofuran complex (1.0 M, 37.1 mL, 37.1 mmol) was added slowly to a solution of 4-((tert-butoxycarbonyl)amino)bicyclo[2.2.1]heptane-1-carboxylic acid (4.74 g, 18.6 mmol) and anhydrous THF (50 mL) at 0° C. under a nitrogen atmosphere. After the addition was complete, the reaction was stirred at room temperature overnight. Water (30 mL) was added to the mixture slowly and it was stirred for additional 30 minutes. The reaction was concentrated to dryness and the residue was diluted with ethyl acetate (50 mL), washed with H$_2$O (15 mL) and brine (10 mL), dried over anhydrous Na$_2$SO$_4$, filtered, and concentrated to dryness. The residue was purified by flash column chromatography (petroleum ether/ethyl acetate, 2:1) to provide the title compound (4.0 g, 89% yield) as white solid. TLC (petroleum ether/ethyl acetate, 2:1), $R_f$=0.5. $^1$H NMR (400 MHz, DMSO-$d_6$): 6.88 (br s, 1H), 4.38 (t, J=5.4 Hz, 1H), 3.36 (d, J=5.4 Hz, 2H), 1.73 (br s, 2H), 1.64-1.49 (m, 4H), 1.42 (s, 2H), 1.39-1.33 (m, 9H), 1.25-1.16 (m, 2H).

Step H: (4-(((tert-Butoxycarbonyl)amino)bicyclo[2.2.1]heptan-1-yl)methyl methanesulfonate. Pyridine (2.7 mL, 33 mmol) was added to a solution of tert-butyl (4-(hydroxymethyl)bicyclo[2.2.1]heptan-1-yl)carbamate (2.0 g, 8.3 mmol) and anhydrous CH$_2$Cl$_2$ (30 mL). The reaction was cooled to 0° C. and methansulfonyl chloride (2.0 mL, 25.0 mmol) was added and the mixture was stirred for 3 hours at room temperature. The reaction was diluted with CH$_2$Cl$_2$ (50 mL) and water (30 mL). The organic layer was separated, washed with brine (15 mL), dried over anhydrous MgSO$_4$, filtered and concentrated to dryness. The residue was purified flash column chromatography (petroleum ether/ethyl acetate, 5:1 to 1:1, gradient elution) to provide the title compound (2.58 g, 97%) as white solid. TLC (petroleum ether/ethyl acetate, 1:1), $R_f$=0.85. $^1$H NMR (400 MHz, CDCl$_3$) 4.73 (br s, 1H), 4.21 (s, 2H), 2.98 (s, 3H), 1.93-1.90 (m, 2H), 1.78-1.62 (m, 6H), 1.53-1.34 (m, 11H).

Step I: tert-Butyl (4-(cyanomethyl)bicyclo[2.2.1]heptan-1-yl)carbamate. To a solution of (4-((tert-butoxycarbonyl)amino)bicyclo[2.2.1]heptan-1-yl)methyl methanesulfonate (2.58 g, 8.07 mmol) and DMSO (25 mL) was added sodium cyanide (1.20 g, 24.5 mmol). The reaction was heated to 100° C. and stirred for 24 hours. The reaction was diluted with 50 mL of water and extracted with ethyl acetate (3×40 mL). The combined organic extracts were washed with brine (20 mL), dried over anhydrous Na$_2$SO$_4$, filtered, and concentrated to dryness. The residue was purified by flash column chromatography (petroleum ether/ethyl acetate, 5:1) to provide the title compound (1.8 g, 89% yield) as white solid. $^1$H NMR (400 MHz, DMSO-$d_6$): δ 7.00 (br s, 1H), 2.67 (s, 2H), 1.82 (br s, 2H), 1.69-1.52 (m, 6H), 1.47-1.40 (m, 2H), 1.37 (s, 9H).

Step J: 2-(4-Aminobicyclo[2.2.1]heptan-1-yl)acetonitrile hydrochloride. To a suspension of tert-butyl (4-(cyanomethyl)bicyclo[2.2.1]heptan-1-yl)carbamate (850 mg, 3.40 mmol) and ethyl acetate (2 mL) at 0° C. was added a solution of HCl in ethyl acetate (4.0 M, 10 mL, 40 mmol). After stirring at room temperature for 2 hours, the mixture was concentrated under reduced pressure to dryness. The residue was triturated with MTBE (5 mL) and the suspension was isolated via filtration. The filter cake was washed with MTBE (1 mL) and dried under reduced pressure to afford the title compound (450 mg, 71%) as a white solid. MS (ESI): mass calcd. for C$_9$H$_{14}$N$_2$ 150.12 m/z, found 151.1 [M+H]$^+$. $^1$H NMR (400 MHz, DMSO-$d_6$) δ 8.59 (br.s., 3H), 2.78 (s, 2H), 1.90-1.77 (m, 2H), 1.74-1.62 (m, 4H), 1.60 (s, 2H), 1.56-1.46 (m, 2H).

Step K: N-(4-(Cyanomethyl)bicyclo[2.2.1]heptan-1-yl)-2-(1-((1r,4r)-4-(cyanomethyl)cyclohexyl)-1,6-dihydroimidazo[4,5-d]pyrrolo[2,3-b]pyridin-2-yl)acetamide. To a solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 2-(4-aminobicyclo[2.2.1]heptan-1-yl)acetonitrile hydrochloride (138 mg, 0.918 mmol), and DIPEA (0.291 mL, 1.67 mmol) in dry DMF (6 mL) was added PyBrOP (428 mg, 0.918 mmol) at 0° C. The reaction was stirred at room-temperature for 12 h. The mixture was quenched with 10 mL water and was extracted with EtOAc (3×20 mL). The combined organic phases were washed with brine, dried over anhydrous Na$_2$SO$_4$, filtered, and concentrated to dryness. The residue was purified by preparative HPLC (using a Xtimate C$_{18}$ 150×25 mm×5 μm column (eluent: 23% to 33% (v/v) CH$_3$CN and H$_2$O with 10 mM NH$_4$HCO$_3$) and by preparative TLC (dichloromethane:methanol=15:1) to provide the title compound (36.6 mg, 9% yield) as a white solid. MS (ESI): mass calcd. for C$_{27}$H$_{31}$N$_7$O, 469.3; m/z found, 470.2 [M+H]$^+$. $^1$H NMR (400 MHz, CD$_3$OD): δ 8.53 (s, 1H), 7.48 (d, J=4.0 Hz, 1H), 6.84 (d, J=4.0 Hz, 1H), 4.47 (br s, 1H), 4.07-4.02 (m, 2H), 2.63 (s, 2H), 2.61-2.50 (m, 4H), 2.18-1.98 (m, 7H), 1.94-1.84 (m, 2H), 1.82 (s, 2H), 1.79-1.68 (m, 2H), 1.62-1.43 (m, 4H).

Example 11 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide

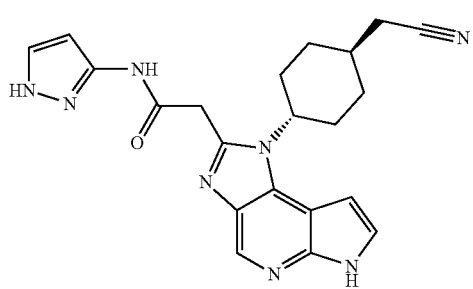

(Ex. 11)

Step A: 2-(1-((1r,4r)-4-(Cyanomethyl)cyclohexyl)-6-(phenylsulfonyl)-1,6-dihydroimidazo[4,5-d]pyrrolo[2,3-b]pyridin-2-yl)-N-(1H-pyrazol-3-yl)acetamide. The title compound (383 mg, 70%) was prepared in a manner analogous to that described in Example 1, Step A using 1H-pyrazol-3-amine (465 mg, 5.48 mmol) instead of 1-amino-2-methylpropan-2-ol. MS (ESI): mass calcd. for $C_{27}H_{26}N_8O_3S$, 542.2; m/z found, 543.2 $[M+H]^+$. $^1$H NMR (500 MHz, DMSO-$d_6$) δ 12.36 (s, 1H), 11.36 (s, 1H), 10.81 (s, 1H), 8.65 (s, 1H), 8.14-8.10 (m, 2H), 7.96 (d, J=4.1 Hz, 1H), 7.72-7.68 (m, 1H), 7.63-7.60 (m, 2H), 7.30 (s, 1H), 7.13 (d, J=4.2 Hz, 1H), 6.44-6.41 (m, 1H), 5.41 (s, 1H), 4.57 (s, 1H), 4.44 (s, 2H), 4.24 (s, 2H), 2.56 (d, J=6.2 Hz, 2H), 2.23-2.13 (m, 2H), 2.02-1.95 (m, 1H), 1.41-1.32 (m, 2H).

Step B: 2-(1-((1r,4r)-4-(Cyanomethyl)cyclohexyl)-1,6-dihydroimidazo[4,5-d]pyrrolo[2,3-b]pyridin-2-yl)-N-(1H-pyrazol-3-yl)acetamide. The title compound was prepared in a manner analogous to Example 1, Step B using 2-(1-((1r,4r)-4-(cyanomethyl)cyclohexyl)-6-(phenyl sulfonyl)-1,6-dihydroimidazo[4,5-d]pyrrolo[2,3-b]pyridin-2-yl)-N-(1H-pyrazol-3-yl)acetamide (270 mg, 0.500 mmol) instead of 2-(1-((1r,4r)-4-(cyanomethyl)cyclohexyl)-6-(phenyl sulfonyl)-1,6-dihydroimidazo[4,5-d]pyrrolo[2,3-b]pyridin-2-yl)-N-(2-hydroxy-2-methylpropyl)acetamide and purified by basic HPLC using a Xbridge Prep OBD C18 150 mm×30 mm, 5 µm, eluent 5% ACN/NH$_4$OH (aq) (10 min) to provide the title compound (15 mg, 7%). MS (ESI): mass calcd. for $C_{21}H_{22}N_8O$, 402.5; m/z found, 403.2 $[M+H]^+$. $^1$H NMR (500 MHz, DMSO-$d_6$): δ 12.35 (s, 1H), 11.85 (s, 1H), 10.84 (s, 1H), 8.50 (s, 1H), 7.58 (d, J=2.3 Hz, 1H), 7.46 (d, J=3.4 Hz, 1H), 6.72 (d, J=3.5 Hz, 1H), 6.47-6.39 (m, 1H), 4.64-4.46 (m, 1H), 4.21 (s, 2H), 2.57 (d, J=6.1 Hz, 2H), 2.45-2.26 (m, 2H), 2.08-1.88 (m, 5H), 1.39 (q, J=11.7 Hz, 2H).

Example 12 Synthesis and Characterization 2-(1-((1r,4r)-4-(Cyanomethyl)cyclohexyl)-1,6-dihydroimidazo[4,5-d]pyrrolo[2,3-b]pyridin-2-yl)-N-((1-hydroxycyclopropyl)methyl)acetamide

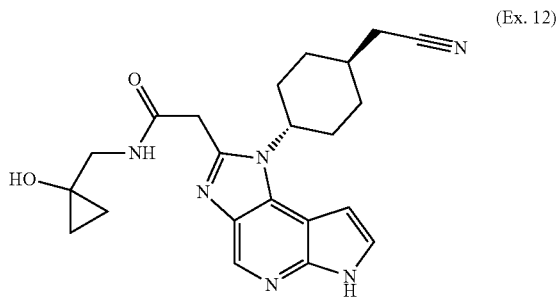 [SMILES: N#CC[C@H]1CC[C@H](n2c(CC(=O)NCC3(O)CC3)nc3cnc4[nH]ccc4c32)CC1]

(Ex. 12)

A solution of sodium 2-(1-((1r,4r)-4-(cyanomethyl)cyclohexyl)-1,6-dihydroimidazo[4,5-d]pyrrolo[2,3-b]pyridin-2-yl)acetate (Intermediate 4, 300 mg, 0.835 mmol), 1-(aminomethyl)cyclopropanol (72.7 mg, 0.835 mmol), DIPEA (216 mg, 1.67 mmol), and DMF (5 mL) was stirred at 0° C. for 1 h. Then PyBrOP (467 mg, 1.00 mmol) was added and stirred at room-temperature overnight. The mixture was quenched with 10 mL water and was purified by preparative basic HPLC using a Kromasil 150 mm×25 mm, 10 µm column (eluent: water (0.05% ammonia hydroxide v/v)-ACN from 5% to 35%, v/v) to provide the title compound (84 mg, 25% yield) as a white solid. MS (ESI): mass calcd. for $C_{22}H_{26}N_6O_2$, 406.21; m/z found, 407.2 $[M+H]^+$. $^1$H NMR (400 MHz, DMSO-$d_6$): δ 11.53 (br s, 1H), 8.50 (s, 1H), 8.03-7.93 (m, 1H), 7.44-7.40 (m, 1H), 6.74-6.71 (m, 1H), 5.04 (s, 1H), 4.58-4.49 (m, 1H), 4.02 (s, 2H), 3.29 (d, J=6.0 Hz, 2H), 2.55 (d, J=6.0 Hz, 2H), 2.45-2.31 (m, 2H), 2.10-1.97 (m, 5H), 1.50-1.37 (m, 2H), 0.62-0.55 (m, 2H), 0.55-0.48 (m, 2H).

Polymorph Screening Example

Some embodiments of compounds according to this invention as free bases present multiple crystalline configurations that have a complex solid-state behavior, some of which in turn can present distinguishing features among themselves due to different amounts of incorporated solvent. Some embodiments of compounds according to this invention are in the form of pseudopolymorphs, which are embodiments of the same compound that present crystal lattice compositional differences due to different amounts of solvent in the crystal lattice itself. In addition, channel solvation can also be present in some crystalline embodiments of compounds according to this invention, in which solvent is incorporated within channels or voids that are present in the crystal lattice. For example, various crystalline configurations including those given in Table 2, were found for compound Ex. 1. Because of these features, non-stoichiometric solvates were often observed, as illustrated in Table 2. Furthermore, the presence of such channels or voids in the crystal structure of some embodiments according to this invention enables the presence of water and/or solvent molecules that are held within the crystal structure with varying degrees of bonding strength. Consequently, changes in the specific ambient conditions can readily lead to some loss or gain of water molecules and/or solvent molecules in some embodiments according to this invention. It is understood that "solvation" (third column in Table 2) for each of the embodiments listed in Table 2 is the formula solvation, and that the actual determination of the same as a stoichiometry number (fourth column in Table 2) can slightly vary from the formula solvation depending on the actual ambient conditions when it is experimentally determined. For example, if about half of the water molecules in an embodiment may be present as hydrogen-bonded to the active compound in the crystal lattice, while about the other half of water molecules may be in channels or voids in the crystal lattice, then changes in ambient conditions may alter the amount of such loosely contained water molecules in voids or channels, and hence lead to a slight difference between the formula solvation that is assigned according to, for example, single crystal diffraction, and the stoichiometry that is determined by, for example, thermogravimetric analysis coupled with mass spectroscopy. Features of compounds according to this invention, such as formula solvation and stoichiometry, are determined, once each of such embodiments is made, by techniques such as single crystal diffraction, and thermogravimetric analysis coupled with mass spectroscopy.

TABLE 2

Some embodiments of crystalline forms of compound Ex. 1

| Embodiment | Crystallization solvent | Solvation | Stoichiometry |
|---|---|---|---|
| 1s | — | monohydrate | 0.8 H$_2$O |
| 1a | Water | monohydrate | 1.3 H$_2$O |
| 1b | Toluene | Toluene solvate | 0.4 toluene |
| 1c | Ethyl acetate/ 1,4-dioxane | monohydrate | 1.1 H$_2$O |

TABLE 2-continued

Some embodiments of crystalline forms of compound Ex. 1

| Embodiment | Crystallization solvent | Solvation | Stoichiometry |
|---|---|---|---|
| 1d | Acetonitrile/chloroform | 1.7 hydrate | 1.7 $H_2O$ |
| 1e | Ethyl acetate/1,4-dioxane | monohydrate | 1 $H_2O$ |
| 1f | p-xylene | p-xylene solvate | 0.3 p-xylene |
| 1f | Cumene | Cumene solvate | 0.3 cumene |
| 1g | Anisole | Anisole solvate | 0.3 anisole |
| 1h | p-xylene | p-xylene solvate | 0.2 p-xylene |
| 2 | 1,4-dioxane | 1,4-dioxane solvate | 1.2 1,4-dioxane |
| 3b | Cyclohexanone | Cyclohexanone solvate | 0.3 Cyclohexanone |
| 3c | 1,4-dioxane | 1,4-dioxane solvate | 0.5 1,4-dioxane |
| 3d | THF | THF solvate | 0.4 THF |
| 3e | Isobutanol | Isobutanol solvate | 0.7 isobutanol |
| 1b + 4 | Water/methanol | Mix hydrate/methanol solvate | — |
| 5 | Chloroform | Chloroform solvate | 0.5 chloroform |
| 6 | Acetonitrile | Anhydrous | 0.2 acetonitrile |
| 1s + 7 | Heptane | Heptane solvate | 0.1 heptane |
| 7 | — | Non-solvated | — |
| 8 | — | Non-solvated | — |
| 9 | — | Non-solvated | — |
| 10 | | dihydrate | 1.8 $H_2O$ |
| 11 | ethanol | ethanol solvate | 0.5 ethanol |
| 11b | methanol | methanol solvate | 0.5 methanol |
| 12 | — | anhydrous | — |
| 13 | methanol/water | metastable form | |
| 14 | | metastable hydrate | |
| 15 | toluene | toluene solvate | 0.55 toluene |
| 16 | ethyl acetate | ethyl acetate solvate | 0.09 ethyl acetate |
| 17 | isopropyl acetate | isopropyl acetate solvate | 0.13 isopropyl acetate |
| 18 | 2-butanone | 2-butanone solvate | 0.2 2-butanone |

The compound that was obtained as described in Example 1 was further crystallized by preparing a slurry in DCM (1:3, for example 10 g of compound in 30 ml DCM) that was stirred at 40° C. for 4 hours, and further stirred for 14 hours at 25° C., then heptane was slowly added (1:2, for example 20 ml of heptane into the compound/DCM slurry/solution) at 25° C., stirred at 40° C. for 4 hours, cooled to 25° C. and stirred for further 14 hours at 25° C. Subsequent filtration lead to compound Ex. 1 in the form of an off-white solid, that was identified as a monohydrate, a 1s embodiment.

An amorphous form of compound Ex. 1, embodiment 19, was prepared as follows. Embodiment 1s (1 g) was dissolved in t-butanol (40 vol) and stirred at 50° C. Pre-dried molecular sieves were added to the solution and stirred for 10 min. The solution was filtered and aliquoted into HPLC vials (1 ml) which were frozen in a dry ice-acetone bath right afterwards. Samples were then placed on the freeze drier for 48 h. The material was amorphous by XRPD and consistent with the proposed structure by $^1$H-NMR, with 0.4 mol of t-butanol per molecule of compound Ex. 1 present. This material was heated to 150° C. and held at 150° C. for 10 min. The final sample was analyzed by XRPD and $^1$H-NMR and it was determined to be amorphous and that 0.03 mol of t-butanol remained per molecule of compound Ex. 1.

Figure 2:
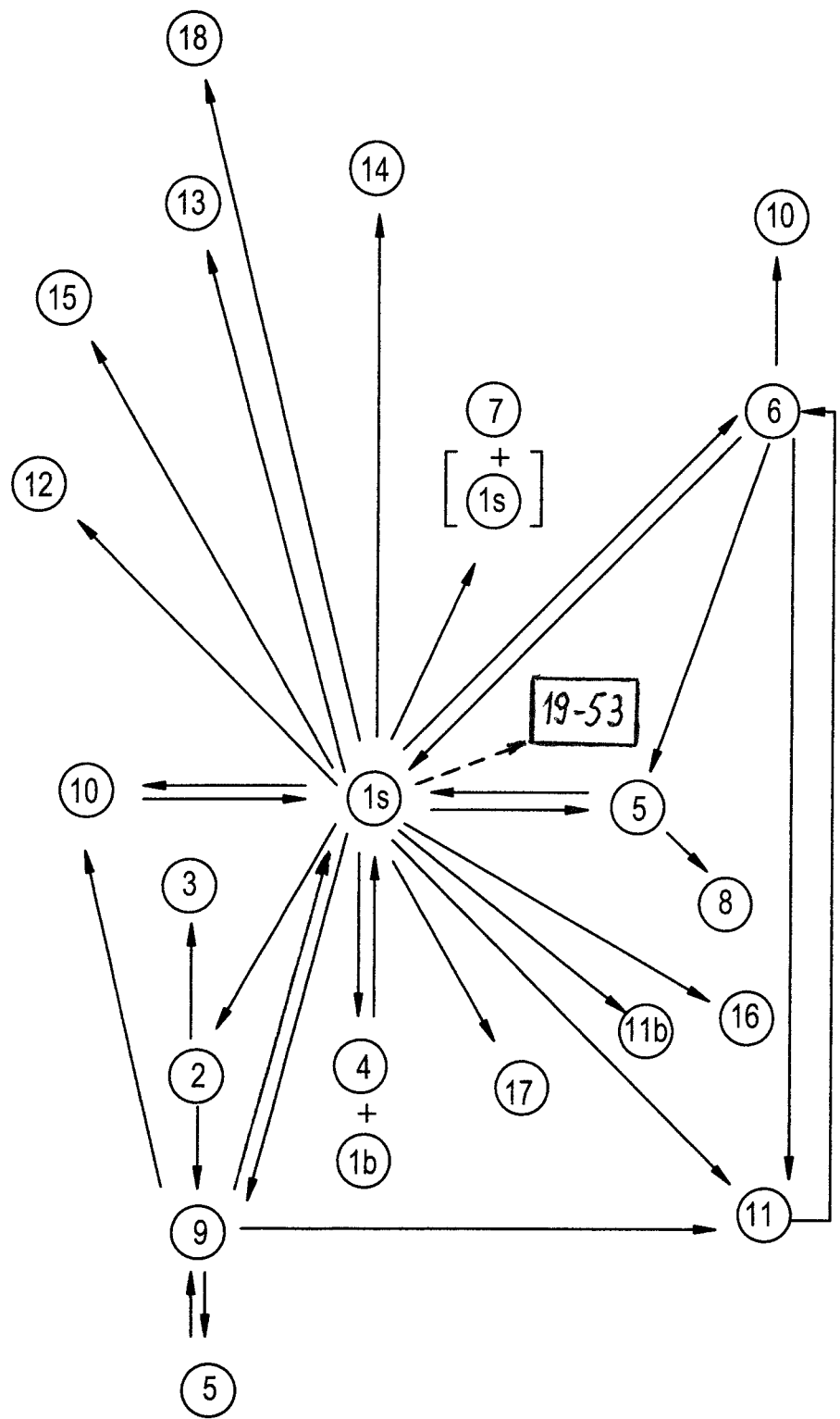

Embodiments 1-18 in Table 2 and FIG. 2 are crystalline, and embodiment 19 in FIG. 2 is amorphous. Embodiments is and 1a through 1h are isostructural. Embodiment 1s crystallizes in a centro-symmetrical triclinic space group P-1. The term "embodiment 1" collectively refers to the isostructural embodiments is and 1a through 1h. Any one of such is and 1a through 1h embodiments is sometimes referred to as an isostructural member of embodiment 1 or just as a member of embodiment 1. Embodiments 3b, 3c, 3d and 3e are isostructural and crystallize in the monoclinic system, space group C 2/c. The term "embodiment 3" collectively refers to the isostructural embodiments 3b, 3c, 3d and 3e. Any one of such 3b, 3c, 3d and 3e embodiments is sometimes referred to as an isostructural member of embodiment 3 or just as a member of embodiment 3. Isostructural embodiments are such that they possess similar crystal structure properties (same symmetries and similar unit cell parameters and crystal packing) while having different chemical compositions (i.e., different solvent and/or water molecules incorporated in the crystal lattice). Unit cell parameters in isostructural embodiments can slightly differ due to the different composition (solvent or water incorporated into the crystal structure). Embodiments referred to in Table 2 were prepared and/or inter-converted as schematically shown in FIG. 2 and as described in more detail as follows.

Crystallization protocols used in these preparations included solvent equilibration in neat solvents, evaporative crystallization, cooling crystallization with hot filtration, crash-crystallization with anti-solvent, crystallization by thermocycling, incubation at low temperature, heat/cool maturation, incubation at elevated temperature, high temperature maturation using amorphous material (embodiment 19), and thermocycling using amorphous material (embodiment 19). Solids were analyzed by HT-XRPD or XRPD. When applicable, mother liquors were evaporated completely and the remaining solids were also analyzed by HT-XRPD or XRPD. The starting material embodiment 1s as a monohydrate was a predominant solid form.

Solvent Equilibration at 25° C. and 50° C.

Long term slurry experiments were performed by suspending compound embodiment 1s in twenty neat solvents and stirring at room temperature for two weeks and at 50° C. for one week. Upon completion of the equilibration time, the residual solids were separated from the mother liquors. The solids were dried under ambient conditions and dried under vacuum (5 mBar) before being analyzed by HT-XRPD. Subsequently, the solids were exposed to accelerated aging conditions (40° C./70% relative humidity) for two days and again analyzed by HT-XRPD.

From most of the crystallization solvents, the starting material as embodiment 1s was obtained. From several crystallization solvents, HT-XRPD patterns were found to be similar to those of the initial embodiment 1s. In most of these diffraction patterns, peak shifts and/or additional peaks were identified. Each of these patterns corresponded to an embodiment that was labeled as one of 1a through 1h, and based on the similarities in the HT-XRPD diffraction patterns for such embodiments, they are presented as embodiments that are isostructural members of embodiment 1. All isostructural members of embodiment 1 converted to embodiment 1a after exposure to 40° C. and 75% RH for two days.

Figure 6:
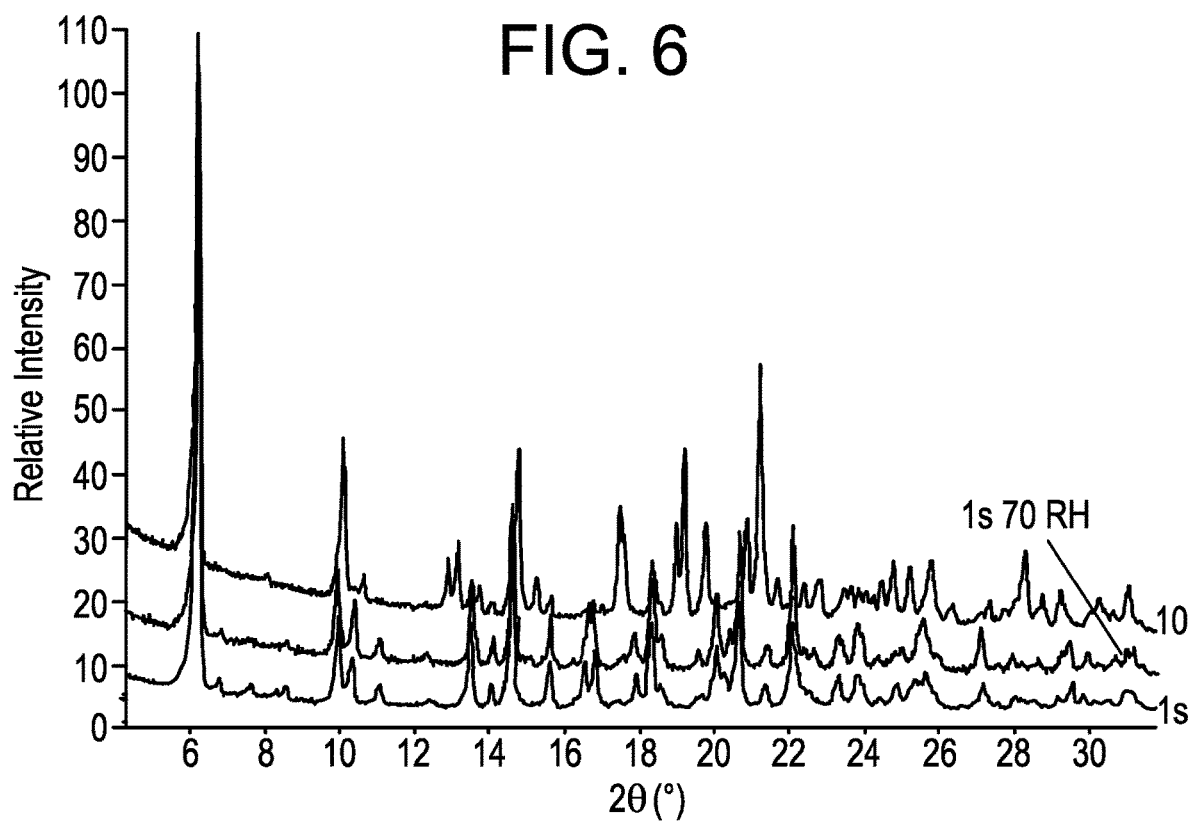

Embodiment 1s converted to hydrated embodiment 10 when it was exposed to 100% RH at 25° C. Nevertheless, embodiment 10 was physically not stable at ambient conditions. Whereas embodiment 1s crystallized in the triclinic system, space group P-1, embodiment 10 was found to crystallize in the monoclinic system, space group C 2/c. Embodiment 10 had limited physical stability under ambient conditions and it converted to another embodiment such as 1s or 1a. This behavior is attributable to an unequally strong binding of all the hydration/solvation molecules. In this case, embodiment 10 would have a less strongly bound second water molecule that would be lost under ambient conditions. More precisely, the physical stability of embodiment 1s was investigated in climate chambers by exposing a 20 mg sample of such embodiment to 40° C. and 70% relative humidity for four days, and another 20 mg sample of the same embodiment was exposed also for four days to 25° C. and 100% relative humidity. After four days, the various solid samples were analyzed by HR-XRPD, the crystal cell parameters were determined and the diffractograms were indexed. Diffractograms are shown in FIG. 6. From bottom to top, the first diffractogram in FIG. 6 corresponds to embodiment 1s as starting material, and the second corresponds to the same form after a 4-day exposure to 40° C. and 70% relative humidity, noted as "1s 70 RH" in the same figure. This analysis revealed that the initial embodiment 1s had been recovered although with a small amount of a second crystalline form that was possibly another hydrated embodiment with a higher water content. Indexing for such form was not possible due to the small amount in which it was present. The third diffractogram corresponds to embodiment 1s after a 4-day exposure to 25° C. and 100% relative humidity, noted as "10" in the same figure. These conditions lead to the conversion of embodiment 1s into embodiment 10, with a small contamination of initial embodiment 1s, and solvation as characterized in Table 2. Upon dehydration, both embodiments is and 10 re-crystallized to the anhydrous form with a melting point of 148° C.

Embodiment 10 was also prepared by slurry conversion of embodiment 1s or embodiment 19 in water, with temperature cycling of 25-5° C. The slurry was prepared by suspending 50 mg of material in 1 mL water. Temperature cycling of 25-5° C. is: the mixture was heated at 25° C. for 1 hour and then the temperature was decreased to 5° C. over a 2 hour period. The mixture was then held at a temperature of 5° C. for 1 hour. The temperature was then increased to 25° C. over a 2 hour period. This temperature cycling regime was repeated for a total of about 24 hours. The solids were isolated by vacuum filtration and then dried on a filter for 10 minutes. Embodiment 10 converted to embodiment 1s during drying under ambient conditions and under vacuum.

Solvent equilibration at room temperature yielded embodiment 1b out of toluene as the crystallization solvent, and embodiment 1f out of p-xylene as the crystallization solvent.

Figure 21A:
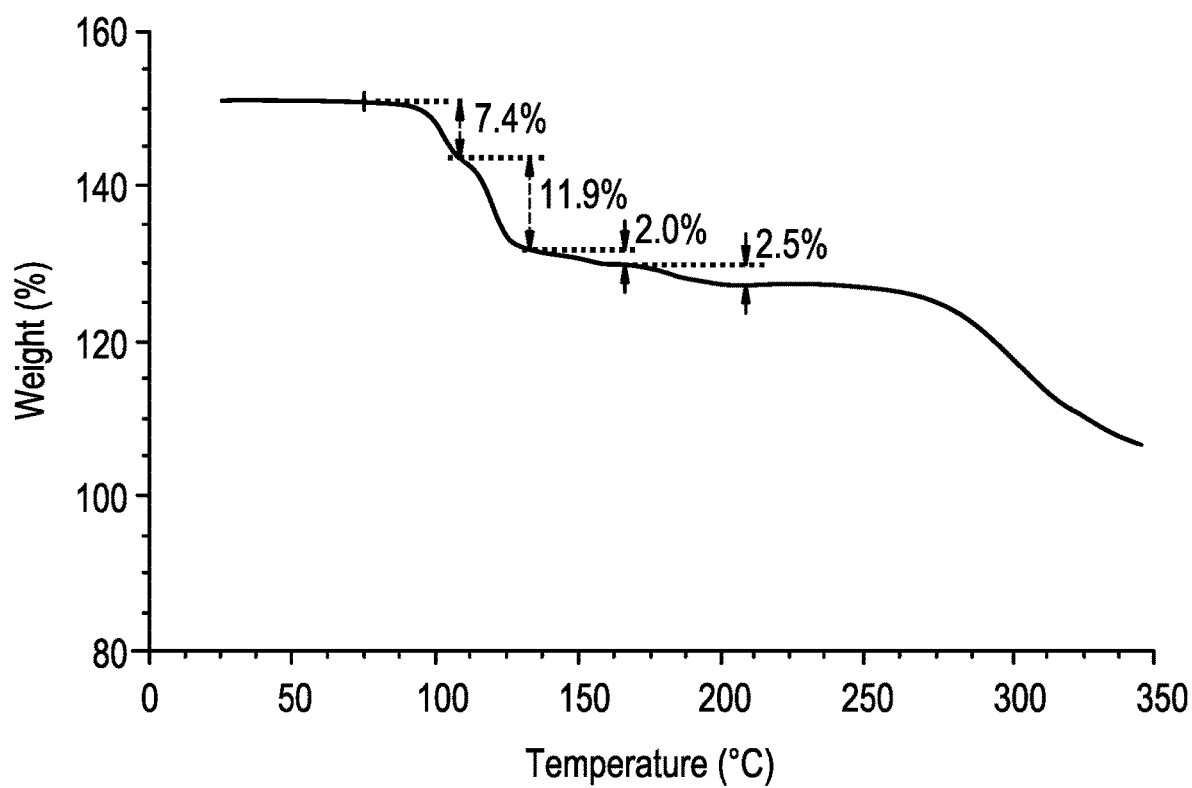
Figure 21B:
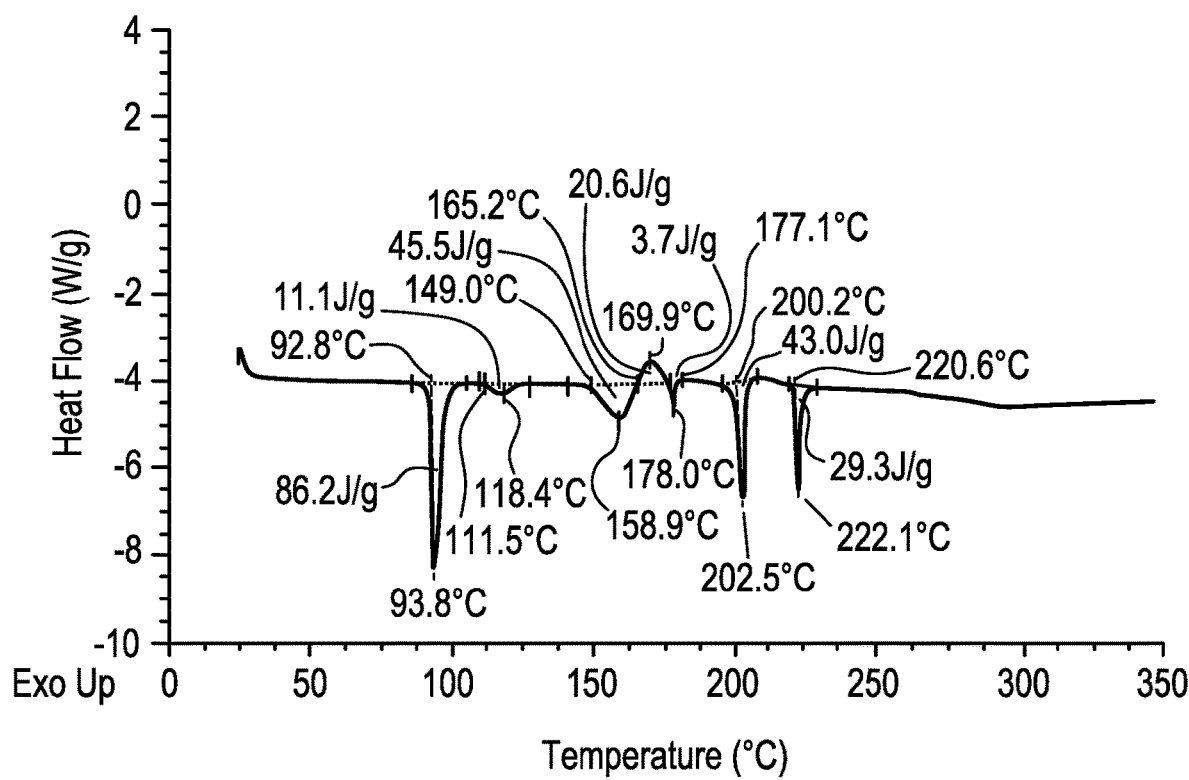

Three additional solid embodiments were identified and designated as embodiments 2, 3 and 7. Embodiment 2, whose TGA and DSC are shown in FIGS. 21A and 21B, respectively, was identified from the solvent equilibration experiment performed at room temperature in 1,4-dioxane while embodiment 7 was found as a mixture with embodiment 1s in the single solvent equilibration experiment at 50° C. from heptane. Several similar but not identical diffractograms were identified which were grouped as embodiments 3b, 3c, 3d and 3e that are isostructural members of embodiment 3. Isostructural members of embodiment 3 were found mixed with members of embodiment 1. The mixtures containing members of embodiment 3 transformed in some cases to embodiment 1a or to mixtures of embodiments 1a and 3e. Embodiment 7 appeared to be physically stable, but embodiment 2 converted to embodiment 3e after exposure to AAC for two days.

Evaporative Crystallization

The mother liquors saved from the solvent equilibration experiments performed at RT were used for slow evaporative crystallization experiments. The mother liquors were filtered to remove any particulate matter and allowed to slowly evaporate under ambient conditions. The obtained solids were analyzed by HT-XRPD and again after exposure to AAC for two days. Due to the poor solubility of compound Ex. 1 in some of the solvents, no solids were recovered when such solvents were used. In the experiments where solids had precipitated, an amorphous residue or isostructural members of embodiments 1 or 3 were recovered. During the stability study, the different members of embodiment 1 converted to embodiment 1a whilst the sample of embodiment 3 seemed to be physically stable. The amorphous solids in some cases remained amorphous after the stability study, became deliquescent or showed some signs of crystallinity.

Cooling Crystallization

The mother liquors of the solvent equilibration experiments performed at 50° C. were filtered at 50° C. to remove any particulate matter. The suspensions at 50° C. were filtered using 0.2 μm PTFE filters, and the solutions were placed at 5° C. and aged for 72 hours. When solids had precipitated during aging these solids were separated from the liquid, dried under ambient conditions and under vacuum, and analyzed by HT-XRPD. The remaining mother liquors were allowed to slowly evaporate and the remaining solids were analyzed by HT-XRPD. The samples in which no precipitation occurred were placed under vacuum and the dried solids were analyzed by HT-XRPD. All the solids were then exposed to AAC (2 days at 40° C./70% RH) and re-analyzed by HT-XRPD.

Solids did not precipitate upon cooling in some of the solutions, in which cases the solutions were evaporated under ambient conditions. Due to the low solubility of compound Ex. 1 in some solvents, no solids were obtained from some solutions.

From four solvents (2-propanol, 2-butanone, acetonitrile, and methanol), precipitation occurred. Embodiment 6 was identified after evaporation of a single cooling crystallization experiment at mL scale in 800 μL acetonitrile, concentration of 25 mg/mL. Embodiment 6 seemed to be a stable solid form after 2 days AAC, and it appeared as a non-solvated embodiment.

Cooling/Evaporative Crystallization at μL Scale

The cooling/evaporative crystallization experiments at μL scale were performed in a 96-well plate, using 12 neat solvents and 12 solvent mixtures and applying four temperature profiles. In each well approximately 4 mg of embodiment 1s was solid dosed. Subsequently, the crystallization solvents (80 μL) and solvent mixtures were added to reach a concentration of 50 mg/mL, and the plate, with each well individually sealed, to subsequently undergo one of the four temperature profiles. Upon completion of the temperature profile the solvents were allowed to evaporate at low ambient pressure (24 hours) and the remaining solids were analyzed by HT-XRPD before and after exposure to AAC for 2 days (40° C./70% RH).

Members of embodiments 1 and 3 were found from most of the solvent systems and temperature profiles. However, a certain tendency of solid form versus temperature profile was observed. Embodiment 1b was mainly identified from the short temperature profiles (3 hours aging). Nevertheless, the same solvent systems with long aging times led to the identification of embodiment 1f, members of embodiment 3 or mixtures of members of embodiments 1 and 3. Embodiment 3c was obtained with 1,4-dioxane as crystallization solvent and a temperature profile of 50° C. as initial temperature, held for 60 min, followed by cooling at a rate of 1° C./h to a final temperature of 20° C., held for 48 h; embodiment 3d was obtained with tetrahydrofuran as crystallization solvent and the same temperature profile as for embodiment 3c.

Embodiment 4 was identified in experiments performed in methanol/water (50/50, v/v), THF and DCM/IPA (50/50, v/v) when short aging conditions were applied. Embodiment 4 was obtained by treating embodiment 1s with a mixture (50/50) of water and methanol and a temperature profile of 50° C. as initial temperature, held for 60 min, followed by cooling at a rate of 20° C./h to a final temperature of 5° C., held for 3 h, which yielded embodiment 4 together with embodiment 1b. Embodiment 4 together with embodiment 1b was also obtained by treating is with a mixture (50/50) of water and methanol and a temperature profile of 50° C. as initial temperature, held for 60 min, followed by cooling at a rate of 20° C./h to a final temperature of 20° C., held for 3 h. Embodiment 4 did not appear to be physically stable under ambient conditions. Cooling crystallization experiments yielded embodiment 1c out of ethyl acetate/1,4-dioxane (50/50, v/v) as the crystallization solvent and a temperature profile of 50° C. as initial temperature, held for 60 min, followed by cooling at a rate of 1° C./h to a final temperature of 5° C., held for 48 h; embodiment 1d out of acetonitrile/chloroform (50/50, v/v) as the crystallization solvent and a temperature profile of 50° C. as initial temperature, held for 60 min, followed by cooling at a rate of 1° C./h to a final temperature of 5° C., held for 48 h; and embodiment 1e out of ethyl acetate/1,4-dioxane (50/50, v/v) as the crystallization solvent and a temperature profile of 50° C. as initial temperature, held for 60 min, followed by cooling at a rate of 1° C./h to a final temperature of 20° C., held for 48 h.

Embodiment 5 was identified in experiments performed in chloroform as the crystallization solvent and a temperature profile of 50° C. as initial temperature, held for 60 min, followed by cooling at a rate of 1° C./h to a final temperature of 20° C., held for 48 h.

Similar conversions were seen during the stability study as previously observed in the other crystallization methods. In most cases all solid forms converted to embodiment 1a or to mixtures containing embodiment 1a.

Evaporative Crystallization from Solid Mixtures

In evaporative crystallization using solvent/anti-solvent mixtures, clear solutions of a compound are prepared from which the solvent evaporates first (high vapor pressure) causing the compound to precipitate to some extent in the form of crystals. These crystals then act as seeds when the anti-solvent (lower vapor pressure) is evaporated.

Compound Ex. 1 did not completely dissolve in each of the solvent systems. For that reason, all the experiments included filtration prior to evaporation.

The results of the HT-XRPD analysis demonstrated that compound Ex. 1 crystallized mainly as embodiment 1s upon evaporation of solvent mixtures. This was observed for the following solvent/anti-solvent systems: tetrahydrofuran/water, acetonitrile/water, chloroform/ethanol, methanol/ethyl acetate, 2-butanone/isopropanol, and heptane/acetone. From two systems, acetone/cumene and 1,4-dioxane/ethyl formate, the isostructural embodiments 3b and 3e were identified, which after AAC converted to different mixtures of embodiments 1a and 3d, and is and 3e, respectively.

Anti-Solvent Crystallization

Saturated solutions of compound Ex. 1 were prepared in neat solvents. The anti-solvent additions were performed in forward and reverse additions. In the forward addition, the anti-solvent was added in three aliquots to the compound solution. The reverse addition was performed by adding a volume of compound solution to a large excess of anti-solvent (20 mL).

After precipitation, the solids were separated from the liquids, dried under ambient conditions and dried under vacuum (5 mbar) before being analyzed by HT-XRPD. The experiments in which no precipitation occurred upon anti-solvent addition were stored at 5° C. for 48 hours to induce precipitation. The precipitated solids were afterwards separated and analyzed by HT-XRPD. When no solids were obtained, the solutions were evaporated under mild conditions and the residual solids were analyzed by HT-XRPD. All solids were exposed to AAC (2 days at 40° C./70% RH) and were re-analyzed by HT-XRPD.

The forward anti-solvent crystallization showed precipitation in all cases. All solids could be classified as isostructural members (1s, 1b, 1j, 1f) of embodiment 1 or of embodiment 3 (3b, 3d, 3f). After exposure to AAC, all solid samples converted to embodiment 1a, except one that converted to a mixture of embodiments 1a and 3e.

The reverse anti-solvent crystallization experiments performed in DMSO as solvent gave different solid forms depending on the anti-solvent used. With dichloromethane or p-xylene isostructural members (1s and 1b) of embodiment 1 were identified, while with MTBE an amorphous residue was obtained. Evaporation of two solutions with heptane and water as anti-solvents that had no precipitated upon anti-solvent addition led to an oil. Conversions to embodiment 1a were observed after AAC, and the amorphous residues became deliquescent.

Hot Filtration Experiments

The cooling crystallization experiments with hot filtration were performed from supersaturated solutions of compound Ex. 1 prepared at 50° C. in different solvent mixtures. The hot filtrated solutions underwent a 48-hour cooling profile. The vials in which solids had precipitated after the temperature profile were centrifuged and the solids were separated from the liquid and analyzed by HT-XRPD (after drying under vacuum). If no solids had precipitated the solutions were evaporated under vacuum and the solids analyzed by HT-XRPD. All the solids were exposed to AAC (2 days at 40° C./70% RH) and re-analyzed by HT-XRPD. In half of the hot filtration experiments precipitation did not occur and upon evaporation of the solvents, not enough solids were recovered due to the poor solubility of compound Ex. 1 in those solvent systems. In three experiments, an amorphous residue was recovered which after AAC crystallized to a mixture of members of embodiment 1 (1s or 1a) and 3 (3e) or became deliquescent. Embodiment 5 was identified from the experiment in acetone/chloroform (50/50, v/v). This embodiment appeared to be physically unstable as conversion to embodiment 1a was observed after AAC.

Thermo-Cycling Experiments

Suspensions of about 6 mg of embodiment 1s were prepared in 10 solvents at room temperature. The suspensions were cycled between 5° C. and 50° C. Upon completion of the thermo-cycling, the solids were separated by centrifugation and dried under ambient conditions and under vacuum (5 mbar) before being analyzed by HT-XRPD. Subsequently, all solids were exposed to AAC for two days and again analyzed by HT-XRPD. Thermo-cycling experiments usually promote the formation of the more stable polymorphic form. With the exception of the experiment performed in cyclohexanone all vials contained solids after the thermo profile. The cyclohexanone solution was slowly evaporated under mild vacuum. Members of embodiments 1, 3 or mixtures of them were identified mainly in the wet solids. Upon drying these solids, conversion to embodiment 1s was observed. Embodiments 3b and 3e were obtained from thermo-cycling in 300 μL of cyclohexanone at a concentration of 51 mg/mL (3b), and in 400 µL of isobutanol at a concentration of 37.3 mg/mL (3e). Embodiment 5 was obtained from thermo-cycling in 800 µL of chloroform at a concentration of 18.6 mg/mL.

Figure 3:
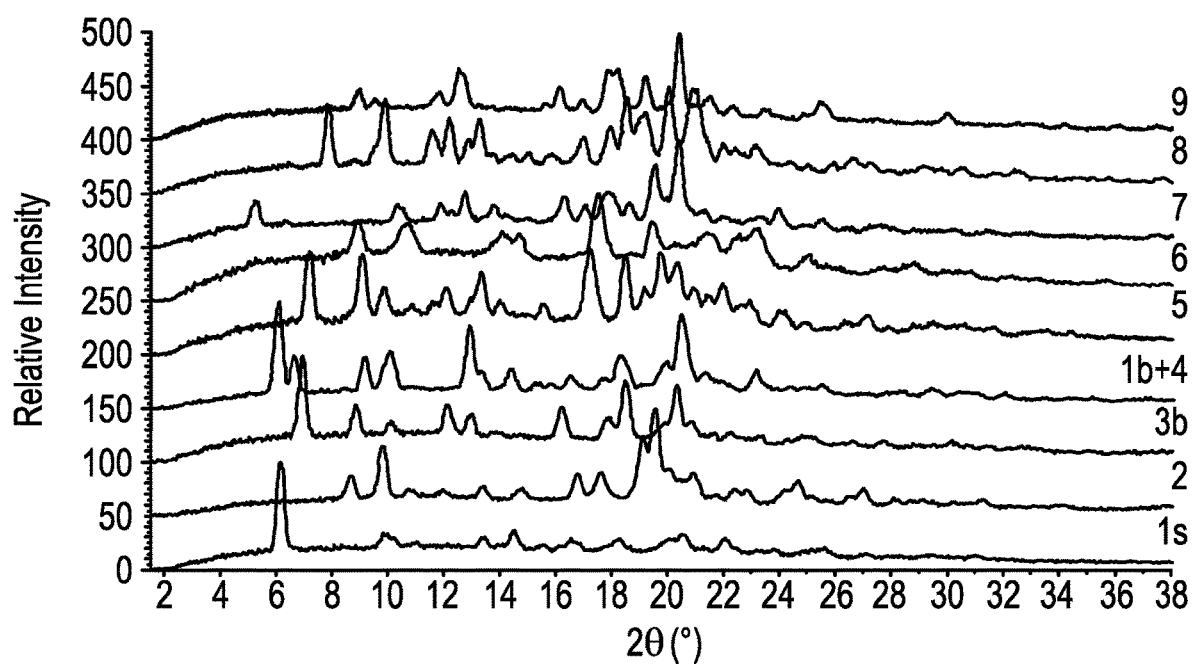
Figure 4:
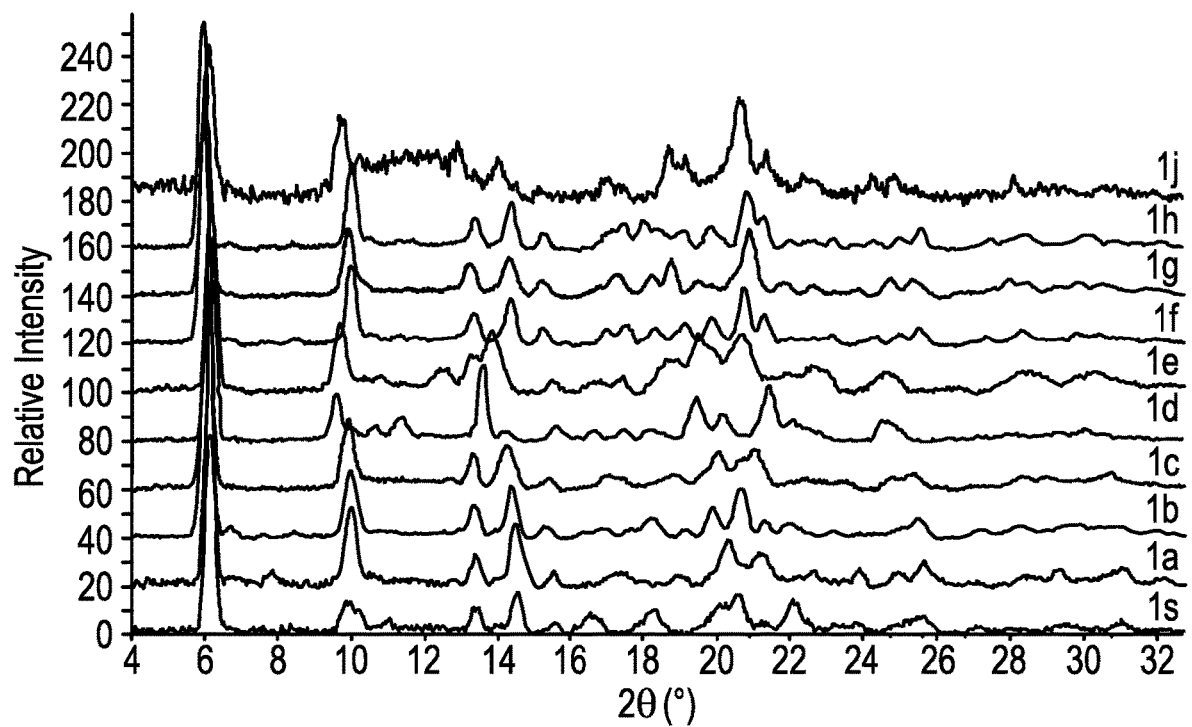
Figure 5:
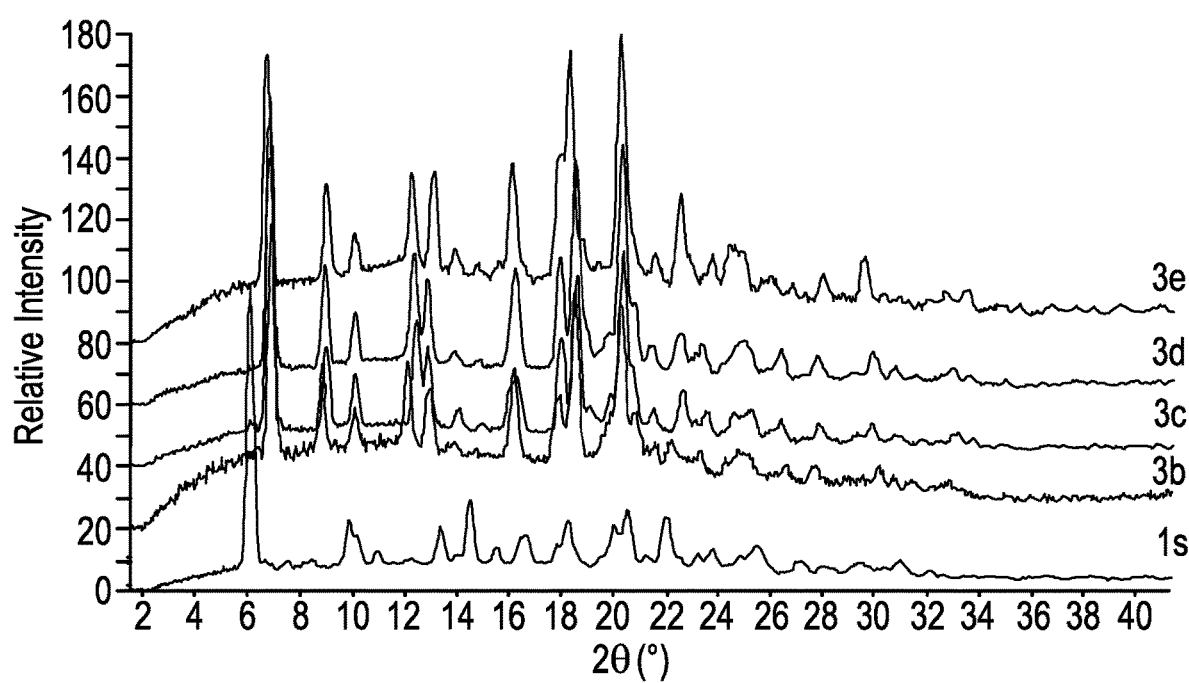

FIGS. 3, 4 and 5 show an overlay of HT-XRPD patterns for some of the embodiments listed in Table 2 and also referred to in the screenings described above.

Embodiment 1s was recovered from most of the crystallization experiments. It is a channel hydrate having a variable number of water molecules and/or other solvents incorporated depending on ambient conditions. Conversion to embodiment 1a was observed. This form contained slightly more water (1.3 molecules of water). All isostructural members of embodiment 1 converted to embodiment 1a after exposure to 40° C. and 75% RH for two days. The shifts of some diffraction peaks in XRPD patterns for members of embodiment 1 might be attributed to the different solvent or water molecules that were incorporated into the crystal lattice. FIG. 4 shows an overlay of HT-XRPD patterns for members of embodiment 1. Diffractogram 1s corresponds to compound Ex. 1 as starting material in the form of embodiment 1s. Diffractogram 1a corresponds to embodiment 1a that was obtained after exposure to AAC of several embodiment 1s samples. Diffractogram 1b corresponds to embodiment 1b that was obtained from the solvent equilibration experiment at RT in toluene. Diffractogram 1c corresponds to embodiment 1c that was obtained from the cooling crystallization experiment at µL scale in ethyl acetate/1,4-dioxane (50/50, v/v). Diffractogram 1c corresponds to embodiment 1d that was obtained from the cooling crystallization experiment at µL scale in acetonitrile/chloroform (50/50, v/v). Diffractogram 1e corresponds to embodiment 1e that was obtained from the cooling crystallization experiment at µL scale in ethyl acetate/1,4-dioxane (50/50, v/v). Diffractogram 1f corresponds to embodiment 1f that was obtained from the solvent equilibration experiment at RT in p-xylene. Diffractogram 1g corresponds to embodiment 1g that was obtained from the solvent equilibration experiment at 50° C. in anisole. Diffractogram 1h corresponds to embodiment 1h obtained from the cooling crystallization experiment at µL scale in p-xylene.

Diffractograms for members of embodiment 3 are shown in FIG. 5. The shifts observed in the different HT-XRPD patterns are most likely attributed to the different solvent molecules that were incorporated into the crystal lattice. Embodiment 3 was obtained by heating embodiment 2 to 40° C. at 70% RH for 4 days. Embodiments 3b through 3e were solvated forms containing a non-stoichiometric amount of solvent which varied depending on the solvent incorporated in the crystal structure (0.3-0.7 molecules). The mixtures containing members of embodiment 3 were unstable upon exposure to AAC and they transformed in some cases to embodiment 1a or to mixtures of embodiments 1a and 3e. Conversion to embodiment 1a is attributed to the exchange of solvent molecules by water molecules upon exposure to high relative humidity, and re-crystallization to the hydrated embodiment 1a.

Figure 22A:
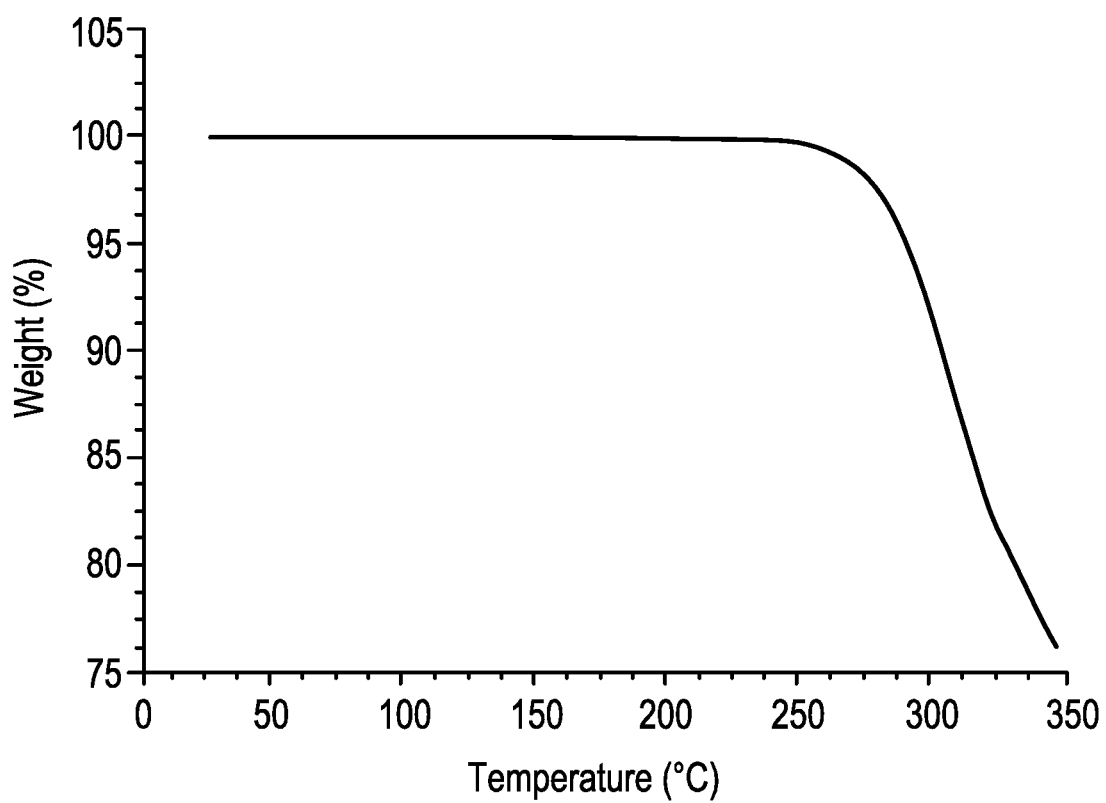
Figure 22B:
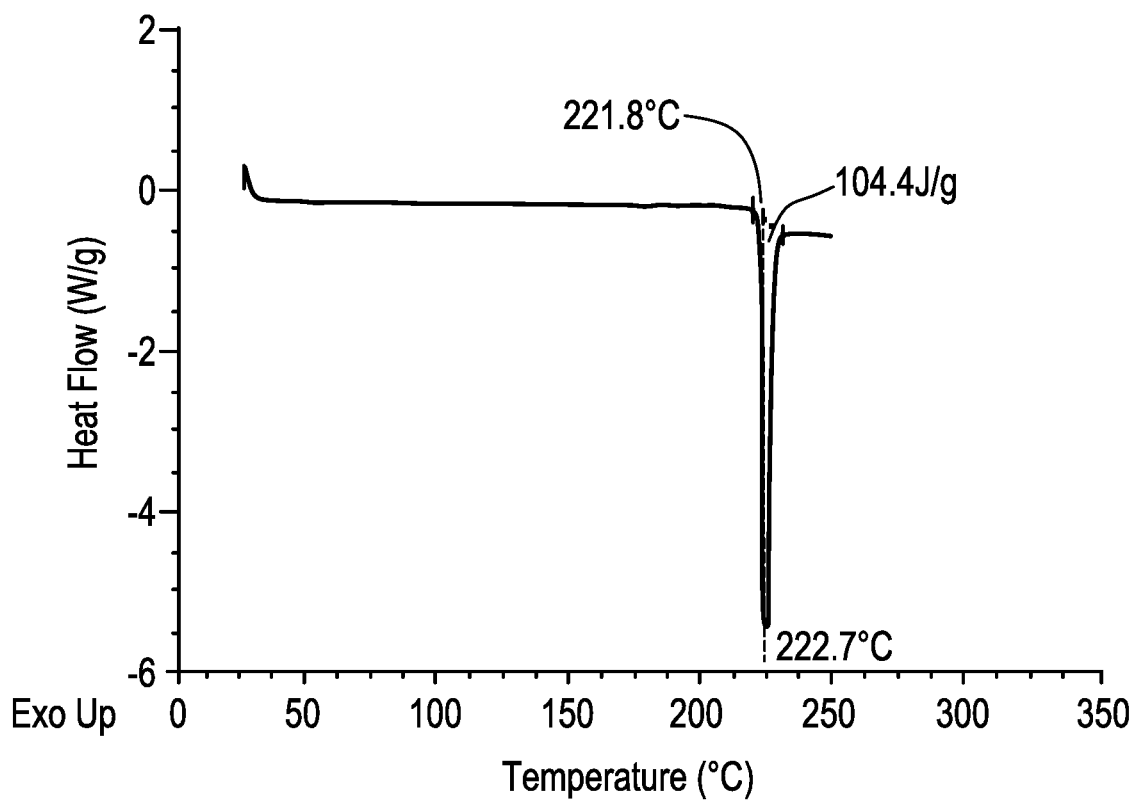

Embodiment 9 was obtained by heating embodiment 2 to a temperature of about 200° C. followed by cooling to 25° C. and also by cyclic DSC 25-200-25-300° C. Embodiment 9 was also obtained by additional procedures. One of such procedures was a two-step procedure: Embodiment 1s (1.5 g) was treated with 1,4-dioxane (10 vol) at RT. Seeds of embodiment 2 (5 mg) were added and the sample was stirred at RT for 24 hours. The resulting suspension was filtered and the sample was air-dried for 1.5 hours. This sample was determined to be embodiment 2 by XRPD. In the second step of this two-step procedure, embodiment 2 was heated to 210° C. at 10° C./min and held at 210° C. for 30 min. The sample was then allowed to cool to RT. The resulting solid was determined to be embodiment 9 by XRPD analysis. Another of such procedures was also a two-step procedure for obtaining embodiment 9. In this procedure, embodiment 1s (1.5 g) was treated with 1,4-dioaxne (10 vol). Seeds of embodiment 2 (5 mg) were added and the sample was stirred at RT for 24 hours. The resulting suspension was filtered and the sample was air-dried for 1.5 hours. This sample was determined to be embodiment 2 by XRPD. In the second step of this procedure, embodiment 2 was heated to 150° C. at 10° C./min followed by further heating to 170° C. at 2° C./min. The sample was then allowed to cool to RT. The resulting solid was determined to be embodiment 9 by XRPD analysis. The TGA and DSC of embodiment 9 is shown in FIGS. 22A and 22B, respectively.

Embodiment 1s was obtained by slurring embodiment 9 in the following solvents for 6 days at 50° C.: 2-butanone, acetone/water (90/10, v/v) and acetonitrile/water (90/10, v/v). Embodiment 1s was also obtained when the same experiment was performed at room temperature.

Figure 20A:
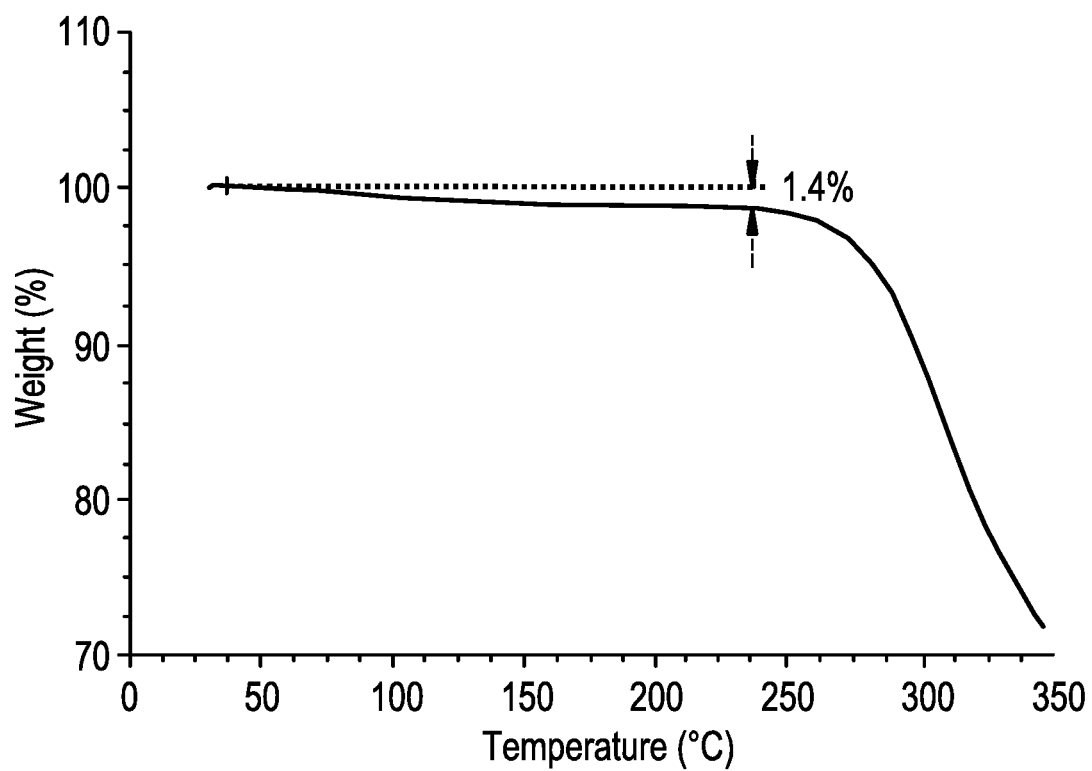
Figure 20B:
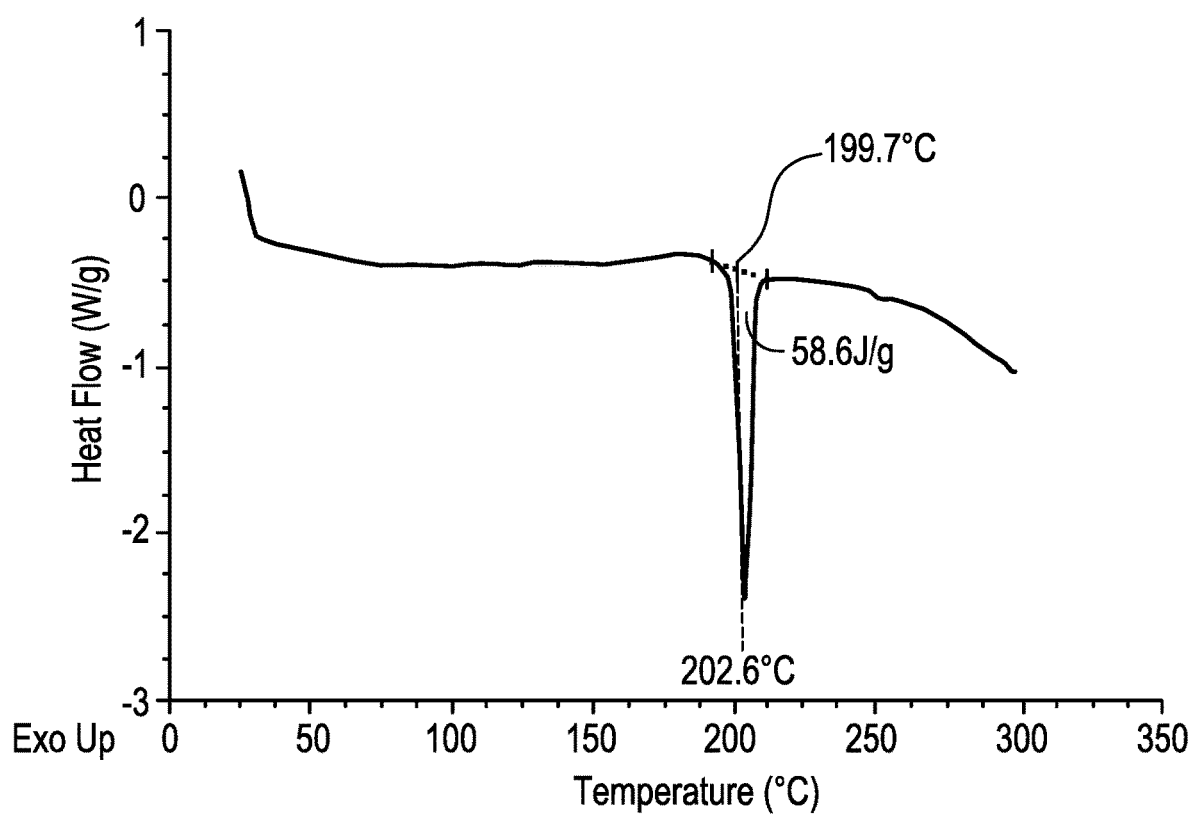

Embodiment 8 was obtained by heating embodiment 5 to a temperature of about 175° C. Embodiment 8 was also obtained by additional procedures. One of such procedures was a two-step procedure: Embodiment 1s (1.5 g) was treated with 1,4-dioxane 10 (vol) and stirred at RT for 72 hours. The resulting suspension was filtered and the solid that was obtained was dried in a vacuum oven at RT for 16 hours. The solid obtained from this first step was determined by XRPD to be embodiment 3c. In the second step, embodiment 3c (100 mg) was heated to 150° C. at 10° C./min, then heated at the slower rate of 2° C./min up to 180° C. The sample was then allowed to cool back to RT. The resulting solid was determined by XRPD to be embodiment 8. Another of such procedures was also a two step procedure for obtaining embodiment 8. In this procedure, embodiment 19 (300 mg) was treated with 1,4-dioxane (3 vol) and shaken at 60° C. for 24 hours. The resulting suspension was filtered and the solid obtained from this first step was determined by XRPD to be embodiment 3c. In the second step, embodiment 3c (300 mg) was heated to 180° C. at 10° C./min. The sample was then allowed to cool back to RT. The resulting solid was determined by XRPD to be embodiment 8. The TGA and DSC for embodiment 8 is shown in FIGS. 20A and 20B, respectively.

Figure 19A:
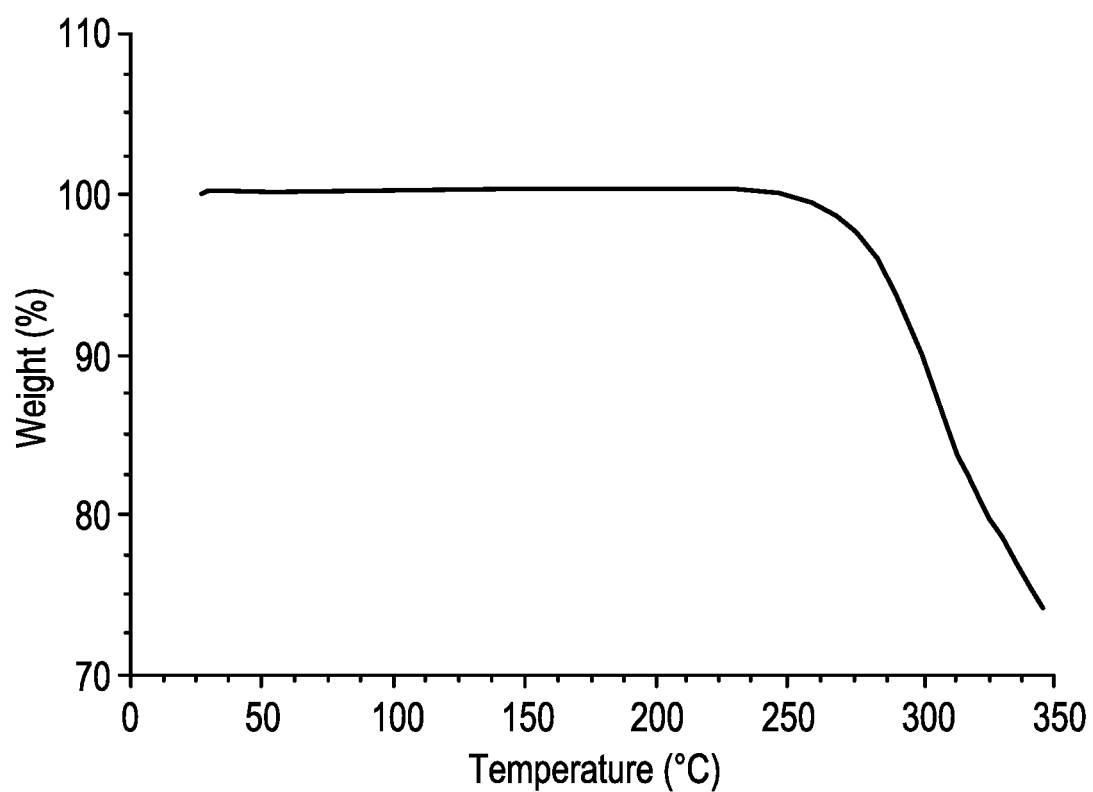
Figure 19B:
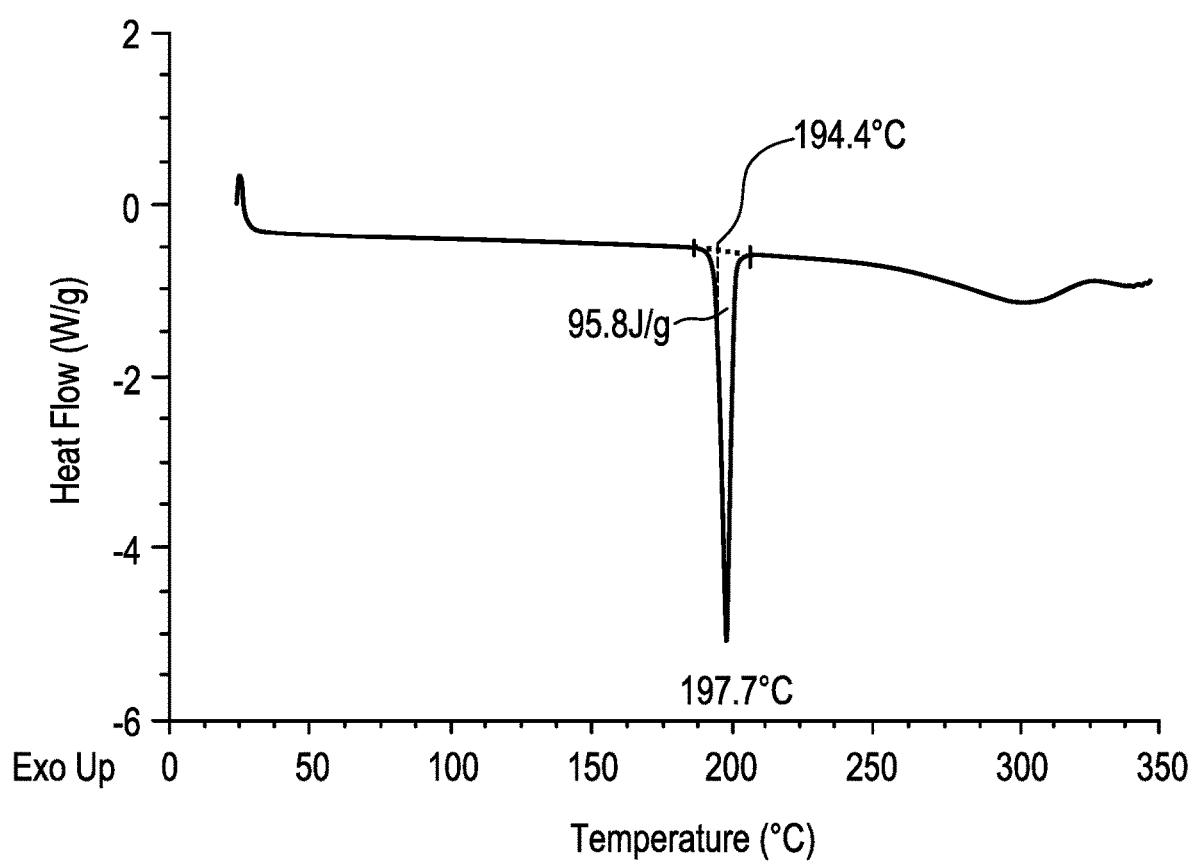

In addition to the preparation of embodiment 6 as described above, this embodiment was obtained by heating embodiment 11 (80-100 mg), whose preparation is described below, by thermal gravimetric analysis from ambient to 185° C. at 10° C./min and was held isothermally for 3 minutes. The sample was then allowed to cool to RT. Embodiment 6 was also obtained from embodiment 11 by subjecting it to a slurry experiment. The slurry experiment was run as follows: the solvent was added to embodiment 11 (50 mg) and the mixture was stirred at the designated temperature for 0.5 hours. Seed crystals of form 9 (5 mg) were added and the mixture was stirred overnight at the designated temperature. The solids were isolated by centrifugation and analyzed by XRPD. using isopropyl acetate (0.5 mL) at both 30° C. and 50° C. The generation of embodiment 6 was confirmed by XRPD. The TGA and DSC for embodiment 6 is shown in FIGS. 19A and 19B, respectively.

Additional embodiments of the invention were obtained as described below.

Embodiment 5 was converted to embodiment 9 by subjecting it to slurry experiments Slurry experiments were conducted as follows using various solvents at the temperatures identified: The solvent was added to embodiment 5 (50 mg) and the mixture was stirred at the designated temperature for 0.5 hours. Seed crystals of form 9 (5 mg) were added and the mixture was stirred overnight at the designated temperature. The solids were isolated by centrifugation and analyzed by XRPD. Slurry experiments run at 50° C. were conducted using the following solvents: TBME (0.75 mL) and a 33:67 mixture of isopropyl acetate:heptane (0.5 mL). Slurry experiments run at 75° C. were conducted using the following solvents: isopropyl acetate (0.5 mL) and methyl ethyl ketone (0.5 mL).

Figure 17A:
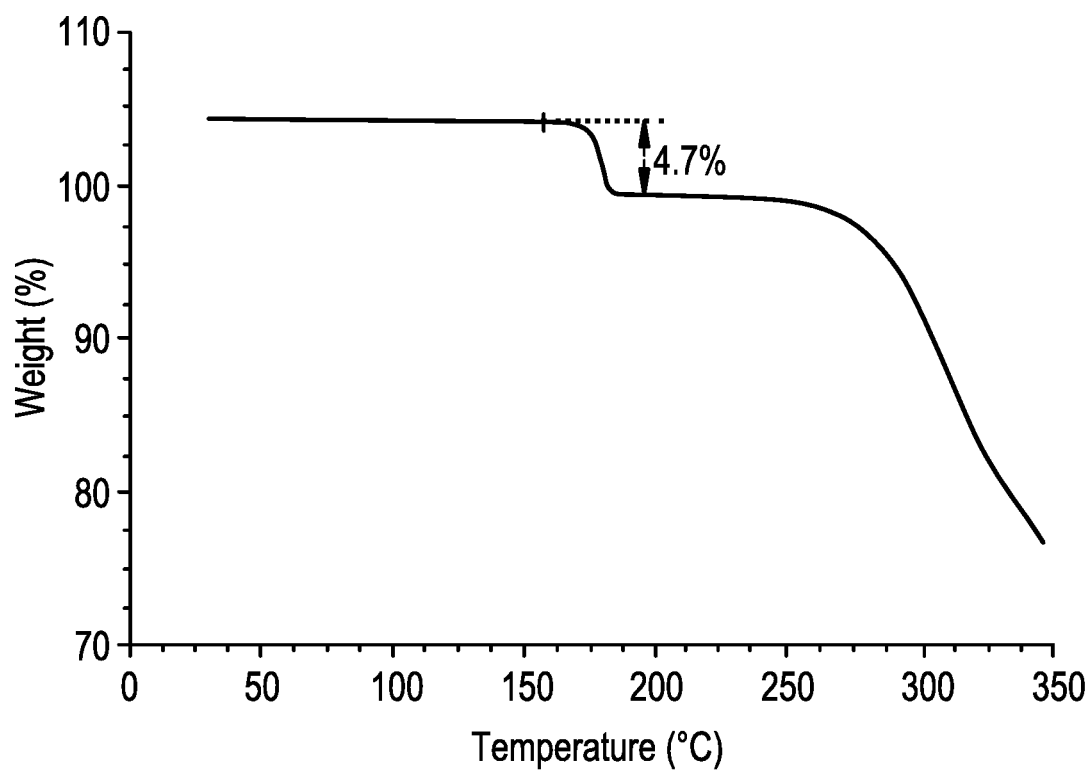
Figure 17B:
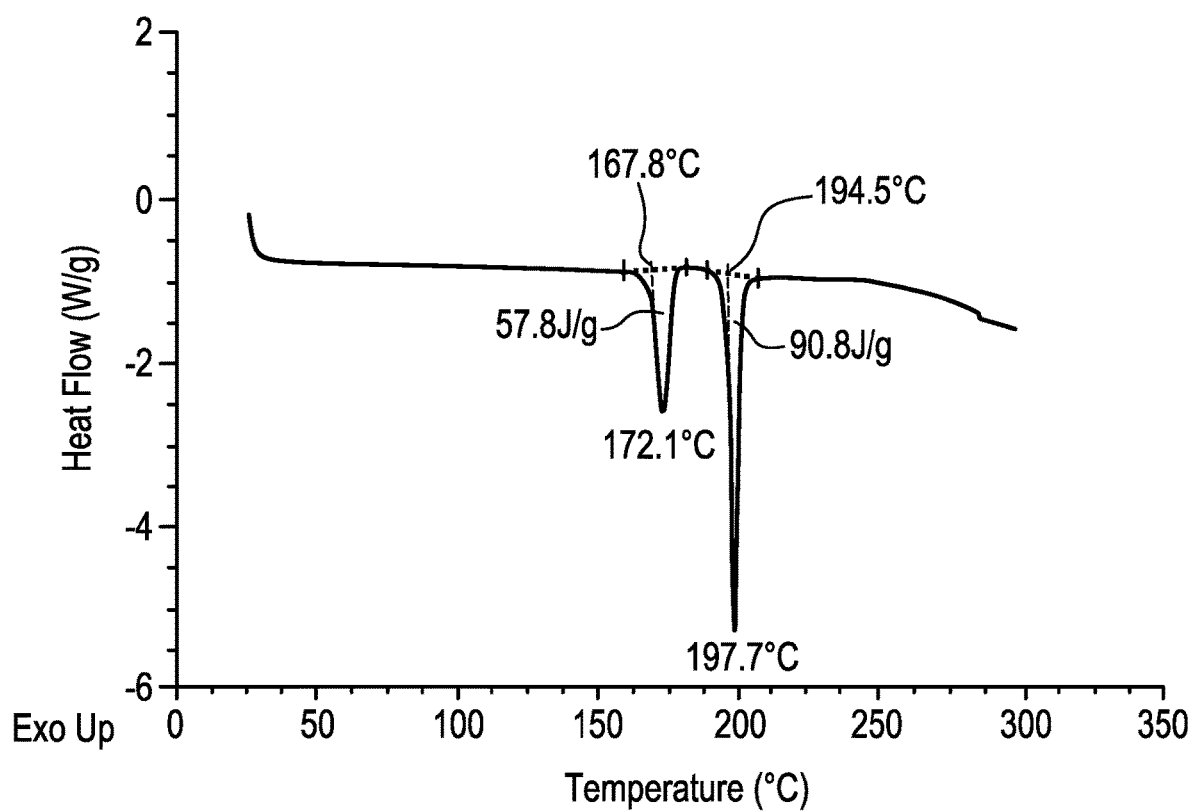

Embodiment 11 was obtained as follows: A suspension of embodiment 1s (45g) in ethanol (absolute, water content <0.1%, 300 mL) at 50° C. was stirred for 16.5 hours. The suspension was then cooled to 5° C. at 0.25° C./minute. Subsequently, the suspension was stirred at 5° C. for 3 hours. The solids were then filtered off and washed with cold (5° C.) ethanol (absolute, water content <0.1%, 90 mL), and dried under vacuum at 40° C. for 17 hours to yield approximately 39 g of embodiment 11. The TGA and DSC of embodiment 11 is shown in FIGS. 17A and 17B, respectively.

Embodiment 11 was also obtained as follows: Absolute ethanol (170 mL) was added to embodiment 1s (19 g) and heated to about the boiling point of the solvent. A small amount of the solids (5%) did not dissolve and were removed by hot filtration. It was determined that the solids that were filtered off, were embodiment 1s. So the solids were added back into the filtrate and this mixture was heated until all the solids dissolved. To this hot solution was added, heptane (535 mL), drop-wise via a separatory funnel. During this drop-wise addition of heptane, the hot solution was stirred vigorously. After the addition of heptane was complete, the flask containing the hot solution/heptane mixture was submerged in an ice water bath and vigorously stirred for one hour. The solids were then collected by filtration and the white solid filter cake was dried by pulling air through it for 15 minutes. It was further dried by heating it at 70° C. for 16 hours under high vacuum and then by heating it at 80° C. for 18 hours to yield 16.3 g of embodiment 11. The diffractogram for embodiment 11 is shown in FIG. 7.

Figure 18:
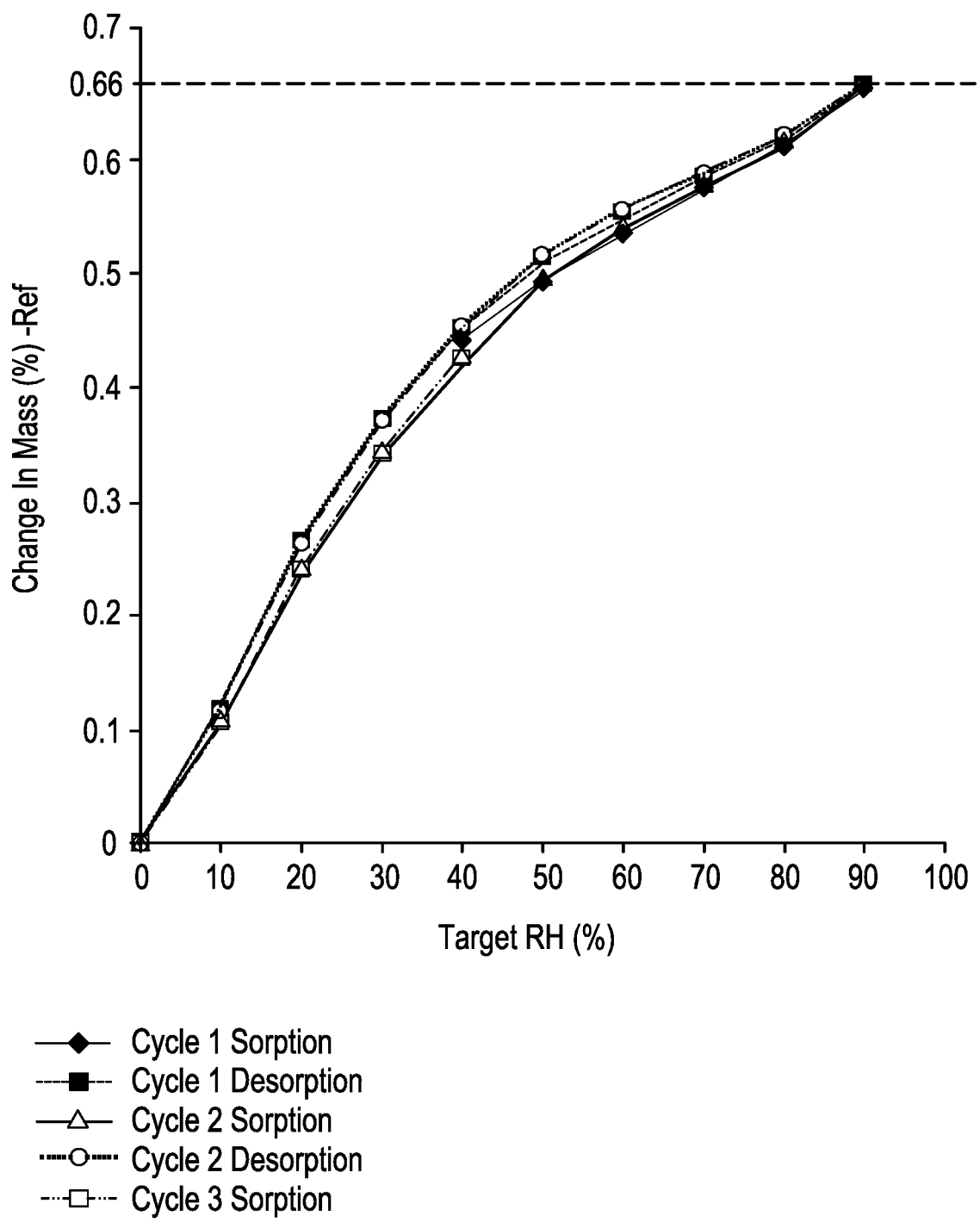
Figure 24:
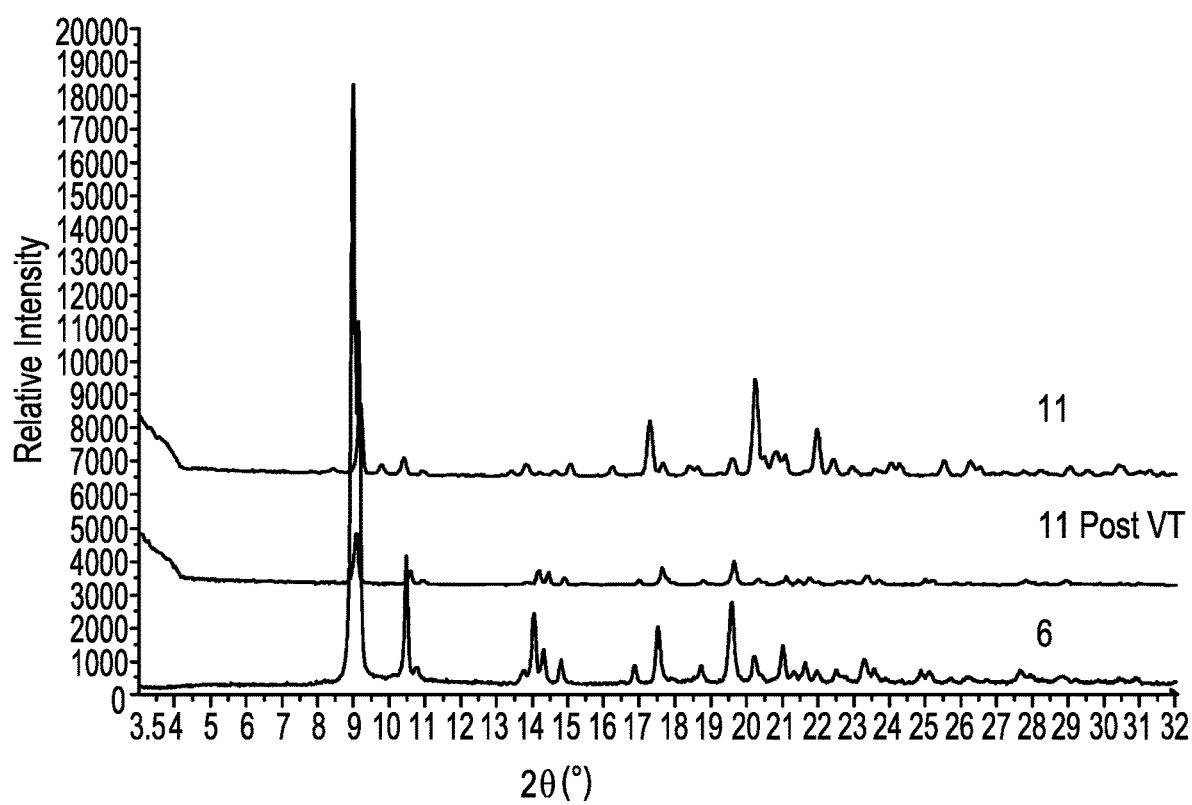

In a hygroscopicity study of embodiment 11, it was found it to be only slightly hygroscopic, with a mass change of 0.66% between 0-90% RH in the GVS analysis as shown in FIG. 18. XRPD analysis post GVS analysis showed that the material was physically stable. Variable temperature (VT)-XRPD was performed in order to assess the stability of embodiment 11 upon heating. The material remained unchanged as shown by XRPD analysis when it was subjected to temperatures up to ca. 175° C., however above 180° C. the sample converted to embodiment 6. The diffractograms of embodiment 11 before and after the VT-XRPD experiment, along with the diffractogram for embodiment 6 are shown in FIG. 24. Embodiment 11 was also subjected to static storage analysis at 40° C./75% RH for up to 48 days. The samples were analyzed by XRPD and Karl Fisher (KF) after 2 days, 5 days and 48 days. Embodiment 11 remained unchanged as shown by XRPD analysis with a total water uptake of 1.2% after 48 days. $^1$H-NMR of the material post 48 days static storage showed the material retained 0.36 mol eq of ethanol. Embodiment 11 stored under ambient conditions for the period of the study was shown to contain 0.46 mol eq of ethanol by $^1$H-NMR.

Figure 7A:
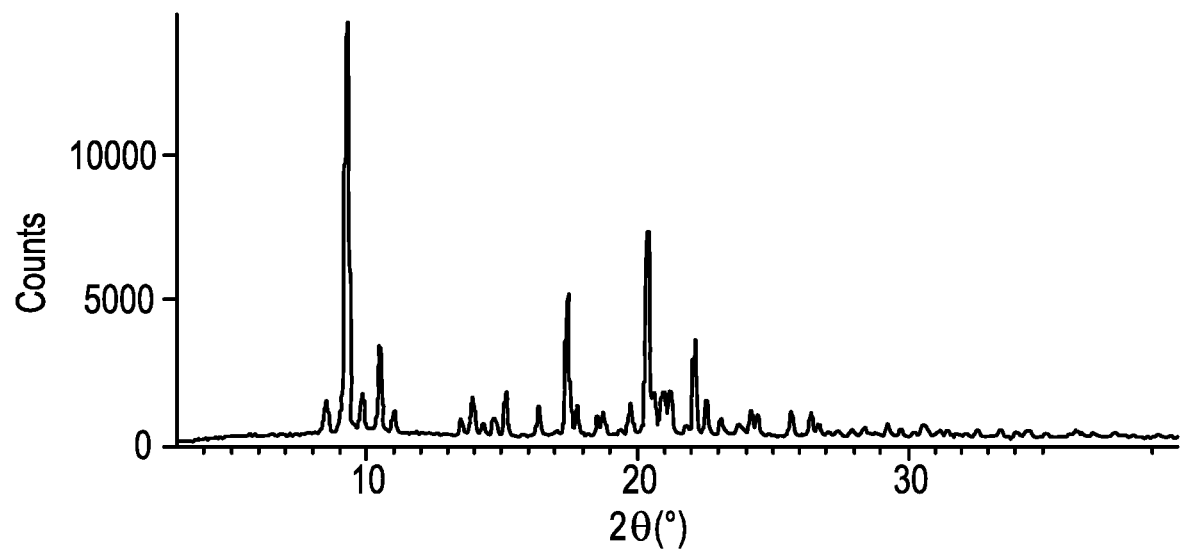
Figure 7B:
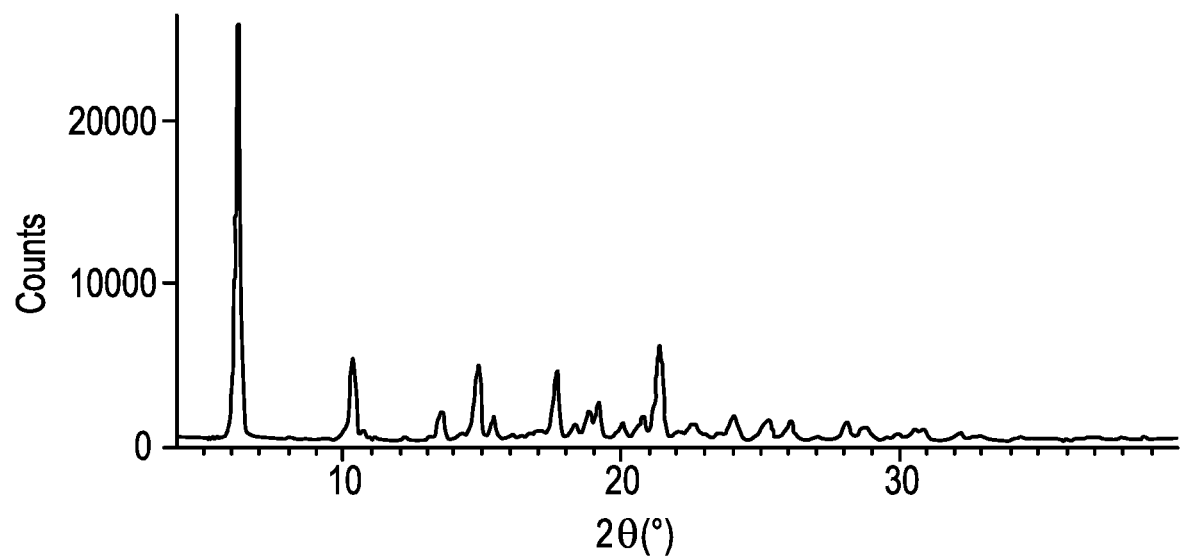
Figure 7C:
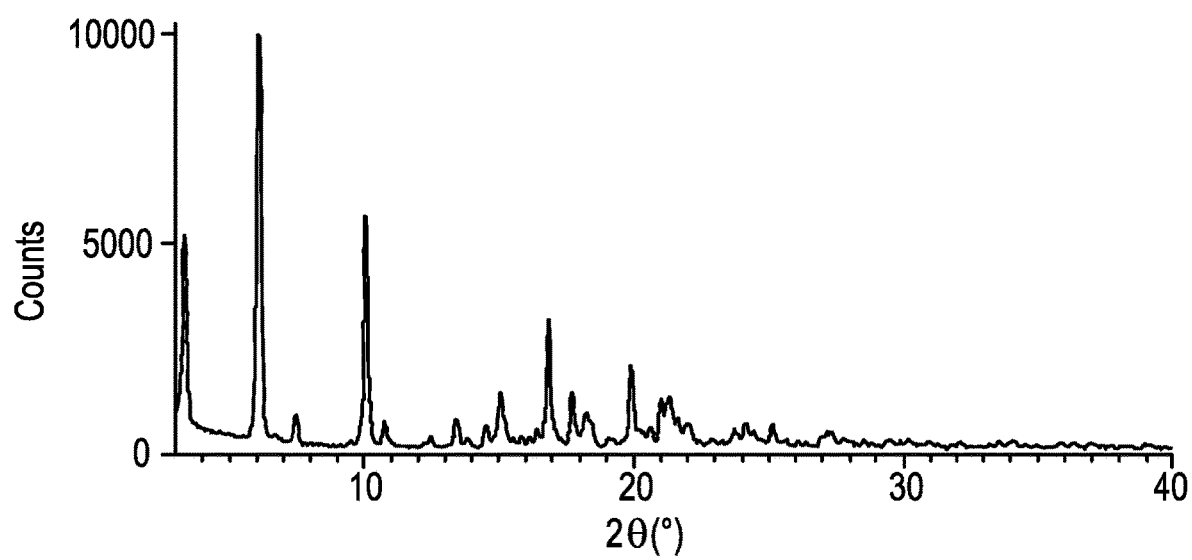
Figure 7D:
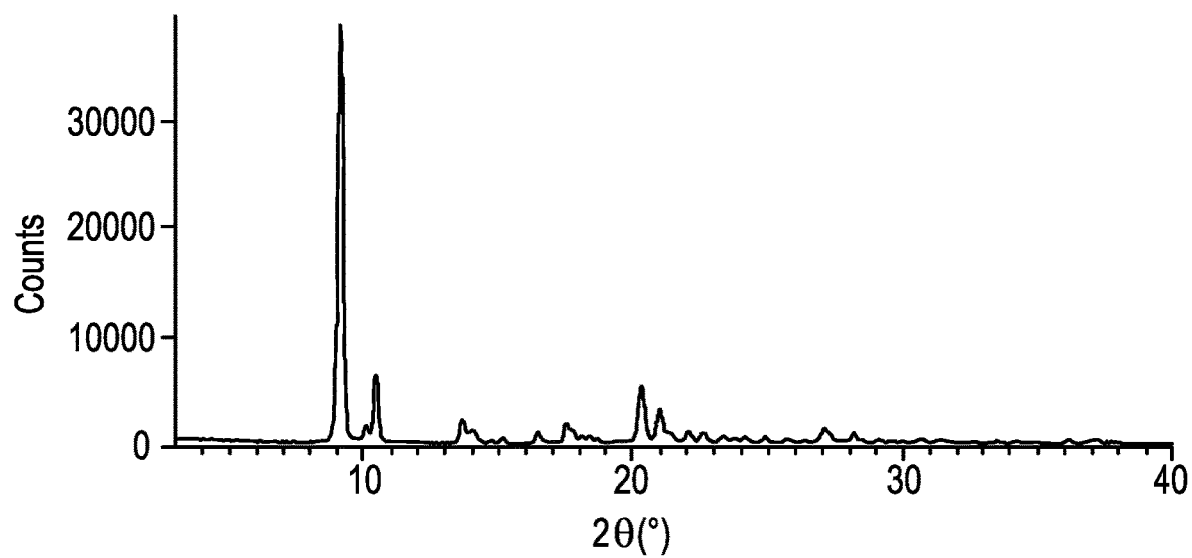
Figure 7E:
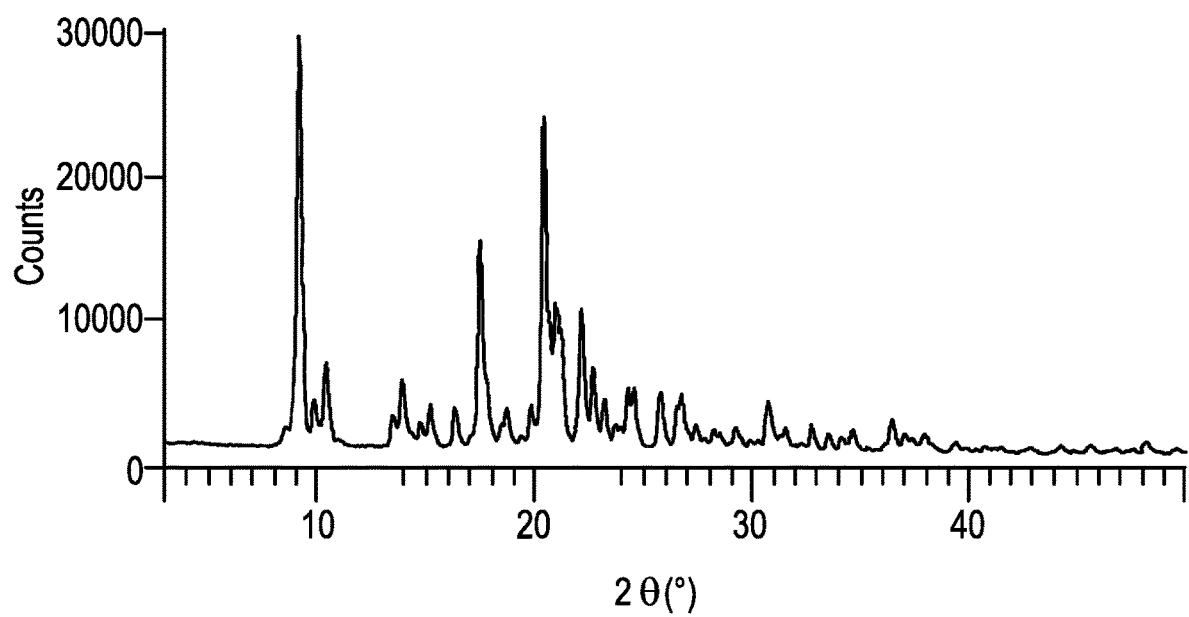

Embodiment 11b was obtained from embodiment 1s as follows: 10 mL of dried methanol was added to 3.3 g of embodiment 1s. This mixture was subjected to the following temperature cycling: The mixture was heated at 40° C. for 1 hour and then the temperature was increased to 60° C. over a 2 hour period. The mixture was then heated at 60° C. for 1 hour. The temperature was then decreased to 40° C. over a 2 hour period. This temperature cycling regime was repeated for a total of about 20 hours. At that time the mixture was cooled to 5° C. over a 2 hour period. The solids were isolated at 5° C. by vacuum filtration and then dried at ambient temperature under vacuum for about 66 hours. Alternatively, embodiment 11b was obtained from embodiment 1s using the following procedure: 1 mL of dried methanol was added to 330 mg of embodiment 1s. This mixture was subjected to the following temperature cycling: The mixture was heated at 40° C. for 1 hour and then the temperature was increased to 60° C. over a 2 hour period. The mixture was then heated at 60° C. for 1 hour. The temperature was then decreased to 40° C. over a 2 hour period. This temperature cycling regime was repeated for a total of about 18 hours. At that time the solids were isolated by centrifugation and then dried at ambient temperature under vacuum for about 33 hours. The methanol for the above experiments was dried using molecular sieves (3 Å, activated at 100° C. under vacuum for at least 24 h). The diffractogram for embodiment 11b is shown in FIG. 7E.

Embodiment 12 was obtained from embodiment 1s, which was exposed to humidity conditions below 10% RH at 25° C. to provide embodiment 12. The diffractogram for embodiment 12 is shown in FIG. 7B.

Embodiment 13 was obtained as follows: To a 250 mL 4-necked flask at 25±5° C. was added a sample of embodiment 1s. The flask was then charged with MeOH (4.0 V, 40 mL) and purified water (10 mL, 1.0 V) and stirred until all the solid dissolved. $N_2$ was bubbled into the mixture for 1 hour and the mixture was then cooled to 0 to 5° C. A 0.225 mL volume of a cooled solution (0 to 5° C.) of $NaBH_4$/water (0.006 eq., 2.5% w/w) was prepared with purified water (40 mL) charged into a 100 mL of a 4-necked flask under $N_2$ at 0° C., followed by the addition of $NaBH_4$ (1.0 g); the mixture was stirred at 0° C. until all the $NaBH_4$ dissolved. Such $NaBH_4$ solution was added into the 250-mL flask that was cooled (0 to 5° C.) and stirred at 0 to 5° C. The color of the reaction mixture changed to yellow. Purified water (40 mL, 4.0 V, degassed with $N_2$ before using) was added dropwise over 1 hour at 0 to 5° C. The reaction was stirred for 4 hours under $N_2$ at 0 to 5° C. Additional purified water (30 mL, 3.0 V, degassed) was added dropwise over 1 hour at 0 to 5° C. and the reaction mixture was stirred for an additional 16 hours under $N_2$ at 0 to 5° C. The reaction was then filtered and the resulting solids were washed with purified water (20 mL, 2 V, degassed with $N_2$ before using) in a glove box environment under $N_2$ ($O_2$ content being 200 ppm). The solids were dried under vacuum with moisturized nitrogen at 35±5° C. to provide embodiment 13 as an off-white solid. The diffractogram for embodiment 13 is shown in FIG. 7C.

Embodiment 14 was prepared as follows: 2-(1-((1r,4r)-4-(cyanomethyl)cyclohexyl)-6-(phenylsulfonyl)-1,6-dihydro-imidazo[4,5-d]pyrrolo[2,3-b]pyridin-2-yl)-N-(2-hydroxy-2-methylpropyl)acetamide (48.15 kg, prepared in Ex. 2, Step B), EtOH (technical grade, 481 L) and KOH (6.613 kg) were stirred at 10-20° C. for 9 hours. The reaction was then quenched with acetic acid (6.74 L) maintaining the temperature at 10-20° C. Acetonitrile (240 L) was added and the solvents were evaporated under reduced pressure to a volume of about 240 L. This addition and evaporation of acetonitrile was repeated two more times. The resulting mixture was heated to 60-70° C. for 5 hours after which it was cooled to 10-15° C. and stirred for 2 h. The solids in this mixture were then filtered off and washed with acetonitrile (48 L) twice. The solids were then added to water (240 L) and the reaction mixture heated to 45-50° C. for 3-5 hours followed by cooling to 15-20° C. for 4 hours. The solids remaining were filtered off and the filter cake was washed with water (96 L, two times). This filter cake was dried at 45° C. to provide embodiment 14 (26.28 kg). The diffractogram for embodiment 14 is shown in FIG. 7D.

Additional embodiments of the invention were obtained as described below.

Solubility Assessment

Figure 8:
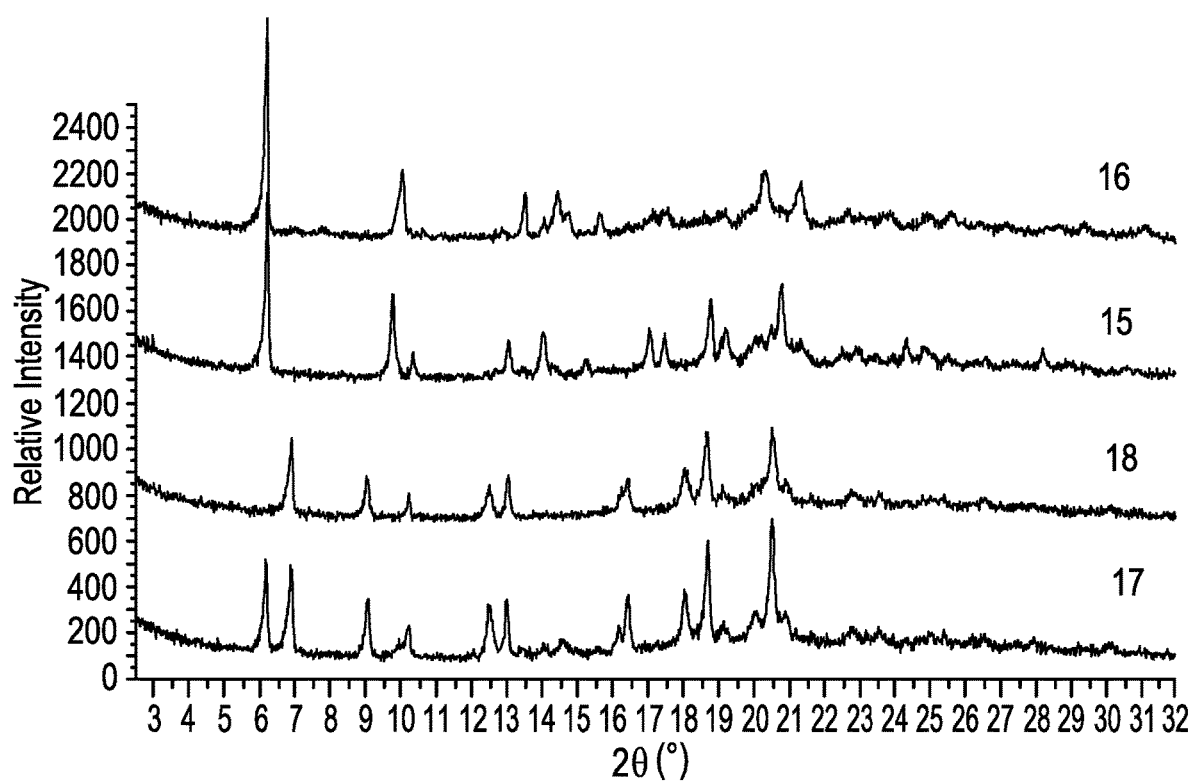
Figure 9:
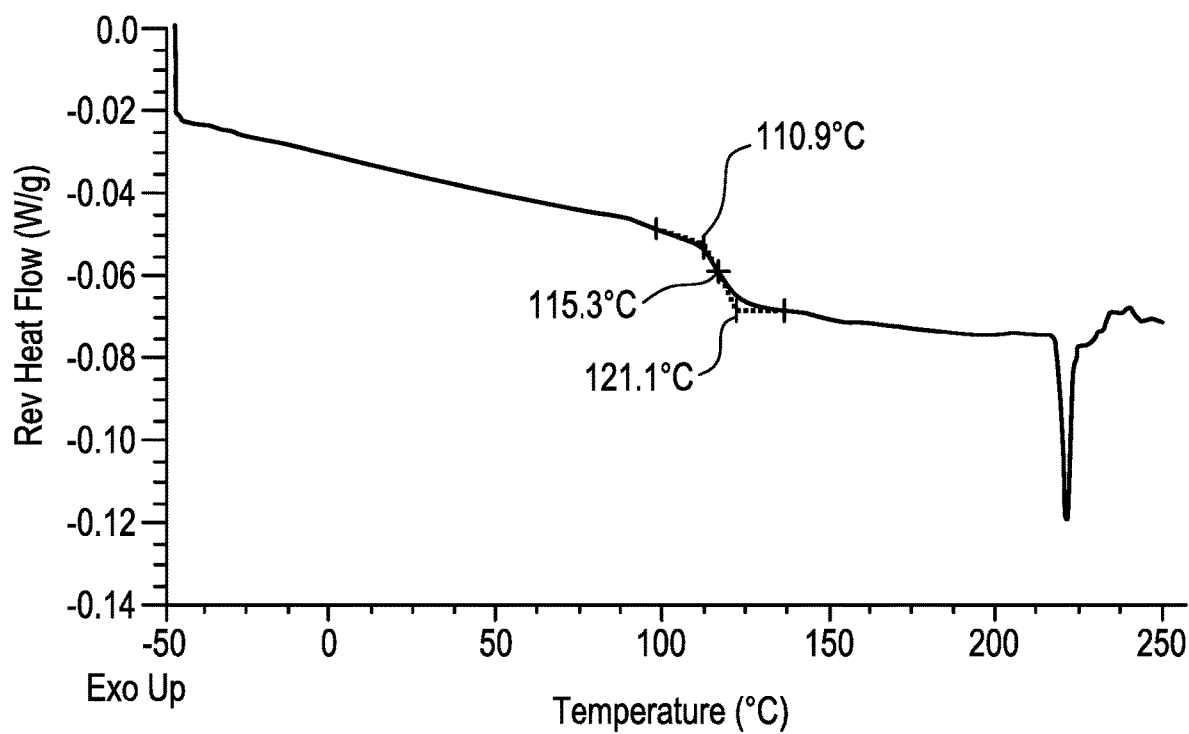
Figure 10A:
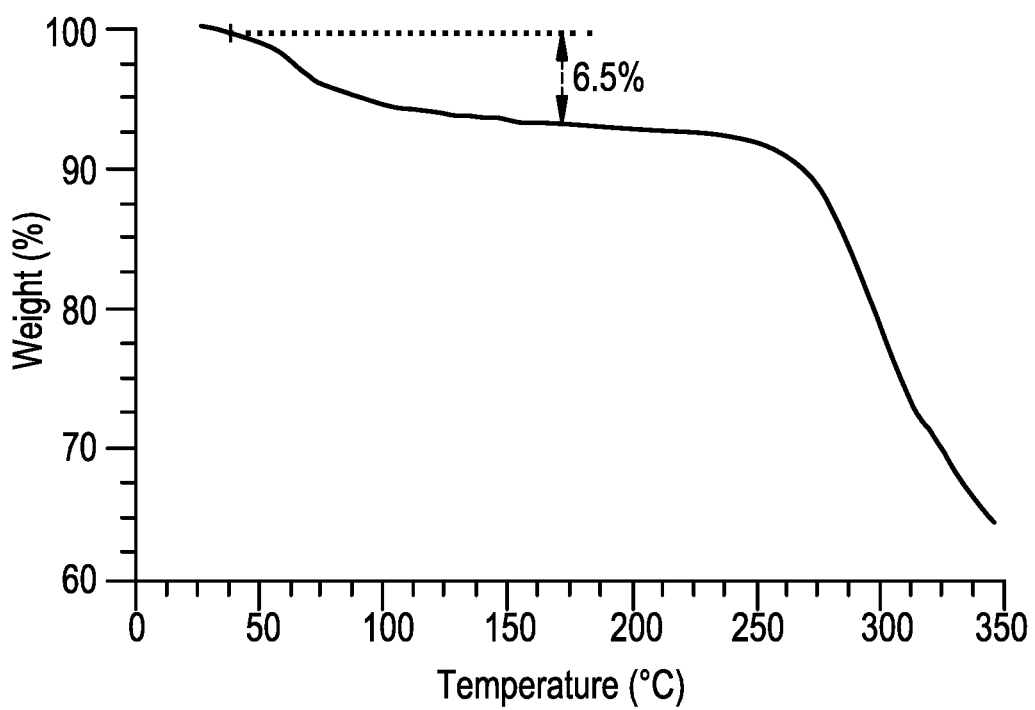
Figure 10B:
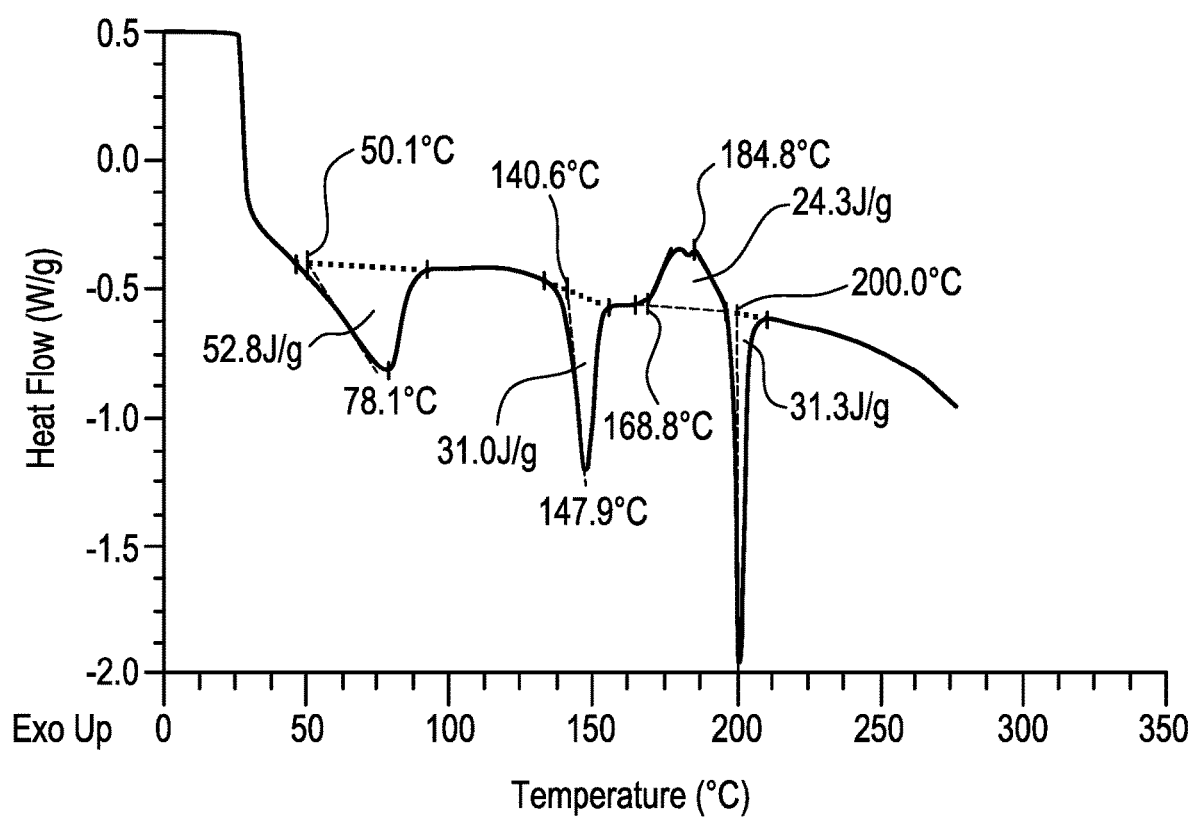
Figure 11:
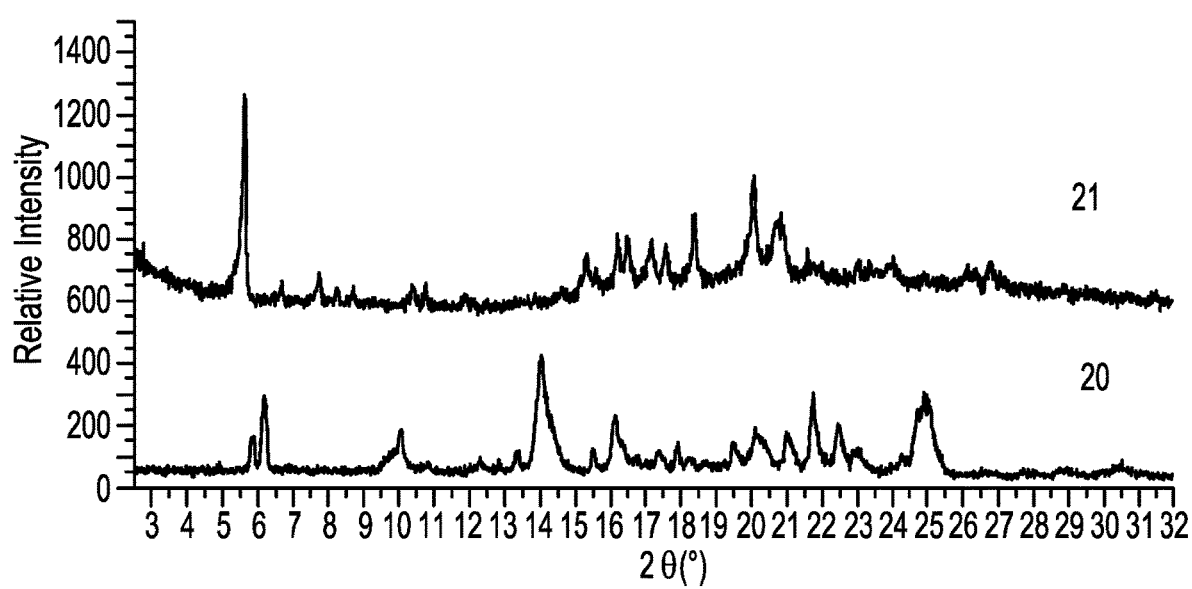
Figure 12A:
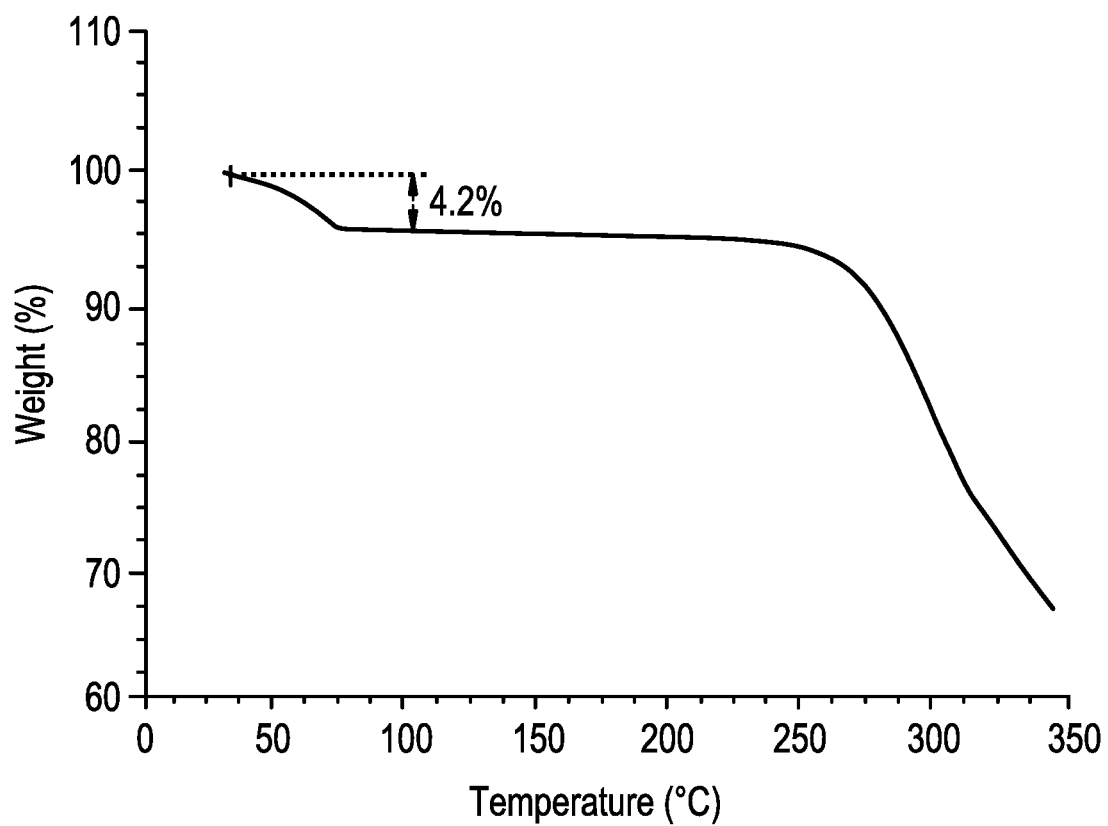
Figure 12B:
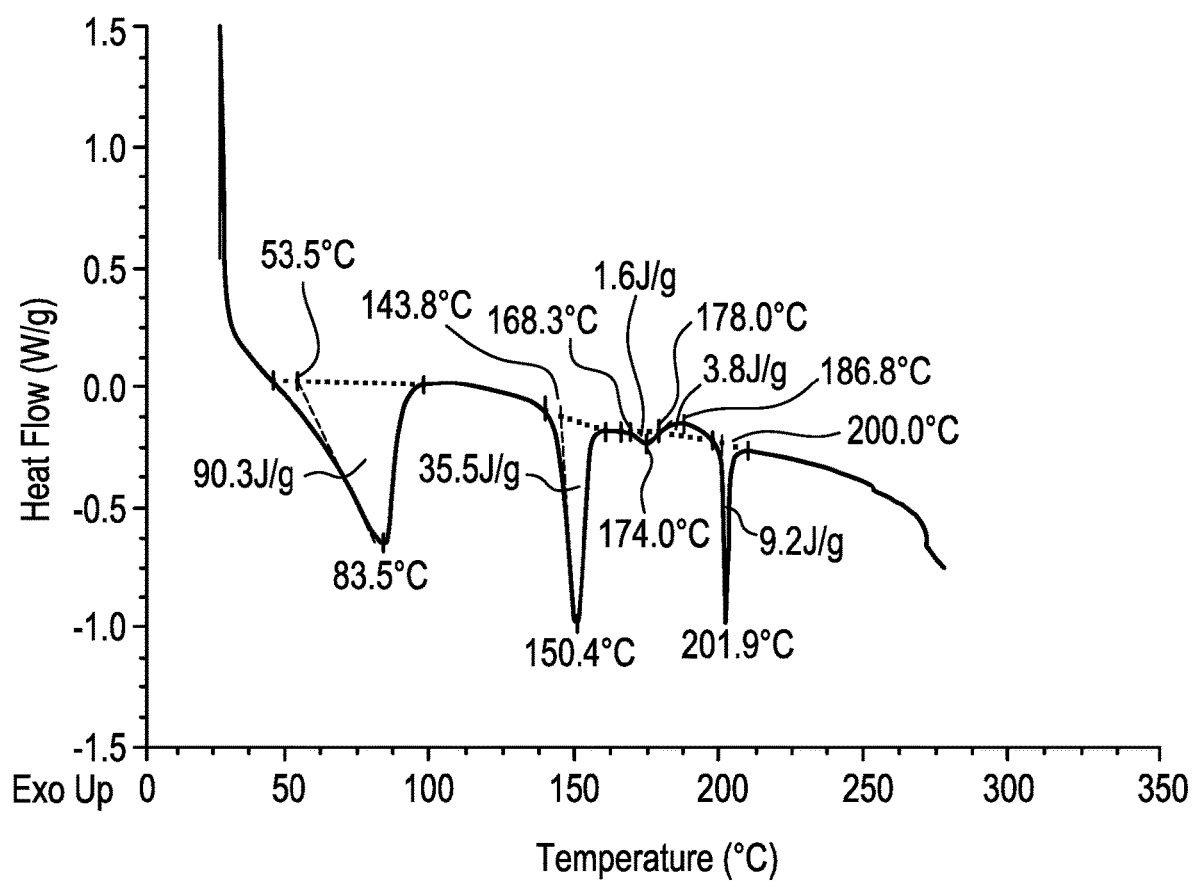

Embodiment 1s (15 mg) was treated with increasing volume of solvent until the material fully dissolved or until a maximum of 100 mL of solvent had been added. The solvent was added in the following increments: 5 mL, 10 mL, 20 mL, 30 mL, 40 mL, 50 mL, 70 mL and 100 mL. After each addition of solvent, the system was held at 50° C. for 5 min with gentle stirring and visually assessed for presence of solid. This process continued until a total of 100 mL of solvent had been added. If no solid remained, then no additional solvent was added. After the assessment was completed, the solution was held at 50° C. for 1 h and then cooled from 50° C. to 5° C. at 0.1° C./min with stirring. If solid was present, then the mixture was filtered under vacuum using a 96 well plate and analyzed by XRPD. If a clear solution was obtained, the solution was left to evaporate at RT. The following solvents, where total amount added is noted in parenthesis immediately after the solvent, at temperatures of 5° C. and 50° C. were used according to this procedure, where the dissolution extent is given within parenthesis after each temperature which yielded the noted embodiment: Water (100 mL) at 5° C. (suspension) and 50° C. (suspension), yielded embodiment 1s whose diffractogram is shown in FIG. 5; methanol (10 mL) at 5° C. (suspension) and at 50° C. (solution), yielded embodiment 1s whose diffractogram is shown in FIG. 5; ethanol (30 mL) at 5° C. (suspension) and at 50° C. (solution), yielded embodiment 1s whose diffractogram is shown in FIG. 5; 2-propanol (30 mL) at 5° C. (suspension) and at 50° C. (solution), yielded embodiment 1s whose diffractogram is shown in FIG. 5; 1-propanol (30 mL) at 5° C. (suspension) and at 50° C. (solution), yielded embodiment 1s whose diffractogram is shown in FIG. 5; acetone (100 mL) at 5° C. (suspension) and at 50° C. (solution), yielded embodiment 1s whose diffractogram is shown in FIG. 5; ethyl acetate (100 mL) at 5° C. (suspension) and at 50° C. (turbid), yielded embodiment 1s whose diffractogram is shown in FIG. 5; acetonitrile (100 mL) at 5° C. (suspension) and at 50° C. (solution), yielded embodiment 6 whose diffractogram is shown in FIG. 3; toluene (100 mL) at 5° C. (partially dissolved) and at 50° C. (turbid), yielded embodiment 1s whose diffractogram is shown in FIG. 5; isopropyl acetate (100 mL) at 5° C. (suspension) and at 50° C. (turbid), yielded embodiment 1s whose diffractogram is shown in FIG. 5; methyl t-butyl ether (100 mL) at 5° C. (suspension) and at 50° C. (suspension), yielded embodiment 1s whose diffractogram is shown in FIG. 5; 2-butanone (100 mL) at 5° C. (suspension) and at 50° C. (solution), yielded embodiment 1s whose diffractogram is shown in FIG. 5; THF (70 mL) at 5° C. (partially dissolved) and at 50° C. (solution), yielded embodiment 1s whose diffractogram is shown in FIG. 5; DMSO (5 mL) at 5° C. (solution, sample was frozen and left to evaporate at RT) and at 50° C. (solution), yielded embodiment 1s whose diffractogram is shown in FIG. 5; N-methyl pyrrolidinone (5 mL) at 5° C. (solution, left to evaporate at RT) and at 50° C. (solution), yielded embodiment 1s whose diffractogram is shown in FIG. 5; diethyl ether (100 mL) at 5° C. (suspension) and at 50° C. (suspension), yielded embodiment 1s whose diffractogram is shown in FIG. 5; methyl isobutyl ketone (100 mL) at 5° C. (suspension) and at 50° C. (suspension), yielded embodiment 1s whose diffractogram is shown in FIG. 5; DCM (100 mL) at 5° C. (suspension) and at 50° C. (suspension), yielded embodiment 1s whose diffractogram is shown in FIG. 5; heptane (100 mL) at 5° C. (suspension) and at 50° C. (suspension), yielded embodiment 18 whose diffractogram is shown in FIG. 8; 1-4-dioxane (100 mL) at 5° C. (partially dissolved, sample was frozen and left to evaporate at RT) and at 50° C. (suspension), yielded in dried form embodiment 3c whose diffractogram is shown in FIG. 5; nitromethane (100 mL) at 5° C. (suspension) and at 50° C. (suspension), yielded a poorly crystalline embodiment (diffractogram not shown); 1-methoxy-2-propanol (20 mL) at 5° C. (solution) and at 50° C. (solution), yielded in dried form embodiment 20 whose diffractogram is shown in FIG. 11; 2-methyl-THF (100 mL) at 5° C. (suspension) and at 50° C. (suspension), yielded embodiment 18 whose diffractogram is shown in FIG. 8 and whose TGA and DSC is shown in FIGS. 10A and 10B, respectively; tetralin (100 mL) at 5° C. (suspension) and at 50° C. (turbid), yielded a mixture of embodiment 4 and embodiment 1b whose diffractogram is shown in FIG. 3; 3-methyl-1-butanol (100 mL) at 5° C. (suspension) and at 50° C. (solution), yielded embodiment 17 whose diffractogram is shown in FIG. 8 and whose TGA and DSC is shown in FIGS. 12A and 12B, respectively; anisole (100 mL) at 5° C. (suspension) and at 50° C. (turbid), yielded a mixture of embodiment 4 and embodiment 1b whose diffractogram is shown in FIG. 3; t-butanol/water (1:1, 10 mL) at 5° C. (solution) and at 50° C. (solution), yielded in dried form an embodiment 19 whose modulated DSC is shown in FIG. 9; 1,2-dimethoxyethane (100 mL) at 5° C. (suspension) and at 50° C. (turbid), yielded a mixture of embodiment 4 and embodiment 1b whose diffractogram is shown in FIG. 3; cumene (100 mL) at 5° C. (suspension) and at 50° C. (turbid), yielded a mixture of embodiment 4 and embodiment 1b whose diffractogram is shown in FIG. 3; diisopropyl ether (100 mL) at 5° C. (suspension) and at 50° C. (suspension), yielded embodiment 18 whose diffractogram is shown in FIG. 8; morpholine (5 mL) at 5° C. (suspension) and at 50° C. (solution), yielded in dried form embodiment 21 whose diffractogram is shown in FIG. 11; ethanol:water (95:5, 10 mL) at 5° C. (suspension) and at 50° C. (solution), yielded a poorly crystalline embodiment (diffractogram not shown); ethanol:water (9:1, 5 mL) at 5° C. (solution) and at 50° C. (solution), yielded in dried form embodiment 1s whose diffractogram is shown in FIG. 5; and acetonitrile:water (95:5, 30 mL) at 5° C. (suspension) and at 50° C. (solution), yielded a poorly crystalline embodiment (diffractogram not shown).

Incubation at 5° C.

Several experiments of incubation at 5° C. were performed by treating embodiment 1s (30 mg) with each solvent, and the mixture was slurried at 5° C. for 48 h. An aliquot was taken and immediately analyzed by XRPD. Each aliquot dried for 16 h and was re-analyzed by XRPD. The air-dried samples were then placed in a vacuum oven (RT) for 24 h before further analysis by XRPD. The following solvents, where total solvent amount added is noted in parenthesis immediately after the solvent followed by dissolution extent, were used according to this procedure which yielded the noted embodiment: Water (30 mL, suspension), yielded embodiment 1s whose diffractogram is shown in FIG. 5; methanol (5 mL, suspension), yielded embodiment 1s whose diffractogram is shown in FIG. 5; ethanol (30 mL, suspension), yielded embodiment 1s whose diffractogram is shown in FIG. 5; 2-propanol (30 mL, suspension), yielded embodiment 1s whose diffractogram is shown in FIG. 5; 1-propanol (30 mL, suspension), yielded embodiment 1s whose diffractogram is shown in FIG. 5; acetone (30 mL, suspension), yielded embodiment 1s whose diffractogram is shown in FIG. 5; ethyl acetate (30 mL, suspension), yielded embodiment 1s whose diffractogram is shown in FIG. 5; acetonitrile (30 mL, suspension), yielded a poorly crystalline embodiment (diffractogram not shown); toluene (30 mL, suspension), yielded embodiment 15 whose diffractogram is shown in FIG. 8; isopropyl acetate (30 mL, suspension), yielded embodiment 17 whose diffractogram is shown in FIG. 8; methyl t-butyl ether (30 mL, suspension), yielded embodiment 18 whose diffractogram is shown in FIG. 8; 2-butanone (30 mL, suspension), yielded embodiment 1s whose diffractogram is shown in FIG. 5; THF (30 mL, suspension), yielded embodiment 17 whose diffractogram is shown in FIG. 8; diethyl ether (30 mL, suspension), yielded embodiment 1s whose diffractogram is shown in FIG. 5; methyl isobutyl ketone (30 mL, suspension), yielded embodiment 17 whose diffractogram is shown in FIG. 8; DCM (30 mL, suspension), yielded embodiment 1s whose diffractogram is shown in FIG. 5; heptane (30 mL, suspension), yielded embodiment 1s whose diffractogram is shown in FIG. 5; 1,4-dioxane (30 mL, suspension), yielded embodiment 3c whose diffractogram from this experiment is shown in FIG. 5; nitromethane (30 mL, suspension), yielded a poorly crystalline form embodiment 1s whose diffractogram is not shown; propylene glycol (30 mL, suspension), yielded a poorly crystalline embodiment (diffractogram not shown); 2-methyl-tetrahydrofuran (30 mL, suspension), yielded embodiment 18 whose diffractogram is shown in FIG. 8; tetralin (30 mL, suspension), yielded a poorly crystalline embodiment 1s whose diffractogram is not shown; 3-methyl-1-butanol (30 mL, suspension), yielded embodiment 18 whose diffractogram is shown in FIG. 8; anisole (30 mL, suspension), yielded embodiment 1s with an whose diffractogram is similar to that of embodiment 1s (as shown in FIG. 5) except that it displays some additional peaks; 1,2-dimethoxyethane (30 mL, suspension), yielded embodiment 1s with an whose diffractogram is similar to that of embodiment 1s (as shown in FIG. 5) except that it displays some additional peaks; cumene (30 mL, suspension), yielded embodiment 1s with an whose diffractogram is similar to that of embodiment 1s (as shown in FIG. 5) except that it displays some additional peaks; diisopropyl ether (30 mL, suspension), yielded embodiment 17 whose diffractogram is shown in FIG. 8; ethanol:water (95:5, 30 mL, suspension), yielded embodiment 1s whose diffractogram is shown in FIG. 5; acetonitrile:water (95:5, 30 mL, suspension), yielded a poorly crystalline embodiment (diffractogram not shown); and polyethylene glycol (30 mL, suspension), yielded a poorly crystalline embodiment (diffractogram not shown).

Heat/Cool Maturation

Figure 13:
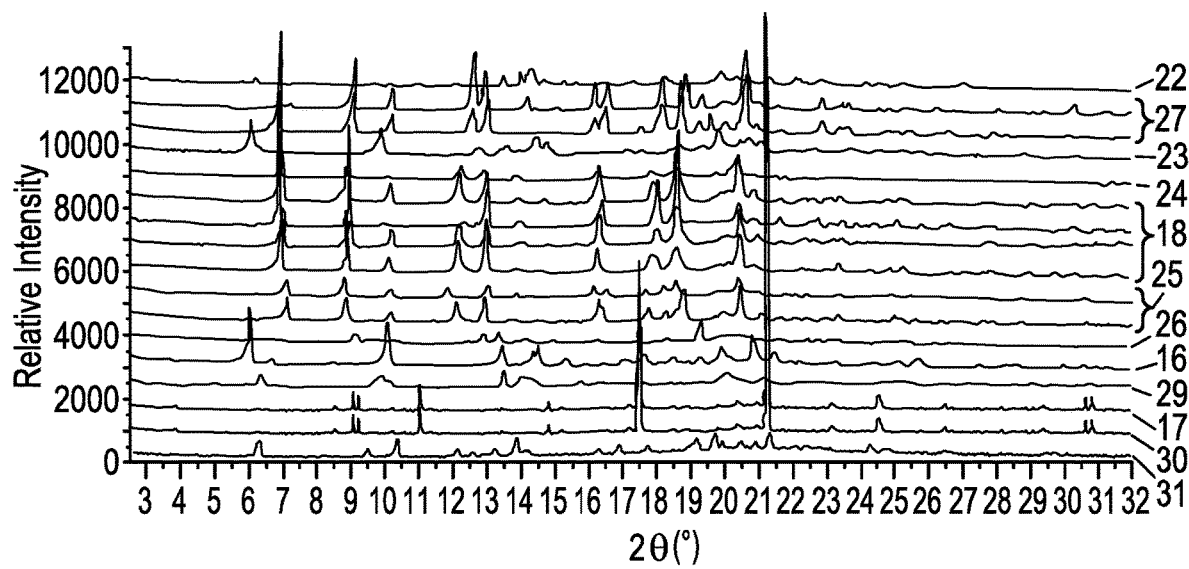
Figure 23A:
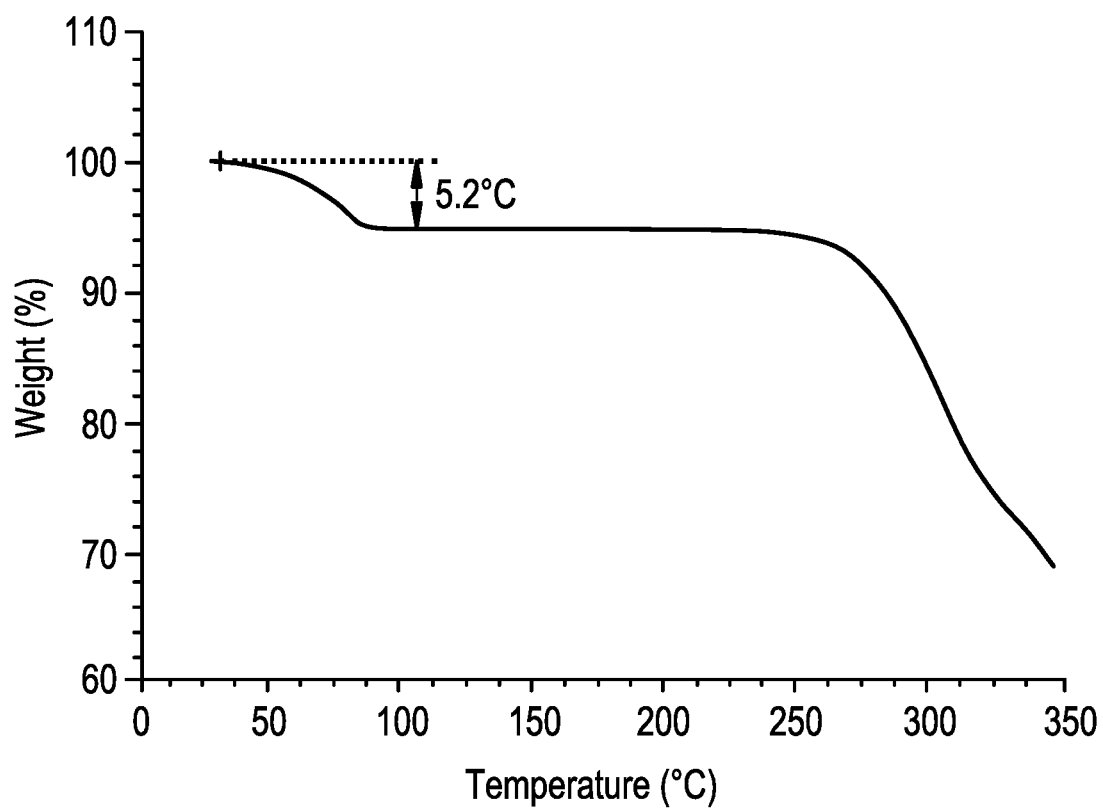
Figure 23B:
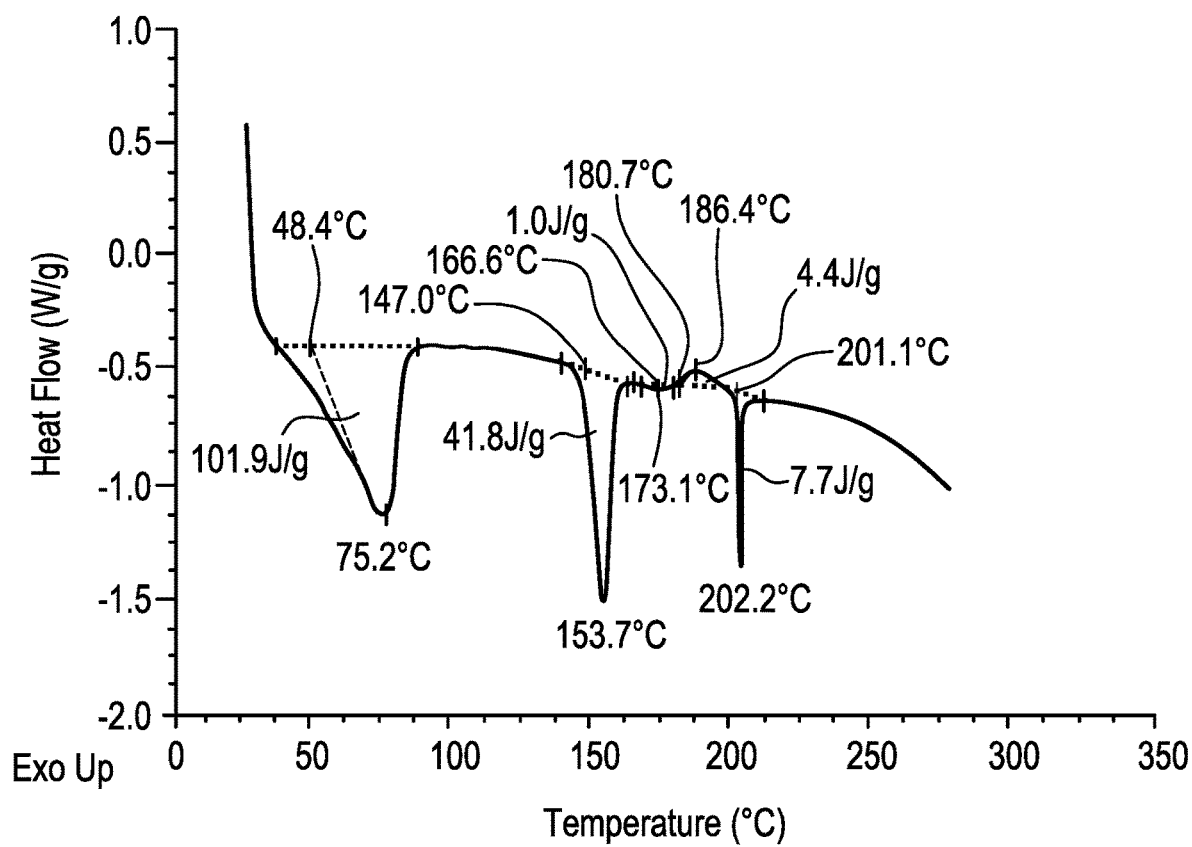

A suspension of embodiment 1s (30 mg) in each solvent was placed in a platform shaker incubator and subjected to a series of heat-cool cycles from ambient to approximately 50° C. for 24 h. This was achieved by switching the heating on and off every 4 hours. Shaking was maintained throughout. An aliquot from each sample was taken and allowed to air-dry for 2 h. The air-dried solids were analyzed by XRPD, then vacuum dried using a vacuum oven (RT, 24 h) and were re-analyzed by XRPD. Each sample obtained in this experiment was vacuum dried and after vacuum drying each sample was analyzed by XRPD incubation at elevated temperature. The following solvents, where total solvent amount added is noted in parenthesis immediately after the solvent, were used according to this procedure which yielded the noted embodiment: Water (20 mL) yielded embodiment 1s whose diffractogram is shown in FIG. 5; methanol (5 mL) yielded embodiment 22 whose diffractogram is shown in FIG. 13; ethanol (5 mL) yielded embodiment 1s whose diffractogram is shown in FIG. 5; 2-propanol (10 mL) yielded embodiment 27 whose diffractogram for this experiment is shown in FIG. 13; 1-propanol (10 mL) yielded embodiment 23 whose diffractogram is shown in FIG. 13; acetone (20 mL) yielded embodiment 1s whose diffractogram is shown in FIG. 5; ethyl acetate (20 mL) yielded a poorly crystalline form of embodiment 1s whose diffractogram is not shown; acetonitrile (20 mL) yielded a poorly crystalline embodiment 24 whose diffractogram is shown in FIG. 13; toluene (20 mL) yielded a poorly crystalline embodiment 1s whose diffractogram is not shown; isopropyl acetate (20 mL) yielded embodiment 18 whose diffractogram is shown in FIG. 13; methyl t-butyl ether (20 mL) yielded a poorly crystalline embodiment 1s whose diffractogram is not shown; 2-butanone (20 mL) yielded embodiment 26 whose diffractogram is shown in FIG. 13; THF (20 mL) yielded embodiment 18 whose diffractogram is shown in FIG. 13; diethyl ether (20 mL) yielded a poorly crystalline embodiment 1s whose diffractogram is not shown; methyl isobutyl ketone (20 mL) yielded embodiment 25 whose diffractogram is shown in FIG. 13; DCM (20 mL) yielded a poorly crystalline form of embodiment 1s whose diffractogram is not shown; heptane (20 mL) yielded embodiment 1s whose diffractogram is shown in FIG. 5; 1,4-dioxane (20 mL) yielded embodiment 27 whose diffractogram for this experiment is shown in FIG. 13; nitromethane (20 mL) yielded a poorly crystalline embodiment 1s whose diffractogram is not shown; propylene glycol (5 mL) yielded a poorly crystalline embodiment (diffractogram not shown); 2-methyl-tetrahydrofuran (20 mL) yielded embodiment 18 whose diffractogram is shown in FIG. 13; tetralin (20 mL) yielded embodiment 1s whose diffractogram is shown in FIG. 5; 3-methyl-butanol (20 mL) yielded embodiment 18 whose diffractogram is shown in FIG. 13; anisole (20 mL) yielded embodiment 16 whose diffractogram is shown in FIG. 13 and whose TGA and DSC are shown in FIGS. 23A and 23B, respectively.; 1,2-dimethoxyethane (20 mL) yielded embodiment 29 whose diffractogram is shown in FIG. 13; cumene (20 mL) yielded embodiment 1s whose diffractogram is shown in FIG. 5; diisopropyl ether (20 mL) yielded embodiment 17 whose diffractogram is shown in FIG. 13; ethanol:water (95:5, 20 mL) yielded embodiment 30 whose diffractogram is shown in FIG. 13; acetonitrile:water (95:5, 20 mL) yielded a poorly crystalline form of embodiment 1s whose diffractogram is not shown; and polyethylene glycol (5 mL) yielded embodiment 31 whose diffractogram is shown in FIG. 13.

Figure 14:
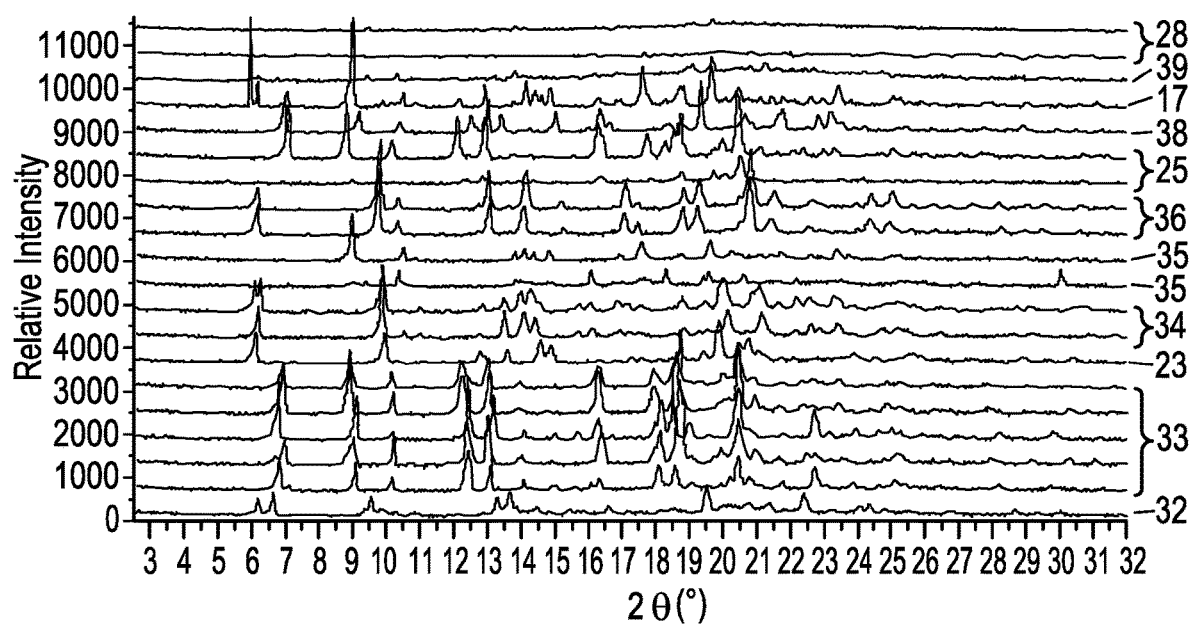

Incubation of Embodiment 1s at 60° C. Embodiment 1s (30 mg) was treated with solvent and shaken at 60° C. for 24 h. An aliquot was taken out and allowed to air-dry for 16 h. The dried samples were then analyzed by XRPD. The following solvents, where total solvent amount added is noted in parenthesis immediately after the solvent, were used according to this procedure which yielded the noted embodiment: Water (10 mL) yielded embodiment 1s whose diffractogram is shown in FIG. 5; ethanol (10 mL) yielded embodiment 32 whose diffractogram is shown in FIG. 14; 2-propanol (10 mL) yielded embodiment 33 whose diffractogram is shown in FIG. 14; 1-propanol (10 mL) yielded embodiment 23 whose diffractogram is shown in FIG. 14; acetone (10 mL) yielded embodiment 1s whose diffractogram is shown in FIG. 5; ethyl acetate (10 mL) yielded embodiment 34 whose diffractogram is shown in FIG. 14; acetonitrile (10 mL) yielded embodiment 35 whose diffractogram is shown in FIG. 14; toluene (10 mL) yielded embodiment 36 whose diffractogram is shown in FIG. 14; isopropyl acetate (10 mL) yielded embodiment 25 whose diffractogram for this experiment is shown in FIG. 14; methyl t-butyl ether (10 mL) yielded embodiment 35 whose diffractogram is shown in FIG. 14; 2-butanone (10 mL) yielded embodiment 38 whose diffractogram is shown in FIG. 14; THF (10 mL) yielded embodiment 33 whose diffractogram for this experiment is shown in FIG. 14; diethyl ether (10 mL) yielded embodiment 1s whose diffractogram is shown in FIG. 5; methyl isobutyl ketone (10 mL) yielded embodiment 25 whose diffractogram for this experiment is shown in FIG. 14; DCM (10 mL) yielded embodiment 1s whose diffractogram is shown in FIG. 5; heptane (10 mL) yielded embodiment 1s whose diffractogram is shown in FIG. 5; 1-4-dioxane (10 mL) yielded embodiment 33 whose diffractogram is shown in FIG. 14; nitromethane (10 mL) yielded embodiment 1s whose diffractogram is shown in FIG. 5; propylene glycol (10 mL) yielded embodiment 28 whose diffractogram for this experiment is shown in FIG. 14; 2-methyl-tetrahydrofuran (10 mL) yielded embodiment 33 whose diffractogram is shown in FIG. 14; tetralin (10 mL) yielded a mixture (diffractogram of the mixture not shown) of embodiment is whose diffractogram is shown in FIG. 5 and embodiment 19 whose modulated DSC profile is shown in FIG. 9; 3-methyl-1-butanol (10 mL) yielded embodiment 33 whose diffractogram is shown in FIG. 14; anisole (10 mL) yielded embodiment 36 whose diffractogram is shown in FIG. 14; 1,2-dimethoxyethane (10 mL) yielded embodiment 34 whose diffractogram is shown in FIG. 14; cumene (10 mL) yielded embodiment 1s whose diffractogram is shown in FIG. 5; diisopropyl ether (10 mL) yielded embodiment 17 whose diffractogram is shown in FIG. 8; ethanol:water (95:5, 10 mL) yielded embodiment 28 whose diffractogram is shown in FIG. 14; and polyethylene glycol (5 mL) yielded embodiment 39 whose diffractogram for this experiment is shown in FIG. 14

High Temperature Maturation

Figure 15:
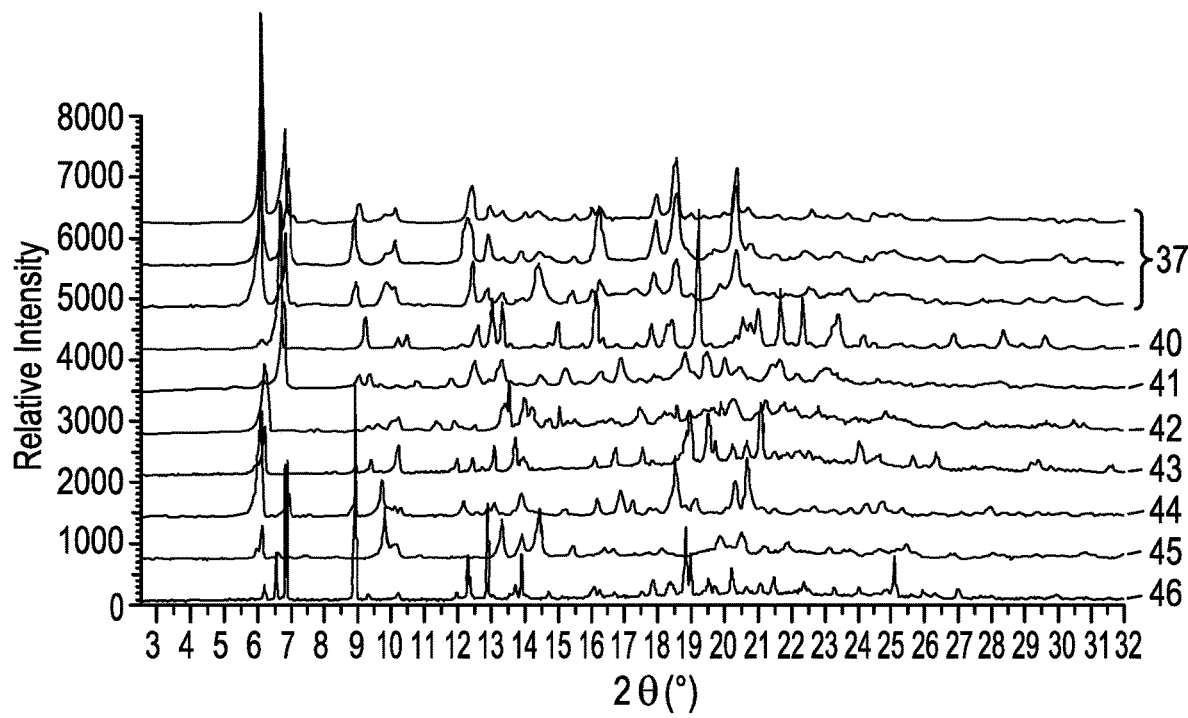

Each of a plurality of embodiment 19 (25 mg) samples was treated with an amount of a solvent as indicated below yielding in turn a plurality of samples, each agitated at 60° C. for 24 h. Solids from each sample were isolated, air-dried for 16 h and analyzed by XRPD. The following solvents, where total solvent amount added is noted in parenthesis immediately after the solvent followed by dissolution extent, were used according to this procedure which yielded the noted embodiment: Water (125 µL, suspension) yielded embodiment 1s whose diffractogram is shown in FIG. 5; methanol (125 µL, suspension) yielded embodiment 1s whose diffractogram is similar to the diffractogram for embodiment 1s shown in FIG. 5 except that it displays some additional peaks; ethanol (125 µL, suspension) yielded embodiment 1s whose diffractogram is shown in FIG. 5; 2-propanol (75 µL, suspension) yielded embodiment 37 whose diffractogram is shown in FIG. 15; 1-propanol (75 µL, suspension) yielded embodiment 40 whose diffractogram is shown in FIG. 15; acetone (75 µL, suspension) yielded embodiment 1s whose diffractogram is shown in FIG. 5; ethyl acetate (75 µL, suspension) yielded embodiment 1s whose diffractogram is shown in FIG. 5; acetonitrile (75 µL, suspension) yielded embodiment is whose diffractogram is shown in FIG. 5; toluene (75 µL, suspension) yielded embodiment is whose diffractogram is shown in FIG. 5; isopropyl acetate (75 µL, suspension) yielded embodiment 37 whose diffractogram is shown in FIG. 15; methyl t-butyl ether (75 µL, suspension), yielded embodiment 33 whose diffractogram is shown in FIG. 14; 2-butanone (75 µL, suspension) yielded embodiment 1s whose diffractogram is shown in FIG. 5; THF (75 µL, suspension) yielded embodiment 37 whose diffractogram is shown in FIG. 15; diethyl ether (150 µL, suspension) yielded embodiment 1s whose diffractogram is shown in FIG. 5; methyl isobutyl ketone (150 µL, suspension) yielded embodiment 33 whose diffractogram is shown in FIG. 14; DCM (75 µL, suspension) yielded embodiment 1s whose diffractogram is shown in FIG. 5; heptane (150 µL, suspension) yielded embodiment 41 whose diffractogram is shown in FIG. 15; 1,4-dioxane (75 µL, suspension) yielded embodiment 3c whose diffractogram is shown in FIG. 5; nitromethane (75 µL, suspension) yielded embodiment 42 whose diffractogram is shown in FIG. 15; propylene glycol (75 µL, suspension) yielded embodiment 43 whose diffractogram is shown in FIG. 15; 2-methyl-tetrahydrofuran (150 µL, suspension) yielded embodiment 33 whose diffractogram is shown in FIG. 14; tetralin (150 µL, suspension), yielded embodiment 33 whose diffractogram is shown in FIG. 14; 3-methyl-1-butanol (75 µL, suspension) yielded embodiment 33 whose diffractogram is shown in FIG. 14; anisole (150 µL, suspension) yielded embodiment 1s whose diffractogram is shown in FIG. 5; 1,2-dimethoxyethane (75 µL, suspension) yielded embodiment 1s whose diffractogram is shown in FIG. 5; cumene (150 µL, suspension) yielded embodiment 44 whose diffractogram is shown in FIG. 15; diisopropyl ether (150 µL, suspension) yielded embodiment 33 whose diffractogram is shown in FIG. 14; ethanol:water (95:5, 75 µL, suspension) yielded embodiment 45 whose diffractogram is shown in FIG. 15; acetonitrile:water (95:5, 75 µL, suspension) yielded embodiment 1s whose diffractogram showed cell expansion when compared to the diffractogram shown in FIG. 5; and polyethylene glycol (75 µL, suspension) yielded embodiment 46 whose diffractogram is shown in FIG. 15.

Thermocycling

Figure 16:
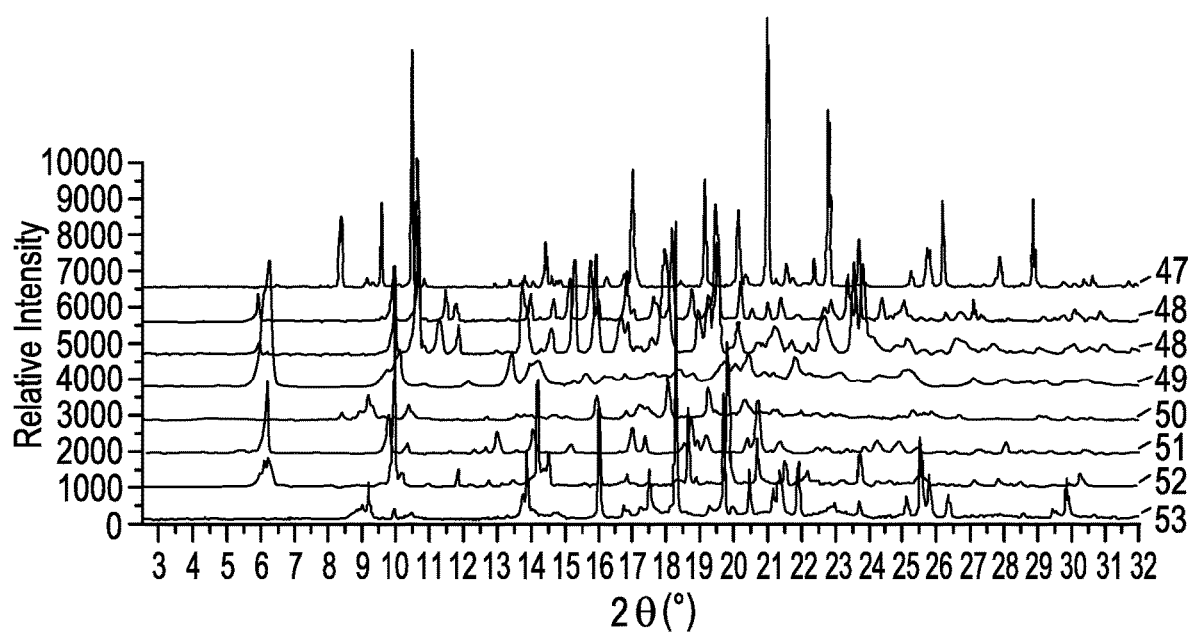

Each of a plurality of embodiment 19 (25 mg) samples was treated with an amount of a solvent as indicated below yielding in turn a plurality of samples, each sample was matured by thermocycling (40° C.-60° C., 4 h cycles) for 24 h. Solids were isolated, air-dried for 16 h and analyzed by XRPD. The following solvents, where total solvent amount added is noted in parenthesis immediately after the solvent followed by the observed appearance at 24 hours, were used according to this procedure which yielded the noted embodiment: Water (125 µL, green tinge solid) yielded embodiment 1s whose diffractogram is shown in FIG. 5; methanol (75 µL, transparent solid) yielded embodiment 11 whose diffractogram showed peaks that were shifted at high angle when compared to the diffractogram in FIG. 7; ethanol (100 µL, green tinge solid) yielded embodiment 1s whose diffractogram is shown in FIG. 5; 2-propanol (75 µL, yellow tinge solid) yielded embodiment 33 whose diffractogram is shown in FIG. 14; 1-propanol (75 µL, white suspension) yielded embodiment 33 whose diffractogram is shown in FIG. 14; acetone (75 µL, green tinge solid) yielded embodiment 47 whose diffractogram is shown in FIG. 16; ethyl acetate (75 µL, white suspension) yielded embodiment 33 whose diffractogram is shown in FIG. 14; acetonitrile (75 µL, white suspension) yielded a poorly crystalline of embodiment 6 whose diffractogram is shown in FIG. 3; toluene (75 µL, transparent solid) yielded embodiment 36 whose diffractogram is shown in FIG. 14; isopropyl acetate (75 µL, white solid) yielded embodiment 33 whose diffractogram is shown in FIG. 14; methyl t-butyl ether (75 µL, white suspension) yielded embodiment 6 whose diffractogram is shown in FIG. 3; 2-butanone (75 µL, off-white solid) yielded embodiment 33 whose diffractogram is shown in FIG. 14; THF (75 µL, off-white solid) yielded embodiment 48 whose diffractogram is shown in FIG. 16; diethyl ether (150 µL, off-white solid) yielded embodiment 49 whose diffractogram is shown in FIG. 16; methyl isobutyl ketone (150 µL, off-white solid) yielded embodiment 25 whose diffractogram is very similar to the diffractogram for embodiment 25 that is shown in FIG. 13; DCM (125 µL, white suspension) yielded embodiment 1s whose diffractogram is shown in FIG. 5; heptane (150 µL, white solid) yielded embodiment 19 whose modified DSC profile is shown in FIG. 9; 1,4-dioxane (75 µL, white solid) yielded embodiment 3c whose diffractogram is shown in FIG. 5; nitromethane (75 µL, white suspension) yielded embodiment 50 whose diffractogram is shown in FIG. 16; propylene glycol (75 µL, cream suspension) yielded embodiment 10 whose diffractogram is very similar to the diffractogram for embodiment 10 (as shown in FIG. 16), except that it shows an amorphous halo; 2-methyltetrahydrofuran (150 µL, white solid) yielded embodiment 48 whose diffractogram is shown in FIG. 16; tetralin (150 µL, white solid) yielded a poorly crystalline embodiment whose diffractogram is not shown; 3-methyl-1-butanol (75 µL, white suspension) yielded embodiment 25 whose diffractogram is shown in FIG. 13; anisole (150 µL, white suspension) yielded embodiment 51 whose diffractogram is shown in FIG. 16; 1,2-dimethoxyethane (75 µL, white suspension) yielded embodiment 52 whose diffractogram is shown in FIG. 16; cumene (150 µL, white solid) yielded a poorly crystalline embodiment whose diffractogram is not shown; diisopropyl ether (150 µL, white solid) yielded embodiment 6 whose diffractogram is shown in FIG. 3; ethanol:water (95:5, 75 µL, transparent solid) yielded embodiment 11 whose diffractogram is shown in FIG. 7; acetonitrile:water (95:5, 75 µL, transparent solid) yielded embodiment 53 whose diffractogram is shown in FIG. 16; and propylene glycol (75 µL, pale pink suspension) yielded embodiment 31 whose diffractogram is very similar to the diffractogram for embodiment 31 (as shown in FIG. 13), except that it shows an amorphous halo.

Any one of embodiments 11, 11b, 12, 13, 14, 15, 16, 17, 18, 19, 20, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 and 53 of compound Ex. 1 and any combination thereof is an embodiment of compounds according to this invention. Still other embodiments of compounds according to this invention include compound Ex. 1 as a non-hygroscopic solvate, such as embodiment 11 of compound Ex. 1. Still other embodiments of compounds according to this invention include compound Ex. 1 in amorphous form, such as embodiment 19 of compound Ex. 1. Any one of embodiments 11, 16, 17, and 18 of compound Ex. 1 and any combination thereof is an embodiment of compounds according to this invention. Further embodiments of this invention include compounds according to this invention in the form of pharmaceutically acceptable co-crystals. Additional embodiments of this invention include compounds according to this invention in the form of pharmaceutically acceptable salts.

Examples 1-12 are JAK inhibitors and were tested in enzymatic and cellular assays. The results of the enzymatic assay are presented in Table 4 which is entitled Results of Enzymatic Inhibition Assays. Examples 1-12 were also tested in three cellular assays: IL-2 pSTAT5 (JAK1/JAK3), IFNα pSTAT4 (JAK1/TYK2) and GM-CSF pSTAT5 (JAK2/JAK2) with the results presented in Table 5 entitled Cell-Based Assay Data. Below is the description of how the enzymatic assay was performed including the materials used in the assay (under the heading Materials), how the assay was set up (under the heading Assay protocol), and the method used to analyze the data (under the heading High-throughput Mass Spectrometry (HTMS) Method).

Enzymatic Inhibition Assay

Materials

Substrate (NH2-KGGEEEEYFELVKK-CO2), internal standard peptide (NH2-SWGAIETDKEYYTVKD-CO2) and product peptide (for standard curve only) (NH2-KG-GEEEEY-Pi-FELVKK-CO2), were purchased from AnaSpec (Fremont, Calif., USA). JAK1-JH1JH2 (574-1154 with a His-GST Tag and a C-terminal tev (ENLYFQ-G) cleavage site), JAK3-JH1JH2 (512-1124 with a GST Tag and a C-terminal tev (ENLYFQ-G) cleavage site), and Tyk2-JH1JH2 (8H_tev_580-1182-C936A-C1142A with a C-terminal tev (ENLYFQ-G) cleavage site) were purified internally. JAK2-JH1JH2 (532-1132 with a GST tag and C-terminal tev (ENLYFQ-G) cleavage site), was purchased from Invitrogen. LC/MS grade water and acetonitrile (ACN), were purchased from HoneyWell, Burdick & Jackson (Muskegon, Mich., USA). Dimethylsulfoxide 99.8% (DMSO) and trifluoroacetic acid 99.5% (TFA) were purchased from EMD Chemical (Gibbstown, N.J., USA). Adenosine triphosphate (ATP), 4-morpholinepropanesulfonic acid (MOPS), magnesium chloride ($MgCl_2$), ethylenediaminetetraacetic acid (EDTA), dithiothreitol (DTT), formic acid >95% (FA) and Tween-20 were purchased from Sigma (St Louis, Mo., USA). 384-well polypropylene plates, Cat #781280 were purchased from Greiner (Monroe, N.C.), RapidFire™ cartridge A C4 Column (Agilent Technologies, Santa Clara, Calif.).

The HTMS experiments were performed in positive ionization mode on a RapidFire 300 instrument (Agilent Technologies, Santa Clara, Calif.), coupled with an ABSiex QTrap 4000 system with an Electrospray Ionization source (RF-MS) (Concord, ON, Canada). The RapidFire system was run with 3 Agilent 1200 series isocratic pumps Agilent Technologies (Santa Clara, Calif.) and one peristaltic pump model ISM832C from Ismatec (Wertheim, Germany). The entire system was operated using the RapidFire software interfaced with Analyst software for the mass spectrometer.

Assay Protocol 11-point dosing series were made for each compound by serially diluting 1:3 or 1:4 in DMSO, with point 12 being a DMSO control. From the serial dilution plates, sample was transferred to a 384 wells assay plate (#781280, Greiner, Monroe, N.C.) using Labcyte Echo (Sunnyvale, Calif.), or Biosero ATS (San Diego, Calif.). The compounds were tested in duplicate. Column 12 was used for positive controls, and column 24 contained negative controls with no enzyme added. A compound from our internal collection, with inhibitory activity for JAK isoforms, was used as a reference compound. The final concentration of DMSO was ≤0.25% in a 20 µL reaction. Assay conditions for each of the proteins are summarized in Table 3. The enzyme reaction was initiated by the addition of 10 µL of enzyme and ATP mixture to 10 µL of substrate solution prepared in reaction buffer (50 mM MOPS pH 7.5, 10 mM $MgCl_2$, 1 mM EDTA, 2 mM DTT, 0.002% Tween-20). The Tyk2 enzyme was pre-incubated with 2 mM ATP for 30 min prior to the reaction initiation. Immediately after the addition of the enzyme to the reaction mixture, the plate was centrifuged at 1000 rpm for 1 minute and incubated at 25° C. for 45 minutes for JAK3 and 90 minutes for JAK1, JAK2 and Tyk2. The reaction was quenched by the addition of 20 μL of 0.5 TFA containing 0.15 μM of internal standard peptide using Multidrop Combi reagent dispenser (Thermo Scientific, Waltham, Mass.). Several wells in column 24 were typically used for the product standard curve. After the quench, the assay plate was centrifuged at 3000 rpm for 3 minutes and sealed with pierceable aluminum foil (Cat #06644-001, Agilent) using a PlateLoc (Agilent Technologies, Santa Clara, Calif.). The plates then were transferred on to the RapidFire for the MS analysis. Compound inhibition was assessed by a decrease of the phosphorylated product levels in sample wells compared to the non-inhibited enzyme reaction. The assay conditions for the above assays are shown in Table 3 and the results of Ex. 1-12 as tested in these assays are shown in Table 4.

TABLE 3

Assay conditions for JAK family enzyme assays*

| Enzyme | [enzyme], nM | [ATP], μM | [Substrate], μM | [IS], nM |
|---|---|---|---|---|
| JAK1-JH1JH2 | 8.0 | 12.5 | 200 | 100 |
| JAK2-JH1JH2 | 7.0 or 3.6 | 30 | 40 | 100 |
| JAK3-JH1JH2 | 2.0 | 150 | 40 | 100 |
| Tyk2-JH1JH2 | 25 or 14.7 | 50 | 200 | 100 |

*Reaction buffer: 50 mM MOPS, pH 7.5 10 mM MgCl$_2$, 1 mM EDTA, 2 mM DTT, 0.002% Tween-20; "IS" stands for internal standard peptide; "Substrate" stands for peptide.

High-Throughput Mass Spectrometry (HTMS) Method

The sample analysis on the RapidFire was performed using a mobile phase A1 consisting of Water/TFA/FA (100: 0.01:0.1, v/v/v), a mobile phase B1 consisting of ACN/Water/TFA/FA (80:20:0.01:0.1, v/v/v). The following run parameters were used: state 1 (aspirate), 250 ms; state 2 (load/wash), 3000 ms; state 3 (elute), 4000 ms; state 4 (re-equlibrate), 1000 ms with a flow rate of 1.25 mL/min. The samples were aspirated directly from the 384-well assay plate and delivered onto RF-MS microscale solid-phase C4 extraction cartridge (Type A). The undesired component such as salt, cofactor, detergent and large protein were washed out and the retained analytes (substrate, product and IS) were coeluted directly onto the ABSiex Qtrap 4000 system. The quantification of peptide (substrate), phosphopeptide (product) and internal standard peptide (IS) was performed by MRM using 562→136.0, 589.2→215.7 and 953.2→158.8 (or 974.2→158.8) transitions respectively.

TABLE 4

Results of Enzymatic Inhibition Assays

| Test Compound | JAK1_JH1JH2 IC$_{50}$ (nM) | JAK2_I_JH1JH2 IC$_{50}$ (nM) | JAK3_I_JH1JH2 IC$_{50}$ (nM) | Tyk2_I_JH1JH2 IC$_{50}$ (nM) |
|---|---|---|---|---|
| A | <0.2 | <0.2 | 12.4 | 0.9 |
| B | <0.2 | <0.2 | 13.4 | <0.2 |
| C | <0.2 | 0.6 | 49.7 | 0.2 |
| Ex. 1 | 0.4 | 8.6 | 92.2 | 7.4 |
| Ex. 2 | 0.2 | 1.0 | 33.9 | 1.5 |
| Ex. 3 | 0.2 | 6.2 | 82.8 | 11.6 |
| Ex. 4 | 0.1 | 6.6 | 96.2 | 2.2 |
| Ex. 5 | 0.3 | 2.1 | 23.1 | 4.1 |
| Ex. 6 | 0.1 | 1.4 | 28.2 | 1.1 |
| Ex. 7 | 0.2 | 5.6 | 98.4 | 4.8 |
| Ex. 8 | 0.4 | 7.0 | 75.6 | 6.6 |
| Ex. 9 | 0.2 | 6.6 | 79.9 | 4.7 |
| Ex. 10 | 1.0 | 6.5 | 87.5 | 9.0 |
| Ex. 11 | 0.4 | 1.6 | 30.3 | 1.5 |
| Ex. 12 | 0.9 | 9.4 | 101.3 | 8.7 |

Cellular Assays

IL-2 pSTAT5 (JAK1/JAK3) Cellular Assay

The AlphaLISA assay (based on Alpha Technology from PerkinElmer) was performed by first plating freshly thawed PBMCs (Biological Specialty Corporation) in 384-well plates at 30,000 cells per 4 μL per well in HBSS (Hanks' Balanced Salt Solution) containing 0.1% IgG (immunoglobulin G)-free, protease-free BSA (bovine serum albumin) (Jackson ImmunoResearch Cat. No. 001-000-161). The cells were then treated with 2 μL/well of compounds diluted in DMSO at half-log titrated concentrations, with a highest test concentration of 10 μM and 0.5% final DMSO concentration, for thirty minutes at 37° C. Next, the cells were stimulated with 2 μL/well of IL-2 (R&D Systems Cat. No. 202-IL-050) at 5 ng/mL for thirty minutes at 37° C. The cellular reactions were terminated by the addition of 2 μL/well of lysis buffer (PerkinElmer Cat. No. ALSU-PST5-A10K) followed by an incubation of five minutes at room temperature. 5 μL/well of acceptor mix (PerkinElmer Cat. No. ALSU-PST5-A10K) was added to the cells and incubated in the dark for one hour at room temperature. Then, 5 μL/well of donor mix (PerkinElmer Cat. No. ALSU-PST5-A10K) was added to the cells and incubated in the dark overnight at room temperature. Finally, the plates were read on a PerkinElmer EnVision for detection of the time-resolved fluorescence signal. The percentage of IL-2-dependent pSTAT5 inhibition was determined at the compound test concentrations; and for each compound, a dose curve was generated and the IC$_{50}$ was calculated. Compound IC$_{50}$ was calculated by nonlinear regression, sigmoidal dose response analysis of the half-log dilution titration curve of the compound concentration vs. Alpha signal. The acronym "Alpha" stands for amplified luminescent proximity homogeneous assay; the Alpha signal is a luminescent/fluorescent signal.

IFNα pSTAT4 (JAK1/TYK2) Cellular Assay

The AlphaLISA assay (based on Alpha Technology from PerkinElmer) was performed by first plating freshly thawed PBMCs (Biological Specialty Corporation) in 384-well plates at 100,000 cells per 6 μL per well in DMEM (Dulbecco's Modified Eagle Medium) containing 10% FBS (fetal bovine serum) and 1,000 I.U./mL penicillin and 1,000 µg/mL streptomycin. The cells were then treated with 2 µL/well of compounds diluted in DMSO at half-log titrated concentrations, with a highest test concentration of 10 µM and 0.5% final DMSO concentration, for thirty minutes at 37° C. Next, the cells were stimulated with 2 µL/well of IFNα (PBL Assay Science Cat. No. 11101-2) at 4 ng/mL for thirty minutes at 37° C. The cellular reactions were terminated by the addition of 2 µL/well of lysis buffer (PerkinElmer Cat. No. ALSU-PST4-A10K) followed by an incubation of five minutes at room temperature. 4 µL/well of acceptor mix (PerkinElmer Cat. No. ALSU-PST-4-A10K) was added to the cells and incubated in the dark for one hour at room temperature. Then, 4 µL/well of donor mix (PerkinElmer Cat. No. ALSU-PST4-A10K) was added to the cells and incubated in the dark overnight at room temperature. Finally, the plates were read on a PerkinElmer EnVision for detection of the time-resolved fluorescence signal. The percentage of IFNα-dependent pSTAT4 inhibition was determined at the compound test concentrations; and for each compound, a dose curve was generated and the $IC_{50}$ was calculated. Compound $IC_{50}$ was calculated by nonlinear regression, sigmoidal dose response analysis of the half-log dilution titration curve of the compound concentration vs. Alpha signal. The term "Alpha" is defined in the immediately preceding cellular assay description.

GM-CSF pSTAT5 (JAK2/JAK2) Cellular Assay

The AlphaLISA assay (based on Alpha Technology from PerkinElmer) was performed by first plating freshly thawed PBMCs (Biological Specialty Corporation) in 384-well plates at 30,000 cells per 4 µL per well in HBSS containing 0.1% IgG-free, protease-free BSA (Jackson ImmunoResearch Cat. No. 001-000-161). The cells were then treated with 2 µL/well of compounds diluted in DMSO at half-log titrated concentrations, with a highest test concentration of 10 µM and 0.5% final DMSO concentration, for thirty minutes at 37° C. Next, the cells were stimulated with 2 µL/well of GM-CSF (R&D Systems Cat. No. 215-GM-050) at 11 pg/mL for fifteen minutes at 37° C. The cellular reactions were terminated by the addition of 2 µL/well of lysis buffer (PerkinElmer Cat. No. ALSU-PST5-A10K) followed by an incubation of five minutes at room temperature. 5 µL/well of acceptor mix (PerkinElmer Cat. No. ALSU-PST5-A10K) was added to the cells and incubated in the dark for one hour at room temperature. Then, 5 µL/well of donor mix (PerkinElmer Cat. No. ALSU-PST5-A10K) was added to the cells and incubated in the dark overnight at room temperature. Finally, the plates were read on a PerkinElmer EnVision for detection of the time-resolved fluorescence signal. The percentage of GM-CSF-dependent pSTAT5 inhibition was determined at the compound test concentrations; and for each compound, a dose curve was generated and the $IC_{50}$ was calculated. Compound $IC_{50}$ was calculated by nonlinear regression, sigmoidal dose response analysis of the half-log dilution titration curve of the compound concentration vs. Alpha signal. The term "Alpha" is defined in the IL-2 pSTAT5 (JAK1/JAK3) cellular assay description.

TABLE 5

Cell-Based Assay Data

| Test Compound | IL-2 pSTAT5 (JAK1/JAK3) $IC_{50}$ (nM) | IFNα pSTAT4 (JAK1/TYK2) $IC_{50}$ (nM) | GM-CSF pSTAT5 (JAK2/JAK2) $IC_{50}$ (nM) |
|---|---|---|---|
| Ex. 1 | 21.6 | 59.5 | 83.9 |
| Ex. 2 | 9.0 | 20.8 | 61.0 |
| Ex. 3 | 6.4 | 10.1 | 21.9 |
| Ex. 4 | 35.5 | 64.7 | 119.4 |
| Ex. 5 | 6.4 | 38.1 | 28.9 |
| Ex. 6 | 6.7 | 39.4 | 25.1 |
| Ex. 7 | 9.7 | 38.5 | 67.3 |
| Ex. 8 | 20.6 | 42.8 | 33.8 |
| Ex. 9 | 11.2 | 35.9 | 26.9 |
| Ex. 10 | 16.8 | 40.4 | 44.6 |
| Ex. 11 | 49.1 | 96.5 | 201.5 |
| Ex. 12 | 13.9 | 81.4 | 75.4 |

Examples 1-12 were tested in solubility and permeability assays. The results of the solubility assay are presented in Table 6 which is entitled Solubility Assay Data and the results of the permeability assay are presented in Table 7 entitled MDCK-MDR1 Permeability Data. These solubility and permeability assays are described below under the headings Solubility Assays and Permeability Assays, respectively.

Solubility Assays

Solubility measurements were conducted in the following solubility media: Simulated gastric (34.2 mM of sodium chloride and 100 mM of hydrochloric acid) or simulated intestinal fluids (fasted state [pH 6.5]: 3 mM of sodium taurocholate, 0.75 mM of lecithin, 28.4 mM of monobasic sodium phosphate, 8.7 mM of sodium hydroxide, and 105.9 mM of sodium chloride). Test compounds were dissolved in DMSO at a concentration of 10 mM. The test compounds were dispensed (20 µL) into Nunc 1-mL-96-Deep-Well-PP plates, and the DMSO was evaporated via nitrogen blow down from a TurboVap 96 for 6 hours or until a dry residue was produced. Then, 400 µL of solubility media was added to the well containing the dry solid. A Pre-Slit Well Cap was securely placed over the well plate block, and the samples were vigorously stirred for 2-5 days at ambient temperature. After the incubation period, the samples were filtered through an AcroPrep 1-mL-96-Filter plate into a new 2-mL-96-Deep-Well-PP plate, and the supernatants were quantified by UV-HPLC using a 3-point calibration ranging from 0.004-0.55 mM. The solubility for each compound was calculated from the following equation:

$$\text{Solubility} = \frac{\text{Sample Peak Area}}{\text{Average Response Factor from 3 Standards}}.$$

The solubility values were in the range of 4-400 µM. Values outside of this range were reported as either <4 µM or >400 µM. Solubilities are reported as long as the compound under study was sufficiently stable to complete the corresponding solubility determination.

TABLE 6

Solubility Assay Data

| Test Compound | SGF solubility (μM) | SIF solubility (μM) |
|---|---|---|
| A | >400 | >400 |
| B | >400 | 75 |
| C | >400 | >400 |
| Ex. 1 | >400 | 387 |
| Ex. 2 | >400 | >400 |
| Ex. 3 | >400 | >400 |
| Ex. 4 | >400 | >400 |
| Ex. 5 | >400 | 198 |
| Ex. 6 | >400 | >400 |
| Ex. 7 | >400 | 81 |
| Ex. 8 | >400 | >400 |
| Ex. 9 | >400 | >400 |
| Ex. 10 | >400 | 359 |
| Ex. 11 | >400 | >400 |
| Ex. 12 | >400 | >400 |

Permeability Assays

Permeability measurements were conducted according to the Cyprotex protocol using the MDCK-MDR1 cell line obtained from the NIH (Rockville, Md., USA). Cells between passage numbers 6-30 were seeded onto a Multi-screen Plate™ (Millipore) at a cell density of $3.4 \times 10^5$ cells/cm$^2$ and cultured for three days before permeability studies were conducted. The cells in this assay form a cohesive sheet of a single cell layer filing the surface area of the culture dish, also known as a confluent monolayer, and on day four the test compound was added to the apical side of the membrane and the transport of the compound across the monolayer was monitored over a time period of 60 min.

In a simple and basic way of introducing "A" and "B" terms that are often used in these assays, the apical ("A") side or compartment of an entity is the side of such entity that is exposed to the lumen or exterior environment, whereas the basolateral ("B") side or compartment is the side or compartment of such entity that is exposed to the typically internal environment, encompassing the opposite side. For example, when such entity is illustratively an intestinal epithelium cell, the apical side of such intestinal cell would be the side of the cell exposed to the intestinal lumen, whereas the basolateral side would be the side that is exposed to the blood.

Test compounds were dissolved in DMSO at a concentration of 10 mM. The dosing solutions were prepared by diluting test compound with assay buffer (Hanks Balanced Salt Solution), pH 7.4, at a final concentration of 5 μM. For assessment of apical to basolateral ("A-B") permeability, buffer was removed from the apical compartment and replaced with test compound dosing solution with or without the permeability glycoprotein ("PgP", "P-gP", "Pgp" or "P-gp") inhibitor elacridar (2 μM). For assessment of basolateral to apical ("B-A") permeability, buffer was removed from the companion plate and replaced with test compound dosing solution. Incubations were carried out in duplicate at 37° C. in an atmosphere of 5% CO2 with a relative humidity of 95%. Each assay included the reference markers propranolol (high permeability) and prazosin (PgP substrate). After incubation for 60 minutes, apical and basolateral samples were diluted and test compounds quantified by LC/MS/MS using an 8-point calibration in the range 0.0039 to 3 μM with appropriate dilution of the samples (receiver dilution factor=1; donor and Co dilution factor=10). The permeability coefficient ($P_{app}$) for each compound was calculated from the following equation: $P_{app} = (dQ/dt)/(C_0 \times S)$, where dQ/dt is the rate of permeation of the drug across the cells, Co is the donor compartment concentration at time zero, and S is the area of the cell monolayer.

The percent recovery was measured for all incubation conditions. These measurements did not reveal unacceptable compound/plate binding or compound accumulation in the cell monolayer.

The second and third columns in Table 7 show the values of $P_{app(A-B)}$ for the apical-to-basolateral compound transport without (second column) and with a P-gp inhibitor (third column, noted as $P^e_{app(A-B)}$) that was elacridar. $P_{app(A-B)}$ gives an indication of permeation extent across the cells in this assay, which is envisaged to model the transcellular transport across Pgp-expressing cells, such as Pgp-expressing gastrointestinal tract cells. $P^e_{app(A-B)}$ values ($P_{app(A-B)}$ in the presence of the P-gp inhibitor) given in column 3 are determined to confirm the role of P-gp in the compound efflux. The fourth column in Table 7 shows the values of $P_{app(B-A)}$ for the basolateral-to-apical compound transport. Test compound efflux ratios are given in the fifth column of Table 7 as $P_{app(B-A)}/P_{app(A-B)}$ by using the corresponding permeability coefficient values from the fourth and second columns in the same table. The efflux ratios (fifth column, Table 7) are consistently greater than 2 for compounds (A)-(C) and also for compounds Ex. 1-12, which indicates that compound efflux occurs for all such compounds.

$P_{app(A-B)}$ values in column 2 are generally low and comparable for reference compounds (A)-(C) and also for compounds Ex. 1-12. These low values indicate low permeability for all such compounds, which is due to the P-gp effects since all such compounds are P-gp substrates as indicated by the values given in column 5 being all greater than 2. To be characterized as having low permeability, the values given in the third and fourth columns for $P^e_{app(A-B)}$ and $P_{app(B-A)}$, respectively, should be low. However, these data show that the $P_{app(B-A)}$ values for compounds (A)-(C) are greater than the corresponding values compounds Ex. 1-12.

The integrity of each monolayer was monitored by examining the permeation of *lucifer* yellow by fluorimetric analysis. This examination revealed that the cells in this assay maintained a satisfactory confluent monolayer.

TABLE 7

MDCK-MDR1 Permeability Data

| Test Compound** | MDCK-MDR1 $P_{app(A-B)}$ ($10^{-6}$ cm/sec) @ 5 (μM) | MDCK-MDR1 $P^e_{app(A-B)}$ ($10^{-6}$ cm/sec) @ 5 (μM) | MDCK-MDR1 $P_{app(B-A)}$ ($10^{-6}$ cm/sec) @ 5 (μM) | $P_{app(B-A)}/P_{app(A-B)}$ |
|---|---|---|---|---|
| A | 1.3 | 22 | 55.3 | 43 |
| B | 0.4 | 1.7 | 23.5 | 59 |
| C | 0.5 | 2.5 | 23.1 | 46 |
| Ex. 1 | <0.5, 0.4 | <0.5, 1.1 | 0.9, 1.1 | >1.9, 3.3 |
| Ex. 2* | 1.1 | 1.6 | 4.8 | 4.4 |
| Ex. 3 | <0.4, <0.5 | 2.3, 1.6 | 17, 16 | >41, >33 |
| Ex. 4 | 0.1 | 0.5 | 1.3 | 8.7 |
| Ex. 5 | <0.4, <0.5 | 0.7, 0.5 | 1.8, 2.1 | >4.8, >4.5 |
| Ex. 6 | <0.3, <0.3 | 0.9, 1.1 | 2.5, 2.6 | >8.4, >8.7 |
| Ex. 7 | <0.4 | 1.2 | 3.6 | >9 |
| Ex. 8 | 0.1 | 0.5 | 1.7 | 11.5 |
| Ex. 9 | <0.4 | 0.6 | 1.8 | >4.2 |
| Ex. 10 | <0.4 | 1.1 | 7.1 | >16.9 |
| Ex. 11 | <0.4 | 0.8 | 1.1 | >2.9 |
| Ex. 12 | <0.5 | 0.6 | 1.1 | >2.2 |

*Starting concentration was measured to be >7 μM for A to B, A to B (with elacridar), and B to A conditions.
**Unless indicated otherwise, compounds (A)-(C) and Ex. 1-12 were tested at a concentration of 5 μM. For data shown in cells with two data points, compounds were tested twice.

In Vivo Studies

Oral Dosing—Protocol 1

Three non-fasted female C57BL/6 mice were orally administered test compound at a dose of 25 mg/kg p.o. as a solution in 20% hydroxypropyl-beta-cyclodextrin (HPβCD) at a dose volume of 5 mL/kg. Blood samples were collected at 0.5, 2, and 4 h post dose via retro-orbital bleed or venipuncture of the dorsal metatarsal vein. Blood samples were collected into tubes containing anticoagulant (Heparin-Na) and placed on wet ice. The plasma fraction was separated by centrifugation and frozen at −20° C. for up to 4 h and −80° C. after 4 h unless analyzed shortly after sample collection. Colon samples were collected at 4 h post dose. From the beginning of the cecum, a 4-6 cm sample of the colon was dissected, cut open on the longitudinal axis, and the solid contents removed by flushing with 2 mL of saline. The colon was further washed by putting it in 5 mL of saline and shaken for 5 seconds. The colon sample was then patted dry, weighed, and homogenized as 1 part tissue (g) to 4 parts HPLC grade water (mL). Concentrations of the compound in plasma and colon homogenate were determined using a qualified liquid chromatography-triple quadrupole mass spectrometry (LC-MS/MS) method. This protocol was used to evaluate the following test compounds: Compounds (B) and (C) and Examples 6 and 11.

Oral Dosing Protocol 2

Three non-fasted female C57BL/6 mice were orally administered test compound at a dose of 25 mg/kg p.o. as a solution in 20% HPβCD at a dose volume of 5 mL/kg. Blood samples were collected at 0.5, 2, and 4 h post dose via retro-orbital bleed or dorsal metatarsal vein. Blood samples were collected into tubes containing anticoagulant (Heparin-Na) and placed on wet ice. The plasma fraction was separated by centrifugation and frozen at −20° C. for up to 4 h and −80° C. after 4 h unless analyzed shortly after sample collection. Colon samples were collected at 4 h post dose. From 2 cm below the cecum, a 4 cm sample of the colon was dissected, cut open on the longitudinal axis, and the solid contents removed by flushing with 2 mL of saline. The colon was further washed by putting it in 5 mL of saline and shaken for 5 seconds. The colon sample was then patted dry, weighed, and homogenized as 1 part tissue (g) to 4 parts HPLC grade water (mL). Concentrations of the compound in plasma and colon homogenate were determined using a qualified liquid chromatography-triple quadrupole mass spectrometry (LC-MS/MS) method. This protocol was used to evaluate the following test compounds: Compound (A) and Examples 1-5, 7-10, and 12.

IC Dosing-Protocol 3

Intracolonic (IC) dose group: Following anesthesia with isoflurane by inhalation, three non-fasted female C57BL/6 mice were administered the compound intracolonically through a small incision in the abdominal wall using a syringe and needle at a dose of 5 mg/kg as a solution in 20% HPβCD at a dose volume of 1 mL/kg. Blood samples were collected at 0.5, 2, and 4 h post dose via retro-orbital bleed. Blood samples were collected into tubes containing anticoagulant (Heparin-Na) and placed on wet ice. The plasma fraction was separated by centrifugation and frozen at −20° C. for up to 4 h and −80° C. after 4 h unless analyzed shortly after sample collection. Colon samples were collected at 4 h post dose. From 2 cm below the cecum, a 4-cm sample of the colon was dissected, cut open on the longitudinal axis, and the solid contents removed by flushing with 2 mL of saline. The colon was further washed by putting it in 5 mL of saline and shaken for 5 seconds. The colon sample was then patted dry, weighed, and homogenized as 1 part tissue (g) to 4 parts HPLC grade water (mL). Concentrations of the compound in plasma and colon homogenate were determined using a qualified liquid chromatography-triple quadrupole mass spectrometry (LC-MS/MS) method. This protocol was used to evaluate IC dosing of the following test compounds: Examples 1, 3, and 4.

Compounds Ex. 1-12 are further characterized by the physico-chemical properties given in Table 8. cLogP and tPSA values were calculated by using ChemBioDraw Ultra 14.0, where P is the n-octanol—water partition coefficient. The total polar surface area (tPSA) is calculated as the surface sum over all polar atoms, primarily oxygen and nitrogen, also including their attached hydrogens.

TABLE 8

Some physico-chemical properties of compounds Ex. 1-12

| Test Compound | cLog P | tPSA | # H bond donors | # H bond acceptors | # rotatable bonds |
|---|---|---|---|---|---|
| Ex. 1 | 0.94 | 113.11 | 3 | 5 | 6 |
| Ex. 2 | 2.31 | 88.17 | 2 | 4 | 3 |
| Ex. 3 | 1.58 | 92.88 | 2 | 4 | 6 |
| Ex. 4 | 0.54 | 116.67 | 2 | 5 | 6 |
| Ex. 5 | 0.24 | 102.11 | 2 | 5 | 5 |
| Ex. 6 | 0.86 | 102.11 | 2 | 5 | 6 |
| Ex. 7 | 1.25 | 116.67 | 2 | 5 | 6 |
| Ex. 8 | 1.13 | 113.11 | 3 | 5 | 6 |
| Ex. 9 | 1.14 | 108.48 | 2 | 5 | 5 |
| Ex. 10 | 1.35 | 116.67 | 2 | 5 | 6 |
| Ex. 11 | 1.50 | 117.27 | 3 | 5 | 5 |
| Ex. 12 | 0.57 | 113.11 | 3 | 5 | 6 |

What is claimed is:
1. A compound of formula

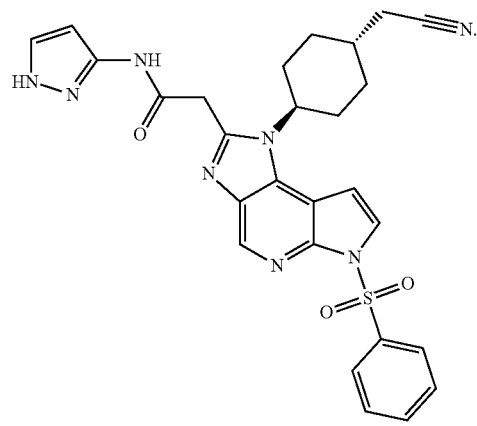 [SMILES: N#CC[C@H]1CC[C@H](n2c(CC(=O)Nc3cc[nH]n3)nc3cnc4c(ccn4S(=O)(=O)c4ccccc4)c32)CC1]

* * * * *